United States Patent
Ha et al.

(10) Patent No.: US 11,773,096 B2
(45) Date of Patent: Oct. 3, 2023

(54) SMALL-MOLECULE PI5P4K ALPHA/BETA INHIBITORS AND METHODS OF TREATMENT USING SAME

(71) Applicant: YALE UNIVERSITY, New Haven, CT (US)

(72) Inventors: Ya Ha, Mamaroneck, NY (US);
Jonathan Ellman, Guilford, CT (US);
Song Chen, New Haven, CT (US);
Caroline Chandra Tjin, Boston, MA (US); Fabrizio Micheli, Verona (IT);
Agostino Cianciulli, Verona (IT);
Claudia Beato, Verona (IT)

(73) Assignee: YALE UNIVERSITY, New Haven, CT (US)

( * ) Notice: Subject to any disclaimer, the term of this patent is extended or adjusted under 35 U.S.C. 154(b) by 0 days.

(21) Appl. No.: 17/267,488

(22) PCT Filed: Aug. 9, 2019

(86) PCT No.: PCT/US2019/045894
§ 371 (c)(1),
(2) Date: Feb. 9, 2021

(87) PCT Pub. No.: WO2020/033823
PCT Pub. Date: Feb. 13, 2020

(65) Prior Publication Data
US 2021/0292326 A1  Sep. 23, 2021

Related U.S. Application Data

(60) Provisional application No. 62/717,504, filed on Aug. 10, 2018.

(51) Int. Cl.
*C07D 475/00* (2006.01)

(52) U.S. Cl.
CPC .................. *C07D 475/00* (2013.01)

(58) Field of Classification Search
CPC .................. C07D 475/00; A61K 31/4985
See application file for complete search history.

(56) References Cited

U.S. PATENT DOCUMENTS

| | | |
|---|---|---|
| 6,806,272 B2 | 10/2004 | Bauer et al. |
| 9,351,974 B2 | 5/2016 | Jin et al. |
| 2006/0004711 A1 | 1/2006 | Naam |
| 2006/0047118 A1 | 3/2006 | Stadtmueller et al. |
| 2007/0004960 A1 | 1/2007 | Azzolina |
| 2016/0034775 A1 | 2/2016 | Meadow et al. |

FOREIGN PATENT DOCUMENTS

| | | |
|---|---|---|
| CN | 104758292 B | 7/2015 |
| WO | WO 03/020722 A1 | 3/2003 |
| WO | WO 2007/014838 A1 | 2/2007 |
| WO | WO 2008/050096 A1 | 5/2008 |
| WO | 2016210296 A1 | 12/2016 |
| WO | 2018106192 A1 | 6/2018 |

OTHER PUBLICATIONS

Pearce et al., Failure modes in anticancer drug discovery and development, Cancer Drug Design and Discovery Edited by Stephen Neidle, Chapter 18, pp. 424-435 (2008).*
Johnson et al., Relationships between drug activity in NCI preclinical in vitro and in vivo models and early clinical trials, British Journal of Cancer (2001) 64(10): 1424-1431.*
Simone, Oncology: Introduction, Cecil Textbook of Medicine, 20th Edition, vol. 1, pp. 1004-1010, 1996.*
Gura, Systems for identifying New Drugs Are Often Faulty, Cancer Models, Science, vol. 278, No. 5340, pp. 1041-1042, Nov. 1997.*
Acute Leukemia, Merck Manual (Online Edition) 6 pages, pp. 1-6 (2013).*
Voss et al. "Discovery and pharmacological characterization of a novel small molecule inhibitor of phosphatidylinositol-5-phosphate 4-kinase, type II, beta." Biochemical and biophysical research communications 449.3 (2014): 327-331.
Zhang et al. "Identification of tumor-initiating cells in a p53-null mouse model of breast cancer." Cancer research 68.12 (2008): 4674-4682.
Davis et al. "A homogeneous, high-throughput assay for phosphatidylinositol 5-phosphate 4-kinase with a novel, rapid substrate preparation." PLoS One 8.1 (2013): e54127.
Demian et al. "High-throughput, cell-free, liposome-based approach for assessing in vitro activity of lipid kinases." Journal of biomolecular screening 14.7 (2009): 838-844.
Kitagawa et al. "Dual blockade of the lipid kinase PIP4Ks and mitotic pathways leads to cancer-selective lethality." Nature communications 8.1 (2017): 1-13.
Clarke, et al. "The function of phosphatidylinositol 5-phosphate 4-kinase γ (PI5P4Kγ) explored using a specific inhibitor that targets the PI5P-binding site." Biochemical Journal 466.2 (2015): 359-367.
Supplementary Partial European Search Report dated Apr. 22, 2022, issued by the European Patent Office for European Patent Application No. 19847897.6.

* cited by examiner

*Primary Examiner* — Deepak R Rao
(74) *Attorney, Agent, or Firm* — Saul Ewing LLP;
Kathryn Doyle; Domingos J. Silva

(57) ABSTRACT

The present-disclosure relates to the discovery of novel 2-amino-dihydropteridinone compounds and analogues thereof, which are capable of inhibiting phosphatidylinositol phosphate kinases. In certain embodiments, the compounds of the present disclosure can be used to treat p53-null cancer in a subject. In other embodiments, the compounds of the present disclosure can be used to treat metabolic disorders in a subject, including but not limited to type 2 diabetes and/or obesity.

13 Claims, 30 Drawing Sheets
Specification includes a Sequence Listing.

PLK (protein kinase)   PIPK (lipid kinase)

7d  (20nM, 60nM)    7a  (40nM, 30nM)

7b  (140nM, 30nM)   7c  (0.5µM, 1.8µM)

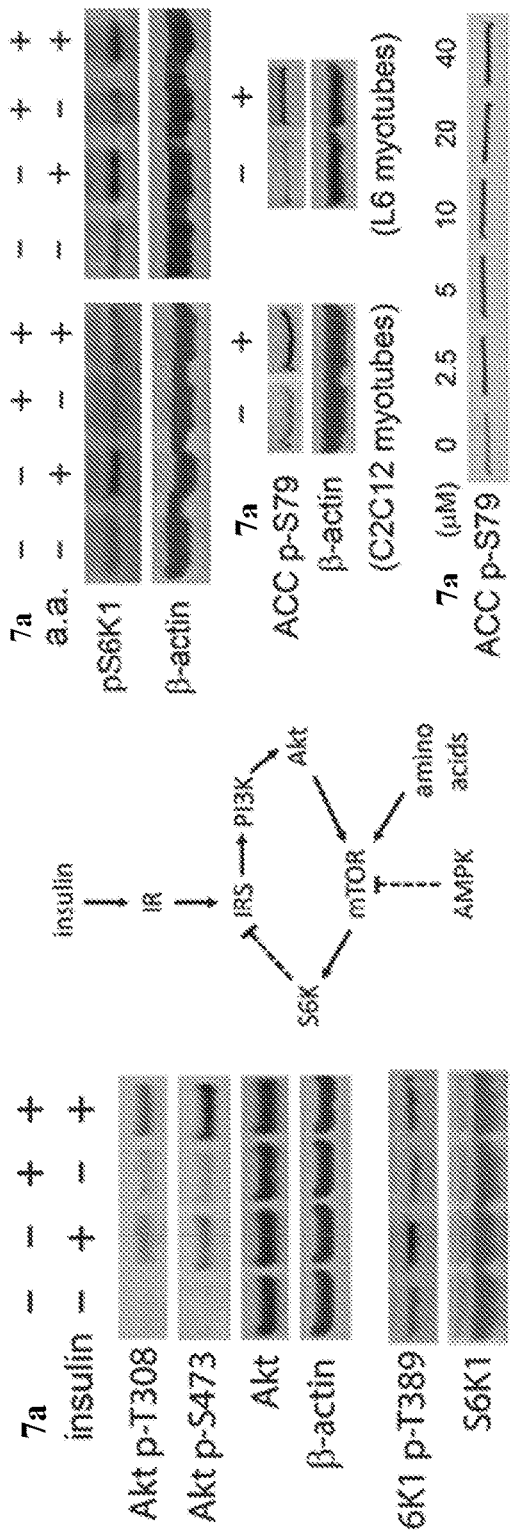
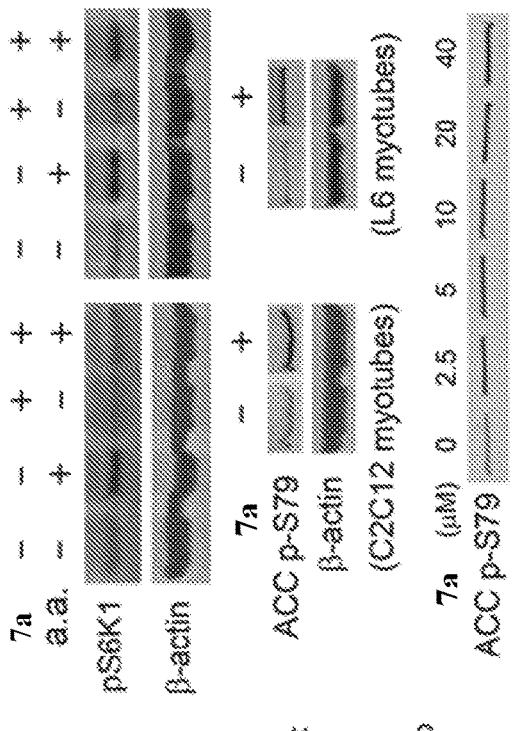
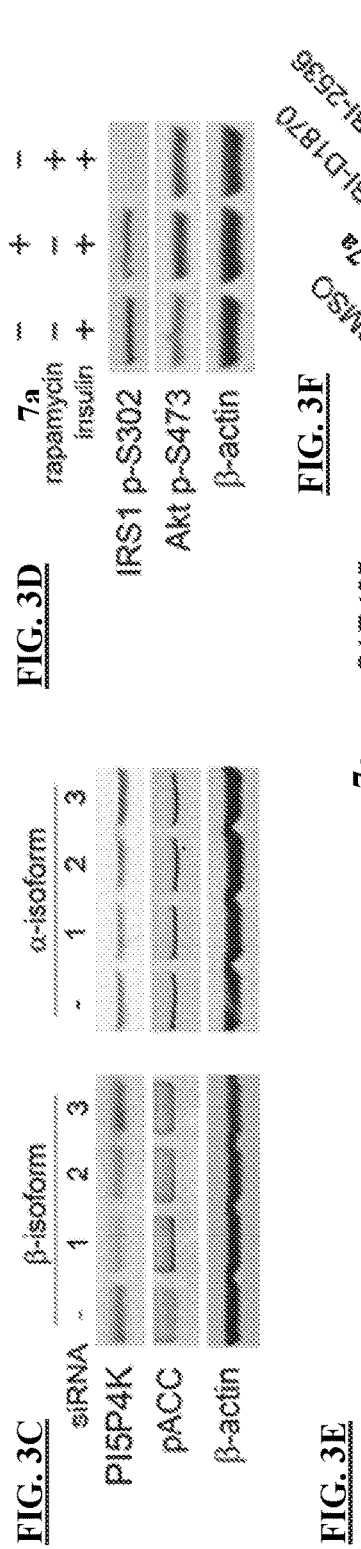
FIG. 3A
FIG. 3B
FIG. 3C
FIG. 3D
FIG. 3E
FIG. 3F

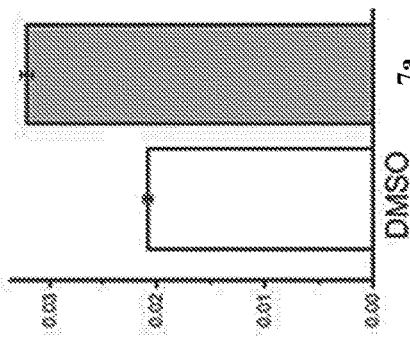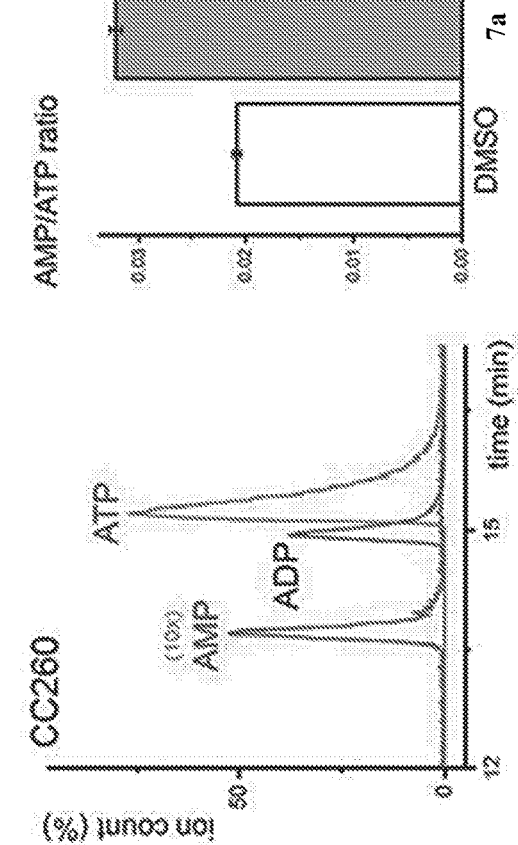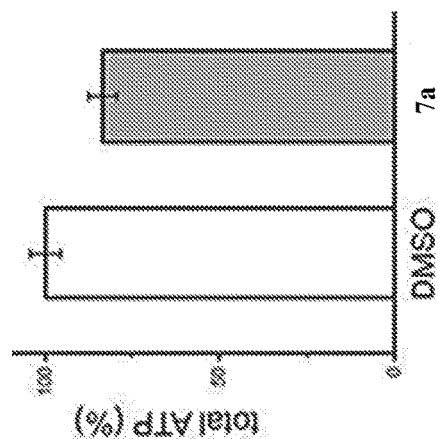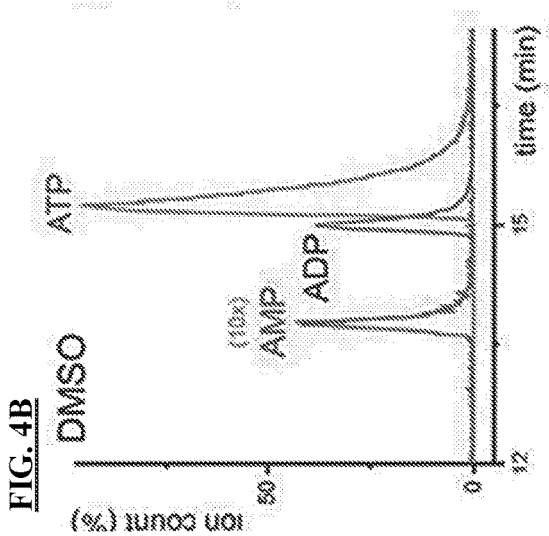
FIG. 4A
FIG. 4B

P I5P4Kβ

[ATP] 60μM

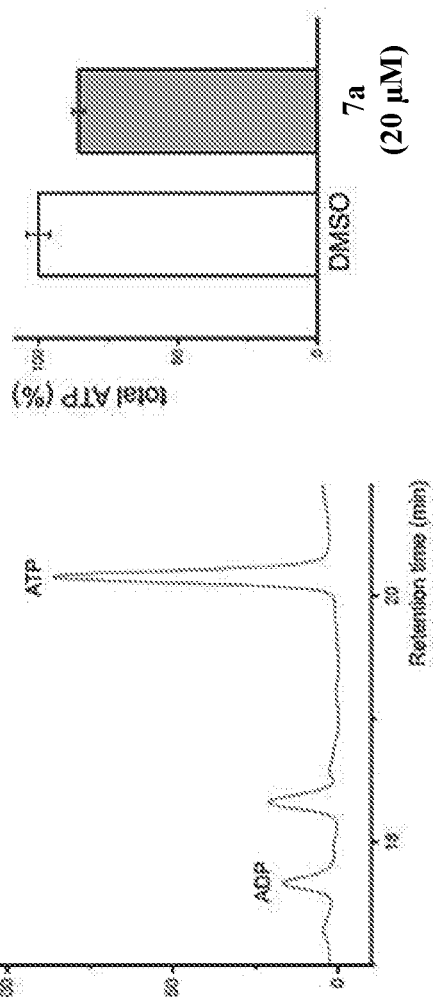
FIG. 15A
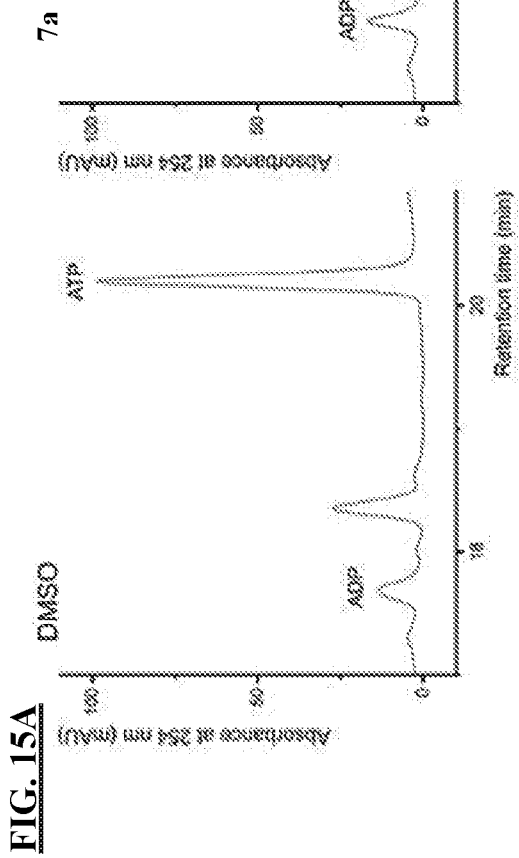
FIG. 15B
FIG. 15C
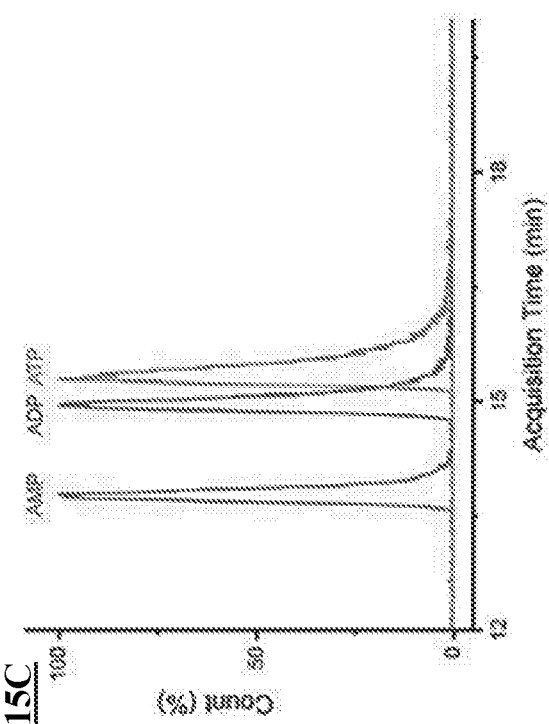
FIG. 15D

SEQUENCE LISTING

```
<160> NUMBER OF SEQ ID NOS: 2

<210> SEQ ID NO 1
<211> LENGTH: 21
<212> TYPE: DNA
<213> ORGANISM: Mus musculus

<400> SEQUENCE: 1
gcaagaucaa gguggacaat t                                              21

<210> SEQ ID NO 2
<211> LENGTH: 21
<212> TYPE: DNA
<213> ORGANISM: Mus musculus

<400> SEQUENCE: 2
gcauuucgug ugccagaaat t                                              21
```

SMALL-MOLECULE PI5P4K ALPHA/BETA INHIBITORS AND METHODS OF TREATMENT USING SAME

CROSS-REFERENCE TO RELATED APPLICATIONS

The present application is a 35 U.S.C. § 371 national phase application from, and claims priority to, PCT International Patent Application No. PCT/US2019/045894, filed Aug. 9, 2019, which claims priority under 35 U.S.C. § 119(e) to U.S. Provisional Patent Application No. 62/717,504, filed Aug. 10, 2018, the contents of which are hereby incorporated by reference herein in their entireties.

STATEMENT REGARDING FEDERALLY SPONSORED RESEARCH OR DEVELOPMENT

This invention was made with government support under GM138722, GM112778, GM101136, and GM122473 awarded by National Institutes of Health. The government has certain rights in the invention.

SEQUENCE LISTING

The instant application contains a Sequence Listing which has been submitted in ASCII format via EFS-Web and is hereby incorporated by reference in its entirety. Said ASCII copy, created on Feb. 8, 2021, is named 047162-7189US1_SequenceListing.txt and is 747 kilobytes in size.

BACKGROUND OF THE INVENTION

Phosphatidylinositol 4,5-bisphosphate, or $PI(4,5)P_2$, is a versatile lipid that is best known for its constitutive function as the major membrane binding site for a wide variety of soluble, mostly cytosolic proteins and some integral membrane proteins, and for its role in signal transduction as the precursor for classic second messengers such as inositol 1,4,5-trisphosphate ($IP_3$), diacylglycerol (DAG), and phosphatidylinositol 3,4,5-trisphosphate ($PIP_3$). The bulk of cellular $PI(4,5)P_2$ is found at the inner leaflet of the plasma membrane, and is synthesized from phosphatidylinositol 4-phosphate, or PI(4)P, by the type 1 phosphatidylinositol phosphate kinase PI4P5K. There is a second synthetic pathway where $PI(4,5)P_2$ can be generated from the much rarer phosphatidylinositol 5-phosphate, or PI(5)P, through the activity of the type 2 phosphatidylinositol phosphate kinase PI5P4K. The type 2 kinase is as abundantly expressed as the type 1 kinase, but functionally less well understood. It has been proposed that PI5P4K may serve to suppress PI(5)P, a lipid second messenger often induced by stress, or is responsible for producing local pools of $PI(4,5)P_2$ at internal membrane compartments such as Golgi and nucleus.

In higher animals, there are three PI5P4K isoforms, α, β and γ, which are encoded by three different genes, PIP4K2A, B and C. The three isoforms differ, at least in vitro, quite significantly in their specific activities: PI5P4Kα is two orders of magnitude more active than PI5P4Kβ, while PI5P4Kγ has very little activity. PI5P4Ks are dimeric proteins, and the possibility that they can form heterodimers may have important functional implications, especially for the lesser active isoforms. PI5P4Kβ is the only isoform that preferentially localizes to the nucleus.

Genetics has implicated PI5P4Kβ in metabolic regulation. Mice with both PIP4K2B genes inactivated manifest hypersensitivity to insulin stimulation and adult males are also leaner. Although this is consistent with the observation that PI(5)P level, which can be manipulated by overexpressing PI5P4K, or a bacterial phosphatase that robustly produces PI(5)P from $PI(4,5)P_2$, correlates positively with PI3K/Akt signaling, the underlying molecular mechanisms remain undefined. Both male and female $PIP4K2B^{-/-}$ mice are mildly growth retarded. Inactivation of the only PI5P4K isoform in Drosophila also produced small and developmentally delayed animals. These phenotypes may be related to suppressed TOR signaling, but the mechanism is unclear since TORC1 is downstream of, and positively regulated by PI3K/Akt. Knocking out the enzymatically more active PI5P4Kα, in contrast, has not been shown to produce any overt metabolic or developmental phenotypes.

Metabolic reprogramming is a hallmark of cancer. Cell transformation is often accompanied by metabolic vulnerabilities imposed by underlying driver mutations. Loss of p53, a tumor suppressor that is mutated in most human cancers, renders cells susceptible to nutrient stress, and to the antidiabetic drug metformin. Although $TP53^{-/-}$ and $PIP4K2B^{-/-}$ mice are themselves viable, combining the two is lethal. Removing three copies of PI5P4K ($PIP4K2A^{-/-}$ $PIP4K2B^{+/-}$) greatly reduces spontaneous tumor formation and cancer-related death in $TP53^{-/-}$ animals. The synthetic lethal interaction between p53 and the lipid kinase in proliferating tumor cells was previously thought to be caused by suppressed glucose metabolism and increased reactive oxygen species (ROS).

Given the interest in the physiological function of this alternative synthetic route for $PI(4,5)P_2$, and the potential of PI5P4K inhibitors in treating type 2 diabetes and cancer, several attempts had been made to identify chemical probes that target various PI5P4K isoforms, but these efforts yielded compounds with limited affinity and unknown selectivity.

Therefore, there remains a need in the art for novel PI5P4K inhibitors that are potent and selective. In certain embodiments, these compounds can inhibit PI5P4Kα/β and modulate energy metabolism, thereby treating cancer and metabolic disorders in subjects in need thereof. The present invention meets these needs.

BRIEF SUMMARY OF THE INVENTION

The invention provides a compound of Formula (IA), or a salt, solvate, enantiomer, diastereoisomer, or tautomer thereof:

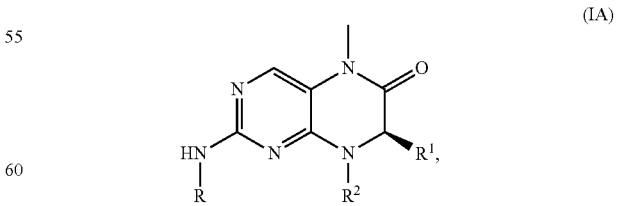

(IA)

wherein R, $R^1$, and $R^2$ are defined elsewhere herein.

The invention provides a compound of Formula (IIA), or a salt, solvate, enantiomer, diastereoisomer, or tautomer thereof:

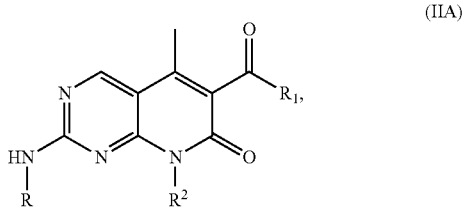

(IIA)

wherein R, $R^1$, $R^2$, and $R^3$ are defined elsewhere herein.

The invention further provides a pharmaceutical composition comprising at least one compound of the invention.

The invention further provides a method of treating a p53-null cancer in a subject in need thereof, the method comprising administering to the subject a therapeutically effective amount of at least one compound of the invention.

The invention further provides a method of treating at least one metabolic disorder in a subject in need thereof, the method comprising administering to the subject a therapeutically effective amount of at least one compound of the invention.

BRIEF DESCRIPTION OF THE DRAWINGS

The following detailed description of specific embodiments of the invention will be better understood when read in conjunction with the appended drawings. For the purpose of illustrating the invention, specific embodiments are shown in the drawings. It should be understood, however, that the invention is not limited to the precise arrangements and instrumentalities of the embodiments shown in the drawings.

FIG. 1A shows the chemical structures of the lead compounds, and their $K_i$s for PI5P4Kα (shown in the parentheses). FIG. 1B is a set of Michaelis-Menten curves obtained at different BI-D1870 concentrations based on ADP-Glo™ measurement of relative luminescence unit, or RLU (left panel). BI-D1870 displaces a bound fluorescent ATP analog from PI5P4Kα, which provides an independent measurement of its $K_d$ (RFU, relative fluorescence unit; right panel). FIG. 1C is a difference Fourier analysis confirming inhibitor binding to the ATP binding pocket of PI5P4Kα. Fo-Fc maps, contoured at 3σ, are shown in green. Red spheres represent water. The cyclohexane piperazine side chain of volasertib is largely disordered. FIG. 1D is a diagram showing key binding interactions exemplified by the crystal structure of PI5P4Kα in complex with BI-D1870. Hydrogen bonds are shown as dashed lines with distance labeled (italic). The numbering system for pteridine is also shown.

FIG. 2A is a diagram comparing the binding of BI-2536 to polo-like kinase 1 (pdb: 2RKU) and PI5P4Kα. The kinked αC helix as well as the absence of a conserved salt bridge create a pocket in the lipid kinase adjacent to the C7-side chain of the bound inhibitor (indicated by the red asterisk). FIG. 2B is a set of chemical structures of the compounds of the invention. The $K_i$ values for PI5P4Kα and PI5P4Kβ are shown in the parentheses. FIG. 2C is a set of concentration-inhibition curves of 7a (lower curve) and BI-D1870 (upper curve) for PI5P4Kα and PI5P4Kβ based on measurements of $^{32}$P-labelled PI(4,5)P$_2$ resolved by TLC. ATP concentration was fixed at 20 μM in both experiments ($K_{m,ATP}$ for PI5P4Kα is 13 μM; $K_{m,ATP}$ for PI5P4Kβ is 17 μM). FIG. 2D is a difference Fourier analysis confirming the binding of 7a to the active site of PI5P4Kβ. Fo-Fc map, shown in green, was contoured at 36. Red spheres represent water.

FIGS. 3A-3F are graphs and diagraphs showing that PI5P4Kβ inhibition activated AMPK in myotubes. FIG. 3A is an image of a Western blot analysis showing that 7a enhanced insulin-induced Akt phosphorylation at both Thr-308 and Ser-473 but suppressed S6K phosphorylation by mTORC1. FIG. 3B is a scheme showing that mTORC1 receives major inputs from growth factors through the PI3K/Akt pathway, amino acids, and AMPK. IR, insulin receptor. In both C2Cl2 and L6 myotubes, 7a did not prevent amino acids from activating mTORC1. 7a activated AMPK in a dose-dependent manner. FIG. 3C is a set of Western blots showing that siRNA knockdown of PI5P4Kβ, but not PI5P4Kα, increased ACC phosphorylation by AMPK. FIG. 3D is a set of Western blots showing that enhanced Akt phosphorylation correlated with reduced IRS1 phosphorylation at Ser-302, caused by either 7a or rapamycin treatment. FIG. 3E is a set of Western blots showing that PI3Kα inhibitor GDC-0941 eliminated insulin-induced Akt phosphorylation at Ser-473. Vps34 inhibitor SAR405 prevented mTORC1 activation by amino acids. 7a demonstrated neither of these effects. Although 7a reduced S6K phosphorylation in myotubes, it did not inhibit mTOR/FRAP1 in vitro. FIG. 3F is a set of Western blots showing that compounds BI-D1870 and BI-2536, and compound 7c, did not increase ACC phosphorylation, whereas 7d and 7a, equipotent toward PI5P4Kα and PI5P4Kβ, and 7b, more specific for PI5P4Kβ, activated AMPK.

FIGS. 4A-4D are graphs showing that PI5P4Kβ inhibition perturbs cellular energy metabolism. FIG. 4A is a graph comparing total cellular ATP measured using a luminescent ATP detection assay kit (Abcam) and normalized against total protein concentration for cells in the presence of 7a or DMSO control. FIG. 4B is a set of graphs comparing levels of intracellular AMP, ADP and ATP measured by LC-MS/MS for cells in the presence of 7a or DMSO control. The elution profiles of the control and compound-treated samples are scaled according to total ATP determined by the luminescent assay. The AMP peak is shown as ten times the actual height for easier visualization. AMP/ATP ratio was measured in triplicate. FIG. 4C is a graph comparing uptake of $^{13}$C-labeled 2-DG into L6 myotubes after overnight treatment with 20 μM 7a or 1 mM metformin. FIG. 4D is a pair of graphs showing glucose and lactate concentrations in the media 48 hours after being treated with DMSO, 7a and metformin. Glucose concentrations were reduced by 7.8 mM, 10.3 mM and 10.6 mM, respectively. Lactate accumulated to 5.3 mM, 7.7 mM and 8.6 mM. The molar fractions of glucose used for lactate fermentation were 34%, 38% and 41%.

FIG. 5A is a graph showing that 7a (20 μM) inhibited the proliferation of BT474 cells in the top panel. The dose-response curve is shown in the lower panel. FIG. 5B is a set of Western blots showing that 7a (0, 10 and 20 μM) caused AMPK activation and mTORC1 inhibition. FIG. 5C is a graph and Western blot showing that AMPK activation was abrogated in BT474 cells expressing a refractory PI5P4Kβ double mutant. The left panel is a graph comparing the in vitro activities of wildtype and mutant PI5P4Kβ at different inhibitor concentrations. FIG.

5D is a set of Western blots showing that siRNA knockdowns of PI5P4Kβ, and to a lesser extent PI5P4Kα, caused AMPK activation. FIG. 5E is a graph showing that 7a treatment increased AMP/ATP ratio. FIG. 5F is a set of graphs showing that after 7a treatment (shaded bars), the cells failed to respond to serum that normally stimulates aerobic glycolysis. Without serum or compound, 86% of the consumed glucose was converted to lactate. Under other conditions, nearly all the glucose (within the error range of the measurements) was used for lactate fermentation. FIG. 5G shows cell cycle analysis by FACS and Western blot for cell cycle inhibitors p21 and p27. FIG. 5H is a graph showing that 7a treatment only transiently arrested cell cycle progression. After a 24-hour washout period, the cells resumed growth at a similar rate as untreated cells. FIG. 5I is a set of Western blots and a graph showing that the energy stress induced by PI5P4Kα/β inhibition could be overcome in the presence of serum and a functional p53 when BT474 cells were cultured at 32° C. (MCF7 cells have wildtype p53). At 32° C., the effect of the compound on cell growth was also reduced.

FIG. 6A is a Lineweaver-Burk plot of the enzyme kinetic data shown in FIG. 1B. FIG. 6B is a set of concentration-inhibition curves for the prior art compounds based on ADP-Glo™ assay. Experiments were performed in triplicate at a constant ATP concentration of 10 μM. For PI5P4Kα, $K_{m,\ ATP}$ was determined to be ~13 μM based on data shown in FIG. 1B.

FIG. 7A is a ribbon diagram of the PI5P4Kα dimer with the protomers colored green (left) and blue (right). The specificity loops are highlighted in yellow (arrow labeled). Four sulfate ions, shown as space filling models, are found near the 2-fold symmetry axis on a flat surface facing toward the membrane, which mark possible binding sites for the acidic head groups of phospholipids. FIG. 7B is the Cα trace of a single PI5P4Kα protomer. The difference map, contoured at 2.56 and shown in green, indicates the position of the specificity loop. FIG. 7C is a model showing that Glu-150 and Glu-154 form multiple hydrogen bonds with the amino-terminal region of the specificity loop, stabilizing the sharp turn from the β-strand (β12) to the helix. Without intending to be limited to any particular theory, this structural feature is likely unique to PI5P4Ks since Glu-150 and Glu-154 are highly conserved only in type 2 kinases. The turn may explain PI5P4Ks' substrate specificity because it is incompatible with the binding mode of PI(4)P, the substrate for type 1 kinases. Although PI(4)P is much more abundant in a cell, type 2 kinases cannot phosphorylate them. FIGS. 7D-7E show that the orientation of the helix, likely influenced by crystal packing, is slightly different between the two apo structures (2FoFc maps contoured at 1σ).

FIG. 8A is a 2FoFc map around the bound ATP analog and Mn(II) ions (contoured at IG). FIG. 8B is a diagram showing the details of the binding interactions between AMP-PNP/Mn(II)$_2$ and PI5P4Kα. Hydrogen bonds are shown as dashed lines. Red spheres represent water. Blue spheres represent Mn(II) ions. FIGS. 8C-8D are diagrams showing the differences between the PI5P4Kα structure and a published PI5P4Kβ:AMP-PNP structure. Without intending to be limited to any particular theory, the differences in the structures may be related to the fact that the latter does not contain any metal ions (pdb: 3X03) (Sumita, K. et al., Mol Cell 61, 187-98 (2016)). Like protein kinases, divalent metal ions are required for lipid kinase activity. In PI5P4Kα, Asp-359 from the conserved "IID" motif serves a similar function of metal binding as the aspartate from the "DFG" motif of protein kinases. It becomes also clear from the high-resolution structure that there is no salt bridge, or water-mediated hydrogen bonds, between Lys-145 and Asp-151, a significant difference from protein kinase. In one of the AMP-PNP structures, the Gly-rich loop is partially visible. However, the loop does not appear to make extensive contacts with β- and γ-phosphates of the bound ATP analog, which is also different from its counterpart in protein kinases.

FIG. 10A is a diagram detailing the binding of BI-2536 to protein kinase Plk1 (pdb: 2RKU). The 6-carbonyl oxygen of the inhibitor engages in water-mediated hydrogen bonds with Lys-82, as well as backbone amide groups of Asp-194 and Phe-195. The salt bridge between Lys-82 and Glu-101 is present in all protein kinases. FIG. 10B is a surface representation of the inhibitor binding pocket in Plk1. FIG. 10C is a surface representation of the inhibitor binding pocket in PI5P4Kα. The red asterisk marks the entry point to the hydrophobic pocket that is present only in this family of lipid kinases.

FIG. 11A shows a mixture of N, O-dimethylated derivatives of 7a and (S)-7a (90:10 hexanes:isopropanol, 1 mL/min, 254 nm). FIG. 11B shows the N,O-Dimethylated derivative of 7a ((R)-7a). FIG. 11C shows the N,O-Dimethylated derivative of (S)-7a.

FIG. 12A is a set of representative autoradiographs of the TLC plates. Based on the titration, the $K_{m,\ ATP}$ values for PI5P4Kα and PI5P4Kβ were determined to be 13 μM and 17 μM, respectively. FIG. 12B is a set of representative autoradiographs comparing concentration effect relationship of 7a with that of BI-D1870. In this experiment, ATP concentration was fixed at 20 μM. FIGS. 12C-12D are concentration effect curves obtained at 20 μM ATP. The $K_i$ values for 7d, 7a and 7b against PI5P4Kβ were obtained from titrations at a higher ATP concentration (60 μM), which shifts $IC_{50}$ to the right. The concentration of PI5P4Kβ in the assay mixture was about 40 nM, which was not negligible at low compound concentrations. All experiments were performed in triplicate.

FIG. 13A shows that 7a caused little conformational change in the kinase, except the Gly-rich loop (apo, black; complex, light orange). Superimposed Cα traces are shown as a cross-eye stereogram. The inhibitor is shown as orange sticks. FIG. 13B is a diagram showing the details of 7a binding to the lipid kinase. Hydrogen bonds are shown as red dashed lines. FIGS. 13C-13D are 2FoFc maps, contoured at 1σ, revealing differences in the conformation of the G-loop between apo and complex structures. The inhibitor is colored in orange.

FIGS. 14A-14C are graphs showing the selectivity profile of 7a. FIG. 14A is a set of concentration inhibition curves of 7a and compounds BI-2536 and BI-D1870 for Plk1- and RSK2-mediated kinase reactions. In both titrations, the ATP concentration was fixed at 50 μM. The assay kits for Plk1 and RSK2 were obtained from Promega (Madison, Wis.), which use ADP-Glo™ for activity detection. FIG. 14B is a graph showing kinase activity of 7a tested against 396 human protein kinases at a compound concentration of 0.5 μM and ATP concentration of 20 μM using the HotSpot™ radioisotope filter binding assay. Plk1 and RSK2 were among the kinases examined, and their extent of inhibition (Plk1 activity remaining 97%; RSK2, 83%) is consistent with the results shown in FIG. 14A that cover a range of compound concentrations. Calculated RSK2 activity at 0.5 μM 7a and 20 μM ATP was 79% of that of DMSO control. FIG. 14C shows that 7a did not inhibit PI4P5Kα but showed modest inhibition of PIKfyve. Profiling a panel of 14 lipid kinases using ADP-Glo™ for detecting lipid kinase activities, showed that PI3Kγ and PI3Kδ were also inhibited by 7a (compound 0.5 μM, ATP 10 μM). The panel included PI4P5Kα and another type 1 kinase PI4P5Kγ, neither of which was inhibited (PI4P5Kα 95% activity remaining; PI4P5Kγ 98%).

FIGS. 15A-15D are graphs and a table measuring intracellular adenine nucleotide concentrations. FIG. 15A is a HPLC elution profiles of acid extracts of cells treated with DMSO or 7a. FIG. 15B is a graph quantifying the areas under the ATP peak (measured in triplicate). FIG. 15C is an LC-MS/MS spectrum of an equimolar mixture of AMP, ADP and ATP standards. FIG. 15D is a table summarizing the fragmentation of AMP or ADP generated $PO_3$ (theoretical M.W. 79.0 Da), and the fragmentation of ATP yielded a $P_2O_6$ ion (theoretical M.W. 157.9 Da).

FIG. 16A is a graph and Western blot showing that 7a (20 μM) treatment increased ROS and p38 phosphorylation. NAC, N-acetyl cysteine. FIG. 16B is a graph showing that prolonged treatment with 7a caused permanent loss of cell proliferation. FIG. 16C is a scheme of a model depicting the role of p53 in restoring energy homeostasis upon lipid kinase inhibition within the context of cell cycle progression. FIG. 16D is a set of Western blots showing that the restoration of p53 function by culturing BT474 cells at 32° C. does not correct AMPK activation induced by metformin or phenformin.

FIG. 17B: Growth of p53(+/+) cells can be completely inhibited by 4 μM erlotinib, an EGFR inhibitor (top left: dose response curve; top right: growth curves in the presence of 4 μM erlotinib). In contrast, p53(−/−) cells maintain a residual amount of growth even when EGFR is completed inhibited. The residual growth is eliminated by 10 μM 7a.

DETAILED DESCRIPTION OF THE INVENTION

Figure 1A:
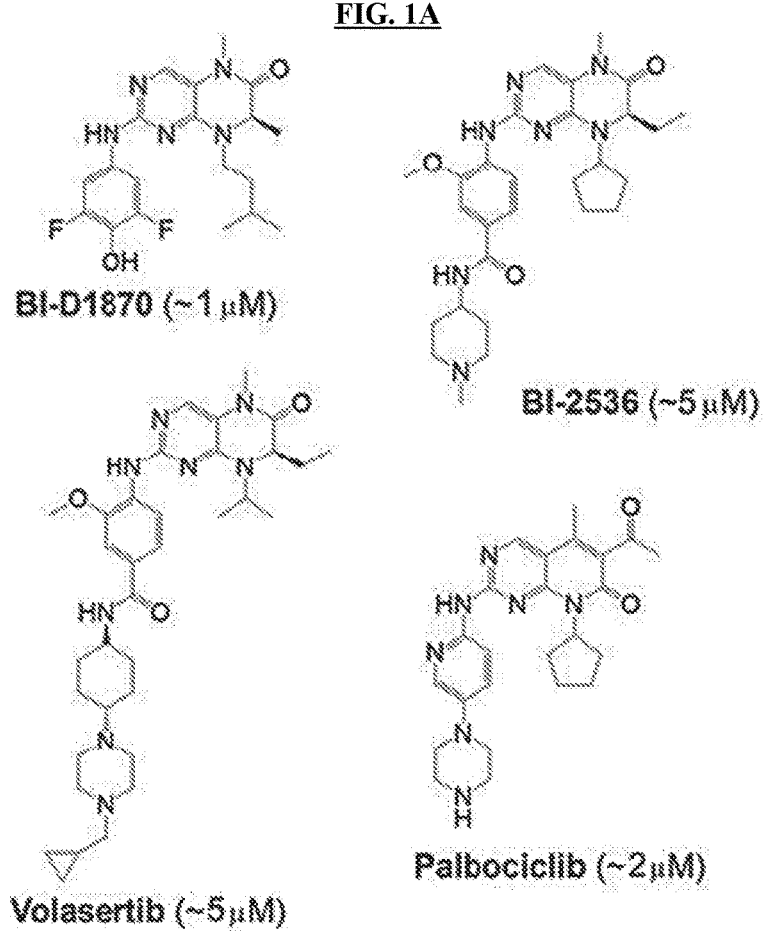
FIGS. 1A-1D are diagrams and graphs showing prior art compounds having a 2-amino-dihydropteridinone core (or a related core as in palbociclib) that were found to have weak PI5P4K inhibitory properties.

The present invention relates to the discovery of 2-amino-dihydropteridinone compounds, and analogues thereof, that are capable of inhibiting PI5P4Kα and PI5P4Kβ. In certain embodiments, the compounds of the invention can be used to treat p53-null cancer in a subject. In other embodiments, the compounds of the invention selectively kill p53-null cancer cells over non-p53-null cancer cells. In yet other embodiments, the compounds of the invention can be used to treat metabolic disorders in a subject, including but not limited to type 2 diabetes and/or obesity.

Compounds

In one aspect, the invention provides a 2-amino-dihydropteridinone compound, or a salt, solvate, enantiomer, diastereoisomer, or tautomer thereof, which is capable of inhibiting PI5P4Kα and PI5P4Kβ.

In certain embodiments, the invention provides a compound of Formula (IA) or a salt, solvate, enantiomer, diastereoisomer, or tautomer thereof:

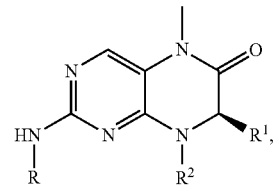

(IA)

wherein:
R is

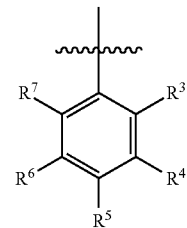

or heteroaryl, wherein the heteroaryl is optionally substituted with at least one selected from the group consisting of $C_1$-$C_6$ alkyl, $C_3$-$C_8$ cycloalkyl, $C_1$-$C_6$ alkoxy, $C_3$-$C_8$ cycloalkoxy, halogen, —OH, —C(=O)OH, —C(=O)$C_1$-$C_6$ alkyl, —C(=O)$C_3$-$C_8$ cycloalkyl, thiol, $C_1$-$C_6$ thioalkoxy, and —NR'R', wherein each occurrence of R' is independently H or $C_1$-$C_6$ alkyl or the two R' bound to the N combine to form 3-7 membered heterocyclyl;

$R^1$ is selected from the group consisting of $C_1$-$C_6$ alkyl (such as, but not limited to, —CH(CH$_3$)$_2$), $C_3$-$C_8$ cycloalkyl, $C_1$-$C_6$ heteroalkyl, $C_3$-$C_8$ heterocycloalkyl, $C_2$-$C_6$ alkenyl, and $C_2$-$C_6$ alkynyl;

wherein in $R^1$ each occurrence of alkyl, cycloalkyl, heteroalkyl, heterocycloalkyl, alkenyl, or alkynyl is optionally substituted with at least one substituent selected from the group consisting of $C_1$-$C_6$ alkyl, $C_3$-$C_8$ cycloalkyl, $C_1$-$C_6$ alkoxy, $C_3$-$C_8$ cycloalkoxy, halogen, —OH, thiol, $C_1$-$C_6$ thioalkoxy, phenyl, heteroaryl, heterocyclyl, and —NR"R", wherein each occurrence of R' is independently H or $C_1$-$C_6$ alkyl or the two R" bound to the N combine to form 3-7 membered heterocyclyl;

$R^2$ is selected from the group consisting of $C_1$-$C_6$ alkyl, $C_3$-$C_8$ cycloalkyl, $C_1$-$C_6$ heteroalkyl, $C_3$-$C_8$ heterocycloalkyl, $C_2$-$C_6$ alkenyl, and $C_2$-$C_6$ alkynyl;

wherein in $R^2$ each occurrence of alkyl, cycloalkyl, heteroalkyl, heterocycloalkyl, alkenyl, or alkynyl is optionally substituted with at least one substituent selected from the group consisting of $C_1$-$C_6$ alkyl, $C_3$-$C_8$ cycloalkyl, $C_1$-$C_6$ alkoxy, $C_3$-$C_8$ cycloalkoxy, halogen, —OH, thiol, $C_1$-$C_6$ thioalkoxy, phenyl, heteroaryl, heterocyclyl, and —NR'''R''', wherein each occurrence of R' is independently H or $C_1$-$C_6$ alkyl or the two R''' bound to the N combine to form 3-7 membered heterocyclyl;

$R^3$ is selected from the group consisting of H, halogen, $C_1$-$C_6$ alkyl, and $C_3$-$C_8$ cycloalkyl;

$R^4$ is selected from the group consisting of H, halogen, $C_1$-$C_6$ alkyl, $C_3$-$C_8$ cycloalkyl, —OH, —C(=O)OH, —C(=O)$C_1$-$C_6$ alkyl, and —C(=O)$C_3$-$C_8$ cycloalkyl;

$R^5$ is selected from the group consisting of H, —OH, —C(=O)OH, —C(=O)$C_1$-$C_6$ alkyl, and —C(=O)$C_3$-$C_8$ cycloalkyl;

$R^6$ is selected from the group consisting of H, halogen, $C_1$-$C_6$ alkyl, $C_3$-$C_8$ cycloalkyl, —OH, —C(=O)OH, —C(=O)$C_1$-$C_6$ alkyl, and —C(=O)$C_3$-$C_8$ cycloalkyl; and $R^7$ is selected from the group consisting of H, halogen, $C_1$-$C_6$ alkyl, and $C_3$-$C_8$ cycloalkyl.

In certain embodiments, the invention provides a compound of Formula (IB) or a salt, solvate, enantiomer, diastereoisomer, or tautomer thereof:

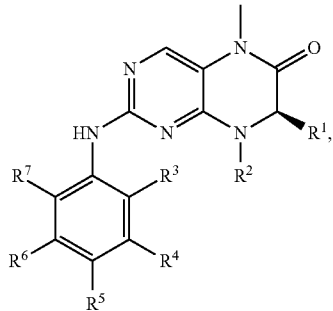

(IB)

wherein:

$R^1$ is selected from the group consisting of $C_1$-$C_6$ alkyl (such as, but not limited to, —CH(CH$_3$)$_2$, $C_3$-$C_8$ cycloalkyl, C1-$C_6$ heteroalkyl, $C_3$-$C_8$ heterocycloalkyl, $C_2$-$C_6$ alkenyl, and $C_2$-$C_6$ alkynyl;

wherein in $R^1$ each occurrence of alkyl, cycloalkyl, heteroalkyl, heterocycloalkyl, alkenyl, or alkynyl is optionally substituted with at least one substituent selected from the group consisting of $C_1$-$C_6$ alkyl, $C_3$-$C_8$ cycloalkyl, $C_1$-$C_6$ alkoxy, $C_3$-$C_8$ cycloalkoxy, halogen, —OH, thiol, $C_1$-$C_6$ thioalkoxy, phenyl, heteroaryl, heterocyclyl, and —NR"R", wherein each occurrence of R' is independently H or $C_1$-$C_6$ alkyl or the two R" bound to the N combine to form 3-7 membered heterocyclyl;

$R^2$ is selected from the group consisting of $C_1$-$C_6$ alkyl, $C_3$-$C_8$ cycloalkyl, $C_1$-$C_6$ heteroalkyl, $C_3$-$C_8$ heterocycloalkyl, $C_2$-$C_6$ alkenyl, and $C_2$-$C_6$ alkynyl;

wherein in $R^2$ each occurrence of alkyl, cycloalkyl, heteroalkyl, heterocycloalkyl, alkenyl, or alkynyl is optionally substituted with at least one substituent selected from the group consisting of $C_1$-$C_6$ alkyl, $C_3$-$C_8$ cycloalkyl, $C_1$-$C_6$ alkoxy, $C_3$-$C_8$ cycloalkoxy, halogen, —OH, thiol, $C_1$-$C_6$ thioalkoxy, phenyl, heteroaryl, heterocyclyl, and —NR'''R''', wherein each occurrence of R' is independently H or $C_1$-$C_6$ alkyl or the two R''' bound to the N combine to form 3-7 membered heterocyclyl;

$R^3$ is selected from the group consisting of H, halogen, $C_1$-$C_6$ alkyl, and $C_3$-$C_8$ cycloalkyl;

$R^4$ is selected from the group consisting of H, halogen, $C_1$-$C_6$ alkyl, $C_3$-$C_8$ cycloalkyl, —OH, —C(=O)OH, —C(=O)$C_1$-$C_6$ alkyl, and —C(=O)$C_3$-$C_8$ cycloalkyl;

$R^5$ is selected from the group consisting of H, —OH, —C(=O)OH, —C(=O)$C_1$-$C_6$ alkyl, and —C(=O)$C_3$-$C_8$ cycloalkyl;

$R^6$ is selected from the group consisting of H, halogen, $C_1$-$C_6$ alkyl, $C_3$-$C_8$ cycloalkyl, —OH, —C(=O)OH, —C(=O)$C_1$-$C_6$ alkyl, and —C(=O)$C_3$-$C_8$ cycloalkyl; and $R^7$ is selected from the group consisting of H, halogen, $C_1$-$C_6$ alkyl, and $C_3$-$C_8$ cycloalkyl.

In certain embodiments, R is heteroaryl selected from the group consisting of 1H-benzo[d][1,2,3]triazolyl, triazolyl, thiazolyl, oxazolyl, isooxazolyl, oxadiazolyl, thiodiazolyl, pyridinyl, pyrimidinyl, triazinyl, pyrazinyl, thiophenyl, benzotriazolyl, benzamidazolyl, indolyl, indazolyl, pyrrolyl, and pyrazolyl.

In certain embodiments, the heterocyclyl is aziridinyl, azetidinyl, pyrrolidinyl, piperazinyl, or morpholinyl.

In certain embodiments, $R^1$ is $C_1$-$C_3$ alkyl. In other embodiments, $R^1$ is $C_4$-$C_6$ alkyl. In yet other embodiments, $R^1$ is methyl. In yet other embodiments, $R^1$ is ethyl. In yet other embodiments, $R^1$ is $C_3$ alkyl. In yet other embodiments, $R^1$ is $C_4$ alkyl. In yet other embodiments, $R^1$ is $C_5$ alkyl. In yet other embodiments, $R^1$ is $C_6$ alkyl.

In certain embodiments, $R^1$ is isopropyl. In certain embodiments, $R^1$ is isobutyl. In certain embodiments, $R^1$ is sec-butyl. In certain embodiments, $R^1$ is tert-butyl. In certain embodiments, $R^1$ is cyclopentylmethyl. In certain embodiments, $R^1$ is cyclohexylmethyl.

In certain embodiments, $R^1$ is a substituent of structure:

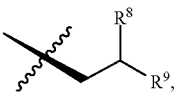

wherein: $R^8$ is selected from the group consisting of $C_1$-$C_6$ alkyl, $C_3$-$C_8$ cycloalkyl, halogen, thiol, $C_1$-$C_6$ thioalkoxy, —OH, $C_1$-$C_6$ alkoxy, and —NR"R"; and $R^9$ is selected from the group consisting of H, $C_1$-$C_6$ alkyl, $C_3$-$C_8$ cycloalkyl, halogen, thiol, $C_1$-$C_6$ thioalkoxy, —OH, $C_1$-$C_6$ alkoxy, and —NR"R", wherein each occurrence of R" is independently H or $C_1$-$C_6$ alkyl.

In certain embodiments, if $R^8$ is methyl, $R^9$ is not H.

In certain embodiments, if $R^9$ is H, $R^8$ is not methyl.

In certain embodiments, $R^2$ is cyclopentyl. In certain embodiments, $R^2$ is cyclohexyl.

In certain embodiments, $R^4$ and $R^6$ are independently selected from the group consisting of F, Cl, Br and I. In other embodiments, $R^4$ and $R^6$ are both Cl.

In certain embodiments, $R^5$ is OH.

In certain embodiments, at least one of $R^4$, $R^5$, and $R^6$ is selected from the group consisting of —OH, —C(=O)OH, —C(=O)$C_1$-$C_6$ alkyl, and —C(=O)$C_3$-$C_8$ cycloalkyl. In certain embodiments, at least one of $R^4$, $R^5$, and $R^6$ is —C(=O)OH. In certain embodiments, at least one of $R^4$, $R^5$, and $R^6$ is —C(=O)$C_1$-$C_6$ alkyl. In certain embodiments, at least one of $R^4$, $R^5$, and $R^6$ is —C(=O)$C_3$-$C_8$ cycloalkyl.

In certain embodiments, R in (IA) is heteroaryl with an acidic group of pKa<8. Non-limiting examples of such heteroaryl groups include benzotriazole, triazole, and tetrazole, and so forth. In certain embodiments, R in (IA) is heteroaryl substituted with at least one of —OH, —C(=O)OH, —C(=O)$C_1$-$C_6$ alkyl, and —C(=O)$C_3$-$C_8$ cycloalkyl. In certain embodiments, R in (IA) is heteroaryl substituted with —C(=O)OH. In certain embodiments, R in (IA) is heteroaryl substituted with —C(=O)$C_1$-$C_6$ alkyl. In certain embodiments, In other embodiments, R in (IA) is heteroaryl substituted with —C(=O)$C_3$-$C_8$ cycloalkyl.

In certain embodiments, the compound of the invention is selected from the group consisting of:

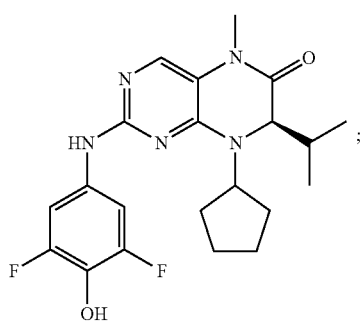

(R)-8-cyclopentyl-2-((3,5-difluoro-4-hydroxyphenyl)amino)-7-isopropyl-5-methyl-7,8-dihydropteridin-6(5H)-one

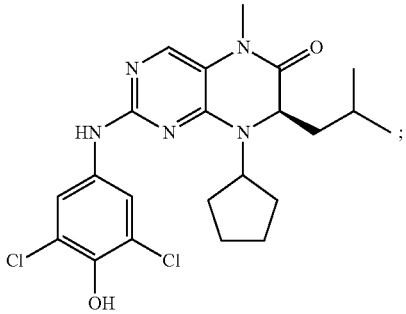

(R)-8-cyclopentyl-2-((3,5-dichloro-4-hydroxyphenyl)amino)-7-isobutyl-5-methyl-7,8-dihydropteridin-6(5H)-one -continued

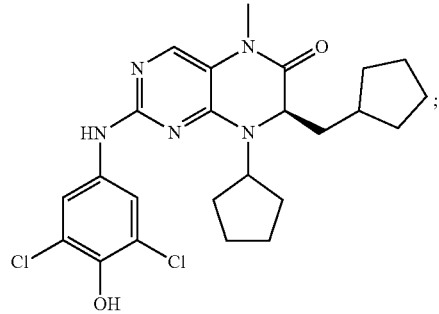

(R)-8-cyclopentyl-7-(cyclopentylmethyl)-2-((3,5-dichloro-4-hydroxyphenyl)amino)-5-methyl-7,8-dihydropteridin-6(5H)-one

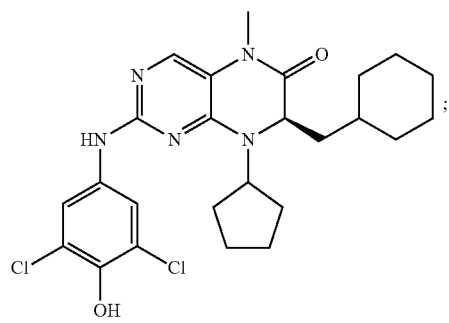

(R)-7-cyclohexylmethyl)-8-cyclopentyl-2-((3,5-dichloro-4-hydroxyphenyl)amino)-5-methyl-7,8-dihydropteridin-6(5H)-one

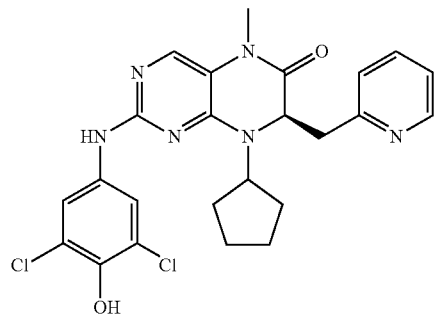

(R)-8-cyclopentyl-2-((3,5-dichloro-4-hydroxyphenyl)amino)-7-(pyridine-2-ylmethyl)-5-methyl-7,8-dihydropteridin-6(5H)-one;

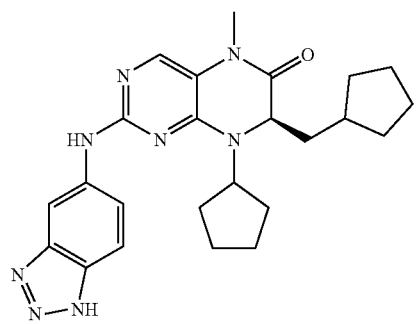

(R)-2-((1H-benzo[d][1,2,3]triazol-5-yl)amino-8-cyclopentyl-7-(cyclopentylmethyl)-5-methyl-7,8-dihydropteridin-6(5H)-one;

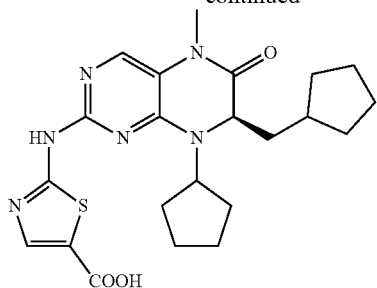

(R)-2-((8-cyclopentyl-7-cyclopentylmethyl)-5-methyl-6-oxo-5,6,7,8-tetrahydropteridin-2-yl)amino)thiazole-5-carboxylic acid;

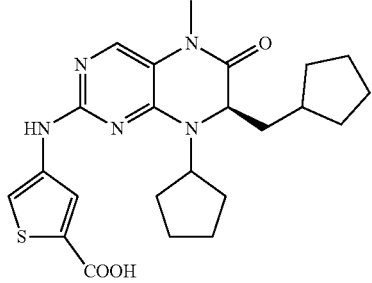

(R)-4-((8-cyclopentyl-7-cyclopentylmethyl)-5-methyl-6-oxo-5,6,7,8-tetrahydropteridin-2-yl)amino)thiophene-2-carboxylic acid;

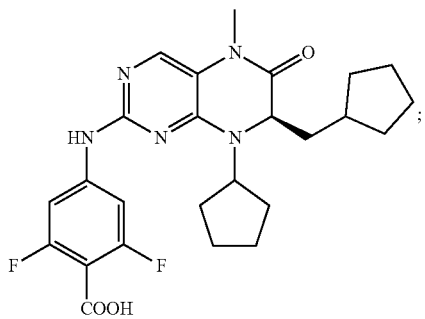

(R)-4-((8-cyclopentyl-7-(cyclopentylmethyl)-5-methyl-6-oxo-5,6,7,8-tetrahydropteridin-2-yl)amino)-2,6-difluorobenzoic acid

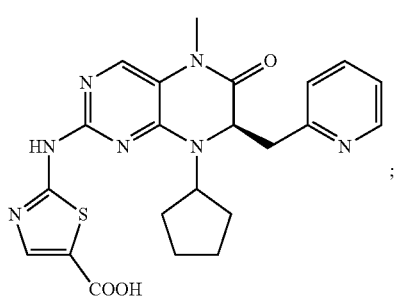

(R)-2-((8-cyclopentyl-5-methyl-6-oxo-7-(pyridin-2-ylmethyl)-5,6,7,8-tetrahydropteridin-2-yl)amino)thiazole-5-carboxylic acid

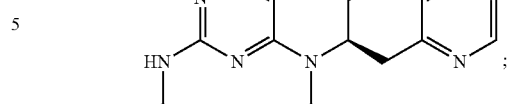

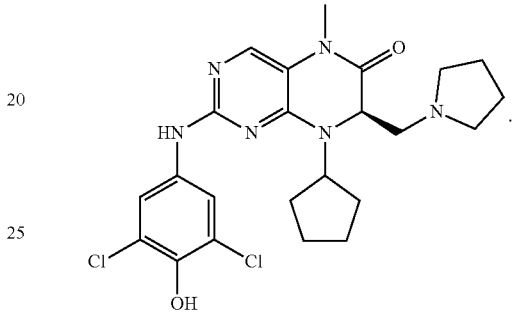

(R)-2-((1H-benzo[d][1,2,3]triazol-5-yl)amino)-8-cyclopentyl-5-methyl-7-(pyridin-2-ylmethyl)-7,8-dihydropteridin-6(5H)-one

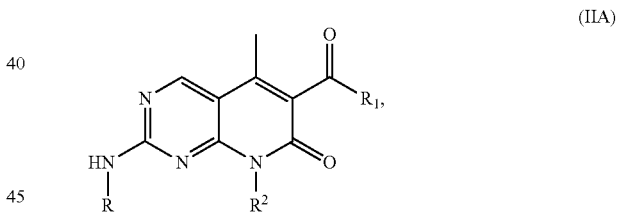

(R)-8-cyclopentyl-2-((3,5-dichloro-4-hydroxyphenyl)amino)-5-methyl-7-(pyrrolidin-1-ylmethyl)-7,8-dihydropteridin-6(5H)-one In certain embodiments, the invention provides a compound of Formula (IIA) or a salt, solvate, enantiomer, diastereoisomer, or tautomer thereof:

(IIA)

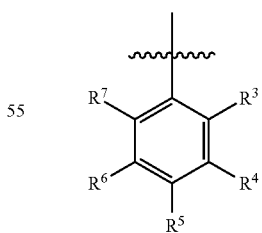

wherein:
R is or heteroaryl, wherein the heteroaryl is optionally substituted with at least one selected from the group consisting of $C_1$-$C_6$ alkyl, $C_3$-$C_8$ cycloalkyl, $C_1$-$C_6$ alkoxy, $C_3$-$C_8$ cycloalkoxy, halogen, —OH, —C(=O)OH, —C(=O)$C_1$-$C_6$ alkyl, —C(=O)$C_3$-$C_8$ cycloalkyl, thiol, $C_1$-$C_6$ thioalkoxy, and —NR'R', wherein each occurrence of R' is independently H or $C_1$-$C_6$ alkyl or the two R' bound to the N combine to form 3-7 membered heterocyclyl;

$R^1$ is selected from the group consisting of $C_1$-$C_6$ alkyl (such as, but not limited to, —CH(CH$_3$)$_2$), $C_3$-$C_8$ cycloalkyl, $C_1$-$C_6$ heteroalkyl, $C_3$-$C_8$ heterocycloalkyl, $C_2$-$C_6$ alkenyl, and $C_2$-$C_6$ alkynyl;

wherein in $R^1$ each occurrence of alkyl, cycloalkyl, heteroalkyl, heterocycloalkyl, alkenyl, or alkynyl is optionally substituted with at least one substituent selected from the group consisting of $C_1$-$C_6$ alkyl, $C_3$-$C_8$ cycloalkyl, $C_1$-$C_6$ alkoxy, $C_3$-$C_8$ cycloalkoxy, halogen, —OH, thiol, $C_1$-$C_6$ thioalkoxy, phenyl, heteroaryl, heterocyclyl, and —NR"R", wherein each occurrence of R' is independently H or $C_1$-$C_6$ alkyl or the two R" bound to the N combine to form 3-7 membered heterocyclyl;

$R^2$ is selected from the group consisting of $C_1$-$C_6$ alkyl, $C_3$-$C_8$ cycloalkyl, $C_1$-$C_6$ heteroalkyl, $C_3$-$C_8$ heterocycloalkyl, $C_2$-$C_6$ alkenyl, and $C_2$-$C_6$ alkynyl;

wherein in $R^2$ each occurrence of alkyl, cycloalkyl, heteroalkyl, heterocycloalkyl, alkenyl, or alkynyl is optionally substituted with at least one substituent selected from the group consisting of $C_1$-$C_6$ alkyl, $C_3$-$C_8$ cycloalkyl, $C_1$-$C_6$ alkoxy, $C_3$-$C_8$ cycloalkoxy, halogen, —OH, thiol, $C_1$-$C_6$ thioalkoxy, phenyl, heteroaryl, heterocyclyl, and —NR'"R'", wherein each occurrence of R' is independently H or $C_1$-$C_6$ alkyl or the two R'" bound to the N combine to form 3-7 membered heterocyclyl;

$R^3$ is selected from the group consisting of H, halogen, $C_1$-$C_6$ alkyl, and $C_3$-$C_8$ cycloalkyl;

$R^4$ is selected from the group consisting of H, halogen, $C_1$-$C_6$ alkyl, $C_3$-$C_8$ cycloalkyl, —OH, —C(=O)OH, —C(=O)$C_1$-$C_6$ alkyl, and —C(=O)$C_3$-$C_8$ cycloalkyl;

$R^5$ is selected from the group consisting of H, —OH, —C(=O)OH, —C(=O)$C_1$-$C_6$ alkyl, and —C(=O)$C_3$-$C_8$ cycloalkyl;

$R^6$ is selected from the group consisting of H, halogen, $C_1$-$C_6$ alkyl, $C_3$-$C_8$ cycloalkyl, —OH, —C(=O)OH, —C(=O)$C_1$-$C_6$ alkyl, and —C(=O)$C_3$-$C_8$ cycloalkyl; and $R^7$ is selected from the group consisting of H, halogen, $C_1$-$C_6$ alkyl, and $C_3$-$C_8$ cycloalkyl.

In certain embodiments, the invention provides a compound of Formula (IIB) or a salt, solvate, enantiomer, diastereoisomer, or tautomer thereof:

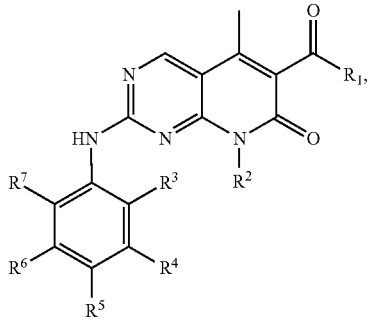

(IIB)

wherein:

$R^1$ is selected from the group consisting of $C_1$-$C_6$ alkyl (such as, but not limited to, —CH(CH$_3$)$_2$), $C_3$-$C_8$ cycloalkyl, $C_1$-$C_6$ heteroalkyl, $C_3$-$C_8$ heterocycloalkyl, $C_2$-$C_6$ alkenyl, and $C_2$-$C_6$ alkynyl;

wherein in $R^1$ each occurrence of alkyl, cycloalkyl, heteroalkyl, heterocycloalkyl, alkenyl, or alkynyl is optionally substituted with at least one substituent selected from the group consisting of $C_1$-$C_6$ alkyl, $C_3$-$C_8$ cycloalkyl, $C_1$-$C_6$ alkoxy, $C_3$-$C_8$ cycloalkoxy, halogen, —OH, thiol, $C_1$-$C_6$ thioalkoxy, phenyl, heteroaryl, heterocyclyl, and —NR"R", wherein each occurrence of R' is independently H or $C_1$-$C_6$ alkyl or the two R" bound to the N combine to form 3-7 membered heterocyclyl;

$R^2$ is selected from the group consisting of $C_1$-$C_6$ alkyl, $C_3$-$C_8$ cycloalkyl, $C_1$-$C_6$ heteroalkyl, $C_3$-$C_8$ heterocycloalkyl, $C_2$-$C_6$ alkenyl, and $C_2$-$C_6$ alkynyl;

wherein in $R^2$ each occurrence of alkyl, cycloalkyl, heteroalkyl, heterocycloalkyl, alkenyl, or alkynyl is optionally substituted with at least one substituent selected from the group consisting of $C_1$-$C_6$ alkyl, $C_3$-$C_8$ cycloalkyl, $C_1$-$C_6$ alkoxy, $C_3$-$C_8$ cycloalkoxy, halogen, —OH, thiol, $C_1$-$C_6$ thioalkoxy, phenyl, heteroaryl, heterocyclyl, and —NR'"R'", wherein each occurrence of R' is independently H or $C_1$-$C_6$ alkyl or the two R'" bound to the N combine to form 3-7 membered heterocyclyl;

$R^3$ is selected from the group consisting of H, halogen, $C_1$-$C_6$ alkyl, and $C_3$-$C_8$ cycloalkyl;

$R^4$ is selected from the group consisting of H, halogen, $C_1$-$C_6$ alkyl, $C_3$-$C_8$ cycloalkyl, —OH, —C(=O)OH, —C(=O)$C_1$-$C_6$ alkyl, and —C(=O)$C_3$-$C_8$ cycloalkyl;

$R^5$ is selected from the group consisting of H, —OH, —C(=O)OH, —C(=O)$C_1$-$C_6$ alkyl, and —C(=O)$C_3$-$C_8$ cycloalkyl;

$R^6$ is selected from the group consisting of H, halogen, $C_1$-$C_6$ alkyl, $C_3$-$C_8$ cycloalkyl, —OH, —C(=O)OH, —C(=O)$C_1$-$C_6$ alkyl, and —C(=O)$C_3$-$C_8$ cycloalkyl; and $R^7$ is selected from the group consisting of H, halogen, $C_1$-$C_6$ alkyl, and $C_3$-$C_8$ cycloalkyl.

In certain embodiments, R is heteroaryl selected from the group consisting of 1H-benzo[d][1,2,3]triazolyl, triazolyl, thiazolyl, oxazolyl, isooxazolyl, oxadiazolyl, thiodiazolyl, pyridinyl, pyrimidinyl, triazinyl, pyrazinyl, thiophenyl, benzotriazolyl, benzamidazolyl, indolyl, indazolyl, pyrrolyl, and pyrazolyl.

In certain embodiments, the heterocyclyl is aziridinyl, azetidinyl, pyrrolidinyl, piperazinyl, or morpholinyl.

In certain embodiments, $R^1$ is $C_1$-$C_3$ alkyl. In other embodiments, $R^1$ is $C_4$-$C_6$ alkyl. In yet other embodiments, $R^1$ is methyl. In yet other embodiments, $R^1$ is ethyl. In yet other embodiments, $R^1$ is $C_3$ alkyl. In yet other embodiments, $R^1$ is $C_4$ alkyl. In yet other embodiments, $R^1$ is $C_5$ alkyl. In yet other embodiments, $R^1$ is $C_6$ alkyl.

In certain embodiments, $R^1$ is isopropyl. In certain embodiments, $R^1$ is isobutyl. In certain embodiments, $R^1$ is sec-butyl. In certain embodiments, $R^1$ is tert-butyl. In certain embodiments, $R^1$ is cyclopentylmethyl. In certain embodiments, $R^1$ is cyclohexylmethyl.

In certain embodiments, $R^1$ is a substituent of structure:

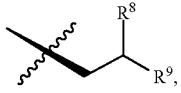

wherein: $R^8$ is selected from the group consisting of $C_1$-$C_6$ alkyl, $C_3$-$C_8$ cycloalkyl, halogen, thiol, $C_1$-$C_6$ thioalkoxy, —OH, $C_1$-$C_6$ alkoxy, and —NR"R"; and $R^9$ is selected from the group consisting of H, $C_1$-$C_6$ alkyl, $C_3$-$C_8$ cycloalkyl, halogen, thiol, $C_1$-$C_6$ thioalkoxy, —OH, $C_1$-$C_6$ alkoxy, and —NR"R", wherein each occurrence of R" is independently H or $C_1$-$C_6$ alkyl.

In certain embodiments, if $R^8$ is methyl, $R^9$ is not H.

In certain embodiments, if $R^9$ is H, $R^8$ is not methyl.

In certain embodiments, $R^2$ is cyclopentyl. In certain embodiments, $R^2$ is cyclohexyl.

In certain embodiments, $R^4$ and $R^6$ are independently selected from the group consisting of F, Cl, Br and I. In other embodiments, $R^4$ and $R^6$ are both Cl.

In certain embodiments, $R^5$ is OH.

In certain embodiments, at least one of $R^4$, $R^5$, and $R^6$ is selected from the group consisting of —OH, —C(=O)OH, —C(=O)$C_1$-$C_6$ alkyl, and —C(=O)$C_3$-$C_8$ cycloalkyl. In certain embodiments, at least one of $R^4$, $R^5$, and $R^6$ is —C(=O)OH. In certain embodiments, at least one of $R^4$, $R^5$, and $R^6$ is —C(=O)$C_1$-$C_6$ alkyl. In certain embodiments, at least one of $R^4$, $R^5$, and $R^6$ is —C(=O)$C_3$-$C_8$ cycloalkyl.

In certain embodiments, R in (IIA) is heteroaryl with an acidic group of pKa<8. Non-limiting examples of such heteroaryl groups include benzotriazole, triazole, tetrazole, and so forth. In certain embodiments, R in (IIA) is heteroaryl substituted with at least one of —OH, —C(=O)OH, —C(=O)$C_1$-$C_6$ alkyl, and —C(=O)$C_3$-$C_8$ cycloalkyl. In certain embodiments, R in (IIA) is heteroaryl substituted with —C(=O)OH. In certain embodiments, R in (IIA) is heteroaryl substituted with —C(=O)$C_1$-$C_6$ alkyl. In certain embodiments, In other embodiments, R in (IIA) is heteroaryl substituted with —C(=O)$C_3$-$C_8$ cycloalkyl.

Figure 10A:
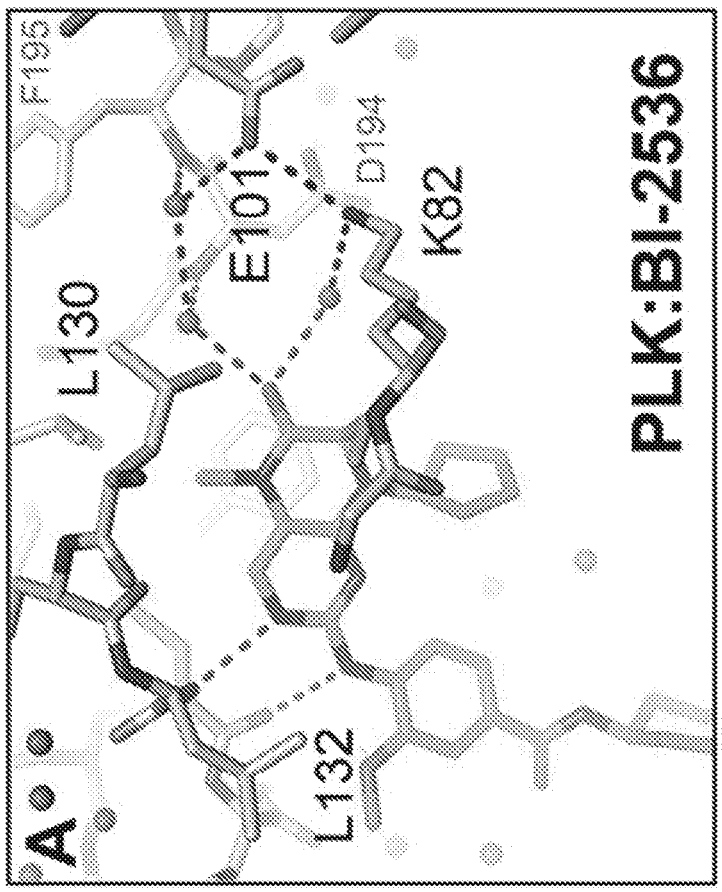
FIGS. 10A-10C are diagrams showing a PIPK-specific hydrophobic pocket in comparison to the corresponding pocket in protein kinase.
Figure 10B:
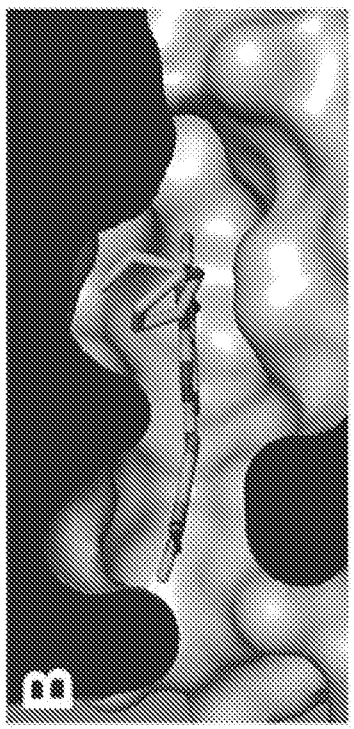
Figure 10C:
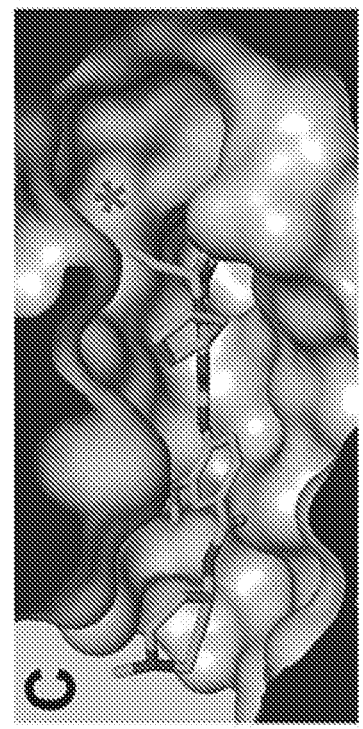
Figure 11A:
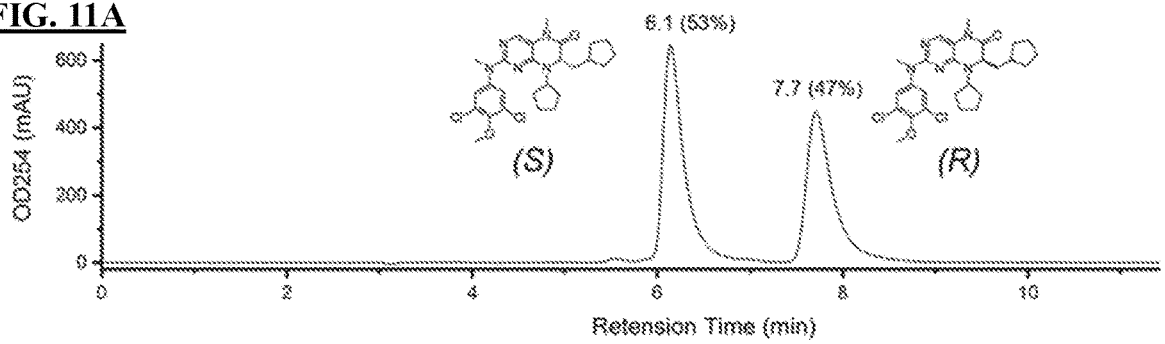
FIGS. 11A-11C are graphs showing the determination of the enantiomeric purity of 7a. In order to determine the enantiomeric purity of 7a, the enantiomer of 7a was prepared according to the same method used to prepare 7a starting from the (S) enantiomer of the starting amino acid 1a. Chiral separation of 7a and (S)-7a was not possible with chiral HPLC chiral columns and conditions. Therefore, a derivative of 7a with both acidic —NH and —OH methylated was prepared. The N,O-dimethylated derivative was also prepared for the (S)-7a. Chiral HPLC analysis of the N,O-dimethylated derivative of 7a using the Chiralpak AD-H established high enantiomeric purity (95% ee).
Figure 11B:
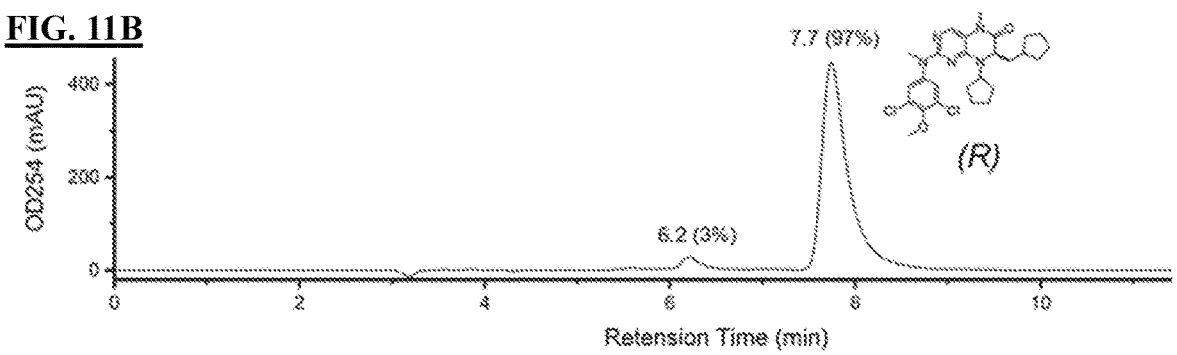
Figure 11C:
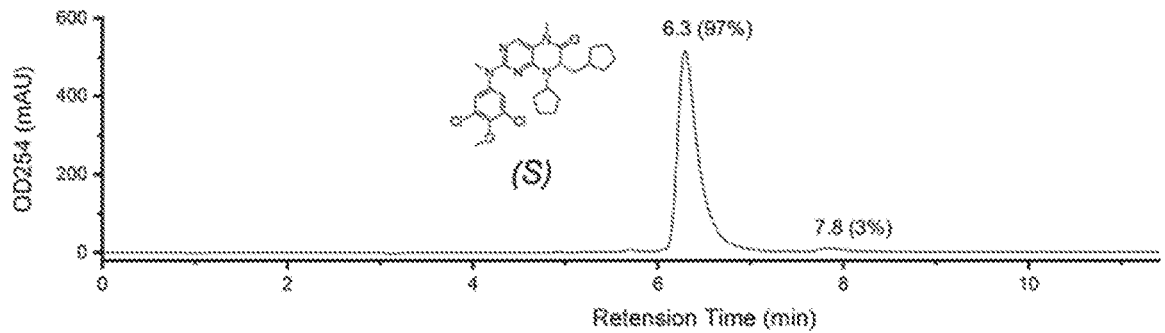
Figure 12A:
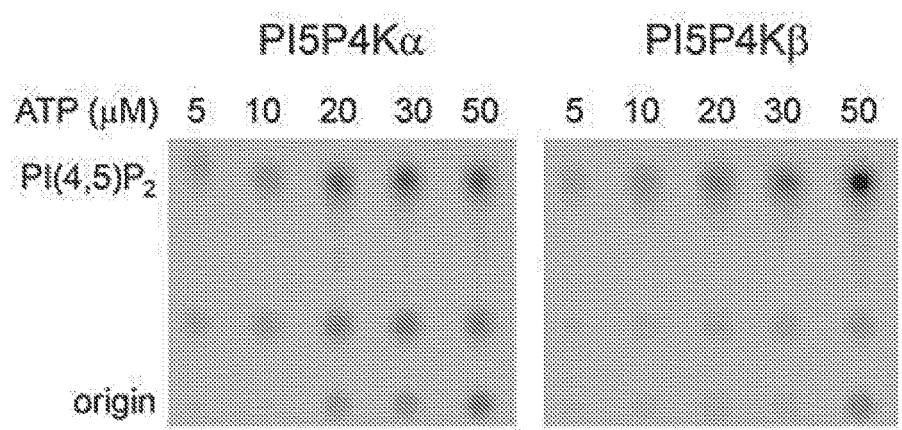
FIGS. 12A-12D are autoradiographs and graphs showing the determination of the $K_i$s for the newly synthesized inhibitors of the invention.
Figure 12B:
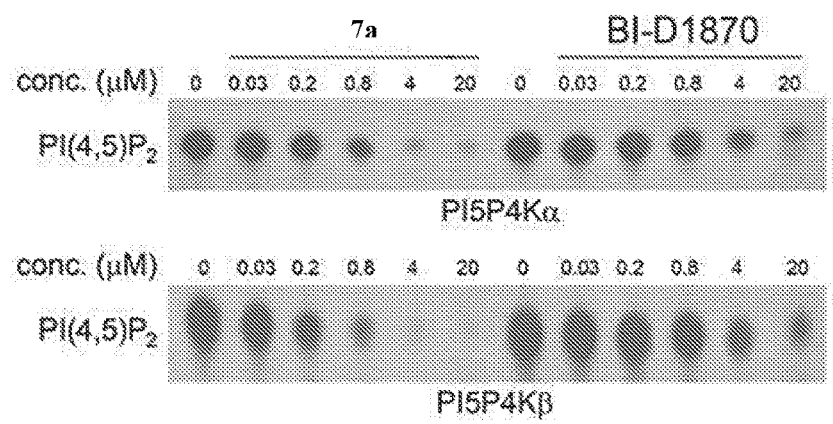
Figure 12C:
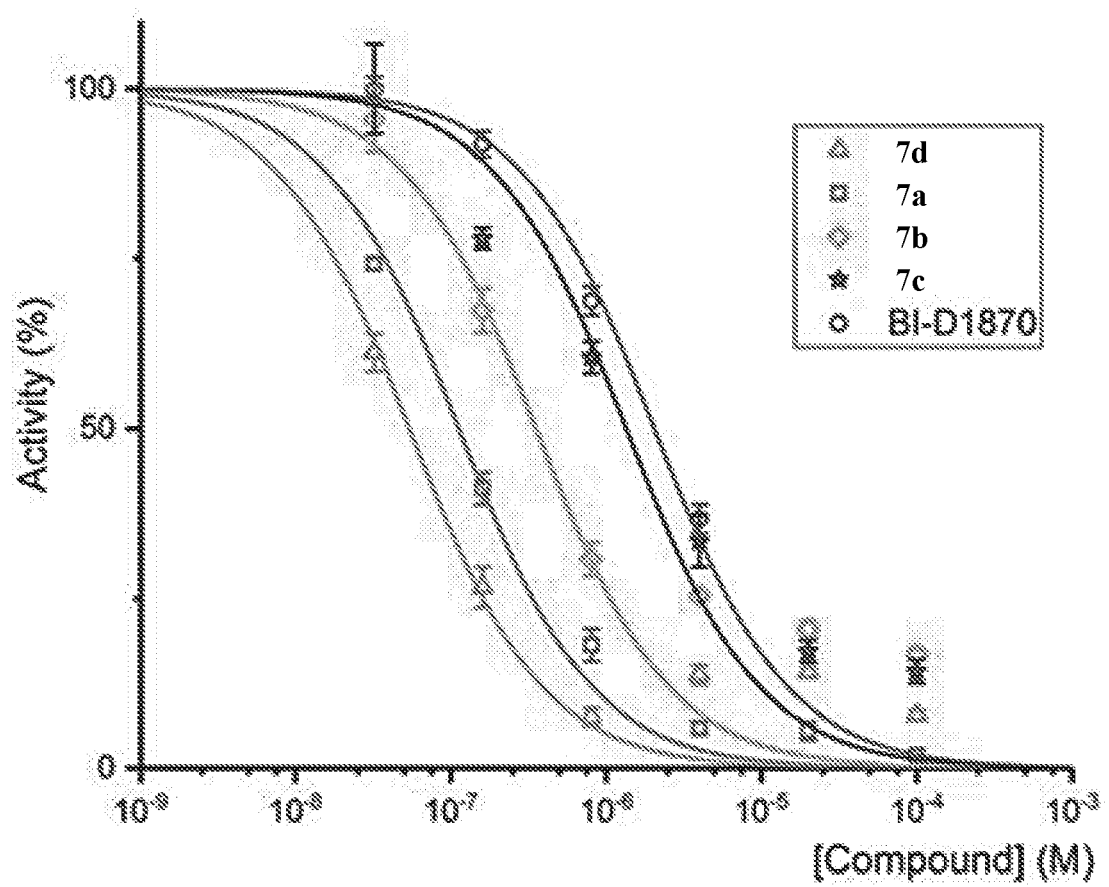
Figure 12D:
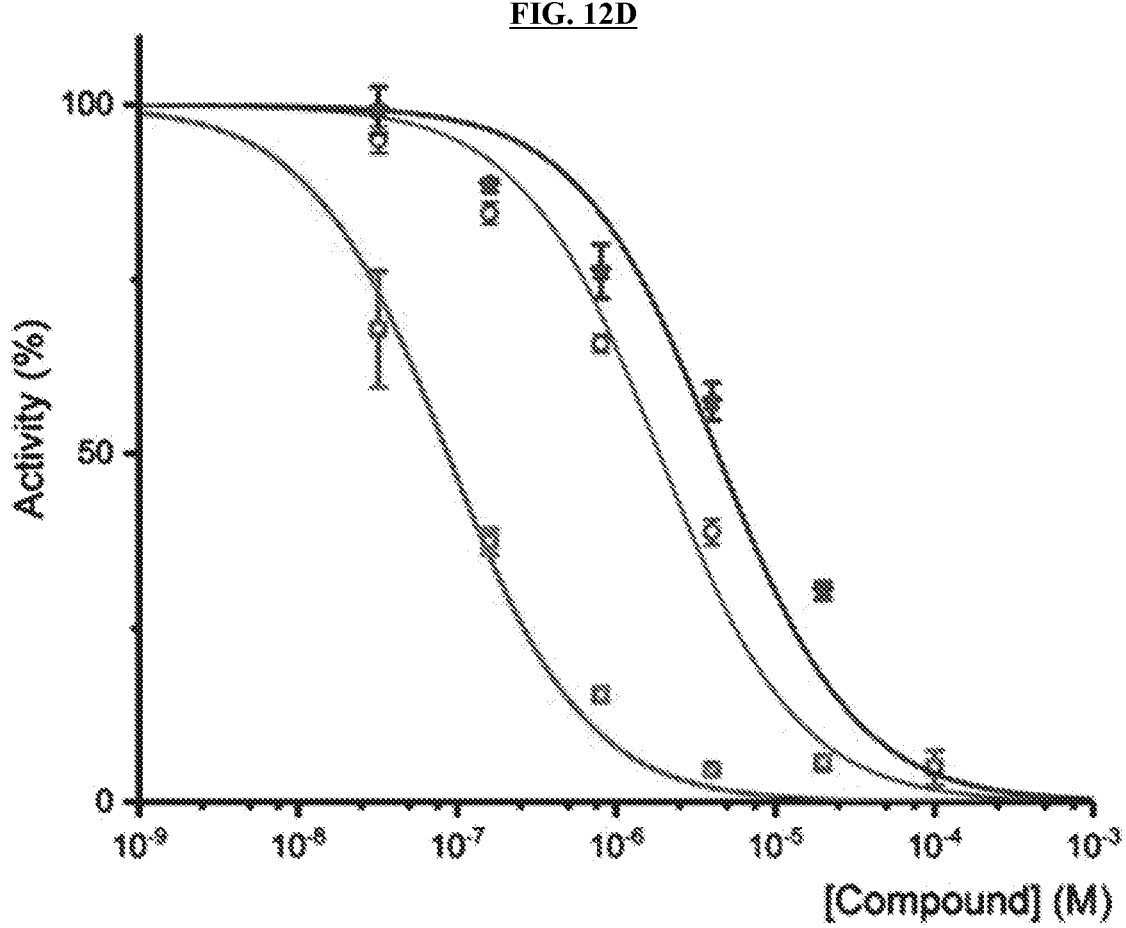
Figure 12D:
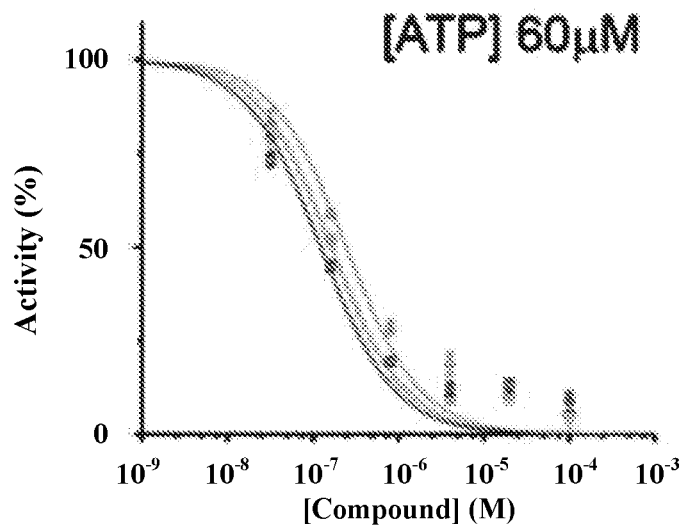

Without wishing to be limited by any theory, in (IIA) or (IIB) $R^1$ is located in the vicinity of the PIPK-specific pocket (FIG. 10C). In certain embodiments, the orientation of $R^1$ in (IIA) or (IIB), pointing up as $R^1$ in Formula (IA) or (IB), is maintained by hydrogen bonds between the carbonyl oxygen (pointing down) and the lipid kinase.

In certain embodiments, the compound of Formula (IA), (IB), (IIA), or (IIB) is capable of binding at least one phosphatidylinositol phosphate kinase. In other embodiments, the compound is capable of binding at least one type 2 phosphatidylinositol phosphate kinase. In yet other embodiments, the compound is capable of binding at least one selected from the group consisting of PI5P4Kα and PI5P4Kβ. In yet other embodiments, the compound is capable of inhibiting the activity of at least one phosphatidylinositol phosphate kinase. In yet other embodiments, the compound is capable of inhibiting the activity of at least one type 2 phosphatidylinositol phosphate kinase. In yet other embodiments, the compound is capable of inhibiting the activity of at least one selected from the group consisting of PI5P4Kα and PI5P4Kβ.

In certain embodiments, the compound of Formula (IA), (IB), (IIA), or (IIB) is useful in the treatment of at least one disease or disorder related to activity of at least one selected from the group consisting of PI5P4Kα and PI5P4Kβ. In other embodiments, the compound is useful in treating a p53-null cancer in a subject. In yet other embodiments, the compound is useful in treating metabolic disorders in a subject.

In certain embodiments, the subject is a mammal. In other embodiments, the subject is a human.

In certain embodiments, the compound of the invention is formulated as part of a pharmaceutical composition, further comprising at least one pharmaceutically acceptable carrier. In certain embodiments, the pharmaceutical composition further comprises at least one additional therapeutic agent. In other embodiments, the at least one additional therapeutic agent is a chemotherapeutic agent.

The compounds of the invention may possess one or more stereocenters, and each stereocenter may exist independently in either the (R) or (S) configuration. In one embodiment, compounds described herein are present in optically active or racemic forms. The compounds described herein encompass racemic, optically-active, regioisomeric and stereoisomeric forms, or combinations thereof that possess the therapeutically useful properties described herein. Preparation of optically active forms is achieved in any suitable manner, including by way of non-limiting example, by resolution of the racemic form with recrystallization techniques, synthesis from optically-active starting materials, chiral synthesis, or chromatographic separation using a chiral stationary phase. In one embodiment, a mixture of one or more isomer is utilized as the therapeutic compound described herein. In another embodiment, compounds described herein contain one or more chiral centers. These compounds are prepared by any means, including stereoselective synthesis, enantioselective synthesis and/or separation of a mixture of enantiomers and/or diastereomers. Resolution of compounds and isomers thereof is achieved by any means including, by way of non-limiting example, chemical processes, enzymatic processes, fractional crystallization, distillation, and chromatography.

The methods and formulations described herein include the use of N-oxides (if appropriate), crystalline forms (also known as polymorphs), solvates, amorphous phases, and/or pharmaceutically acceptable salts of compounds having the structure of any compound of the invention, as well as metabolites and active metabolites of these compounds having the same type of activity. Solvates include water, ether (e.g., tetrahydrofuran, methyl tert-butyl ether) or alcohol (e.g., ethanol) solvates, acetates and the like. In one embodiment, the compounds described herein exist in solvated forms with pharmaceutically acceptable solvents such as water, and ethanol. In another embodiment, the compounds described herein exist in unsolvated form.

In one embodiment, the compounds of the invention exist as tautomers. All tautomers are included within the scope of the compounds recited herein.

In one embodiment, compounds described herein are prepared as prodrugs. A "prodrug" is an agent converted into the parent drug in vivo. In one embodiment, upon in vivo administration, a prodrug is chemically converted to the biologically, pharmaceutically or therapeutically active form of the compound. In another embodiment, a prodrug is enzymatically metabolized by one or more steps or processes to the biologically, pharmaceutically or therapeutically active form of the compound.

In one embodiment, sites on, for example, the aromatic ring portion of compounds of the invention are susceptible to various metabolic reactions. Incorporation of appropriate substituents on the aromatic ring structures may reduce, minimize or eliminate this metabolic pathway. In one embodiment, the appropriate substituent to decrease or eliminate the susceptibility of the aromatic ring to metabolic reactions is, by way of example only, a deuterium, a halogen, or an alkyl group.

Compounds described herein also include isotopically-labeled compounds wherein one or more atoms is replaced by an atom having the same atomic number, but an atomic mass or mass number different from the atomic mass or mass number usually found in nature. Examples of isotopes suitable for inclusion in the compounds described herein include and are not limited to $^2$H, $^3$H, $^{11}$C, $^{13}$C, $^{14}$C, $^{36}$Cl, $^{18}$F, $^{123}$I, $^{125}$I, $^{13}$N, $^{15}$N, $^{15}$O, $^{17}$O, $^{18}$O, $^{32}$P, and $^{35}$S. In one embodiment, isotopically-labeled compounds are useful in drug and/or substrate tissue distribution studies. In another embodiment, substitution with heavier isotopes such as deuterium affords greater metabolic stability (for example, increased in vivo half-life or reduced dosage requirements). In yet another embodiment, substitution with positron emitting isotopes, such as $^{11}C$, $^{18}F$, $^{15}O$ and $^{13}N$, is useful in Positron Emission Topography (PET) studies for examining substrate receptor occupancy. Isotopically-labeled compounds are prepared by any suitable method or by processes using an appropriate isotopically-labeled reagent in place of the non-labeled reagent otherwise employed.

In one embodiment, the compounds described herein are labeled by other means, including, but not limited to, the use of chromophores or fluorescent moieties, bioluminescent labels, or chemiluminescent labels.

The compounds described herein, and other related compounds having different substituents are synthesized using techniques and materials described herein and as described, for example, in Fieser & Fieser's Reagents for Organic Synthesis, Volumes 1-17 (John Wiley and Sons, 1991); Rodd's Chemistry of Carbon Compounds, Volumes 1-5 and Supplementals (Elsevier Science Publishers, 1989); Organic Reactions, Volumes 1-40 (John Wiley and Sons, 1991), Larock's Comprehensive Organic Transformations (VCH Publishers Inc., 1989), March, Advanced Organic Chemistry $4^{th}$ Ed., (Wiley 1992); Carey & Sundberg, Advanced Organic Chemistry 4th Ed., Vols. A and B (Plenum 2000, 2001), and Green & Wuts, Protective Groups in Organic Synthesis 3rd Ed., (Wiley 1999) (all of which are incorporated by reference for such disclosure). General methods for the preparation of compound as described herein are modified by the use of appropriate reagents and conditions, for the introduction of the various moieties found in the formula as provided herein.

Compounds described herein are synthesized using any suitable procedures starting from compounds that are available from commercial sources, or are prepared using procedures described herein.

The invention further includes a pharmaceutical composition comprising the compound of the invention and a pharmaceutically acceptable carrier. In certain embodiments, the pharmaceutical composition further comprises at least one additional agent that is useful to treat the diseases or disorders contemplated herein. In certain embodiments, the compound of the invention and the additional agent are coformulated in the composition.

Salts

The compounds described herein may form salts with acids or bases, and such salts are included in the present invention. In one embodiment, the salts are pharmaceutically acceptable salts. The term "salts" embraces addition salts of free acids or bases that are useful within the methods of the invention. The term "pharmaceutically acceptable salt" refers to salts that possess toxicity profiles within a range that affords utility in pharmaceutical applications. Pharmaceutically unacceptable salts may nonetheless possess properties such as high crystallinity, which have utility in the practice of the present invention, such as for example utility in process of synthesis, purification or formulation of compounds useful within the methods of the invention.

Suitable pharmaceutically acceptable acid addition salts may be prepared from an inorganic acid or from an organic acid. Examples of inorganic acids include hydrochloric, hydrobromic, hydriodic, nitric, carbonic, sulfuric (including sulfate and hydrogen sulfate), and phosphoric acids (including hydrogen phosphate and dihydrogen phosphate). Appropriate organic acids may be selected from aliphatic, cycloaliphatic, aromatic, araliphatic, heterocyclic, carboxylic and sulfonic classes of organic acids, examples of which include formic, acetic, propionic, succinic, glycolic, gluconic, lactic, malic, tartaric, citric, ascorbic, glucuronic, maleic, malonic, saccharin, fumaric, pyruvic, aspartic, glutamic, benzoic, anthranilic, 4-hydroxybenzoic, phenylacetic, mandelic, embonic (pamoic), methanesulfonic, ethanesulfonic, benzenesulfonic, pantothenic, trifluoromethanesulfonic, 2-hydroxyethanesulfonic, p-toluenesulfonic, sulfanilic, cyclohexylaminosulfonic, stearic, alginic, β-hydroxybutyric, salicylic, galactaric and galacturonic acid.

Suitable pharmaceutically acceptable base addition salts of compounds of the invention include, for example, metallic salts including alkali metal, alkaline earth metal and transition metal salts such as, for example, calcium, magnesium, potassium, sodium and zinc salts. Pharmaceutically acceptable base addition salts also include organic salts made from basic amines such as, for example, N,N'-dibenzylethylene-diamine, chloroprocaine, choline, diethanolamine, ethylenediamine, meglumine (N-methylglucamine) and procaine. All of these salts may be prepared from the corresponding compound by reacting, for example, the appropriate acid or base with the compound.

Methods

The invention includes a method of treating and/or preventing p-53 null cancer in a subject in need thereof, the method comprising administering to the subject a therapeutically effective amount of a compound of Formula (IA), (IB), (IIA), or (IIB), or a salt, solvate, enantiomer, diastereoisomer, or tautomer thereof.

In certain embodiments, the cancer is at least one selected from the group consisting of Esophageal/Stomach Cancer, Bladder/Urinary Tract Cancer, Small Cell Lung Cancer, CNS/Brain Cancer, Skin Cancer (Non-Melanoma), I-lead and Neck Cancer, Ampullary Carcinoma, Burkitt's lymphoma, Esophagogastric Cancer, Colorectal Cancer, Ovarian Cancer, Non-Small Cell Lung Cancer, Small Bowel Cancer, Cancer of Unknown Primary, High-grade glioma K27Mmut, Pancreatic Cancer, Uterine Sarcoma, Bladder Cancer, High-grade glioma K27Mwt, Appendiceal Cancer, Breast Cancer, Soft Tissue Sarcoma, B-cell acute lymphoblastic leukemia (hypodiploid), Endometrial Cancer, Penile Cancer, Glioma, Breast Sarcoma, Hepatobiliary Cancer, Vaginal Cancer, Gastrointestinal Neuroendocrine Tumor, Adrenocortical Carcinoma, Prostate Cancer, Sellar Tumor, Hodgkin Lymphoma, Upper Tract Urothelial Carcinoma, Non-Hodgkin Lymphoma, Melanoma, Bone Cancer, Cutaneous Melanoma, Mesothelioma, Adrenocortical carcinoma, Invasive Breast Carcinoma, Salivary Gland Cancer, B-cell acute lymphoblastic leukemia (non-hypodiploid), Anal Cancer, Embryonal tumor with multilayered rosettes, Ewing's sarcoma, Nerve Sheath Tumor, Wilms' tumors, Germ Cell Tumor, Multiple Myeloma, Cervical Cancer, Gastrointestinal Stromal Tumor, Renal Cell Carcinoma, Mature B-Cell Neoplasms, Myelodysplasia Thymic Tumor, Sex Cord Stromal Tumor, Atypial teratoid/rhabdoid tumor, Miscellaneous Neuroepithelial Tumor, Medulloblastoma WNT, Medulloblastoma SHH, Rhabdomyosarcoma, Leukemia, Thyroid Cancer, Embryonal Tumor. Wilms Tumor, Osteosarcoma, CNS Cancer, Neuroblastoma, Medulloblastoma Group3, Pheochromocytoma, B-Lymphoblastic Leukemia/Lymphoma. In other embodiments, the cancer is selected from the group consisting of breast cancer, prostate cancer, and lung cancer. P-53 null cancers are described in Gao, et al. Sci Signal. 2013, 6 (269), pl 1, which is incorporated herein in its entirety by reference.

The invention further includes a method of treating or preventing at least one metabolic disease or disorder in a subject in need thereof, the method comprising administering to the subject a therapeutically effective amount of a compound of Formula (IA), (IB), (IIA), or (IIB), or a salt, solvate, enantiomer, diastereoisomer, or tautomer thereof.

In certain embodiments, the at least one metabolic disorder is selected from the group consisting of type 2 diabetes, obesity, liver disease, and heart disease.

Without being limited to any particular theory, the methods of the invention allow for inhibition of at least one phosphatidylinositol phosphate kinase. In certain embodiments, the at least one phosphatidylinositol phosphate kinase is a type 2 phosphatidylinositol phosphate kinase. In other embodiments, the at least one phosphatidylinositol phosphate kinase is at least one of PI5P4K$\alpha$ and PI5P4K$\beta$.

In certain embodiments, the therapeutically effective amount of a compound of Formula (IA), (IB), (IIA), or (IIB) is formulated as part of a pharmaceutical composition.

In certain embodiments, the therapeutically effective amount of a compound of Formula (IA), (IB), (IIA), or (IIB) is administered to the subject by a route selected from the group consisting of parenteral and/or oral.

In certain embodiments, the subject is a mammal. In other embodiments, the subject is a human.

Kits

The invention includes a kit comprising a compound of the invention, an applicator, and an instructional material for use thereof. The instructional material included in the kit comprises instructions for preventing or treating a disorder or disease contemplated within the invention in a subject. The instructional material recites the amount of, and frequency with which, the compound of the invention should be administered to the subject. In certain embodiments, the kit further comprises at least one additional agent useful to treat or prevent a disease or disorder contemplated within the invention.

Combination Therapies

In certain embodiments, the compounds of the invention are useful in the methods of the invention in combination with at least one additional compound or treatment useful for treating or preventing a disease or disorder contemplated within the invention. This additional compound may comprise compounds identified herein or compounds, e.g., commercially available compounds, known to treat, prevent or reduce the symptoms of cancer or a metabolic disease or disorder contemplated herein.

Non-limiting examples of agents useful to treat p53-null cancer are chemotherapeutic agents and immunotherapeutic agents. In other embodiments, the compounds of the invention are useful in treating cancer in combination with one or more cancer treating radiation therapies.

Non-limiting examples of agents useful for treating type 2 diabetes include insulin, blood thinners, statins, and anti-diabetic medications. Non-limiting examples of anti-diabetic medications can include drugs such as metformin, sulfonylureas, meglitinides, thiazolidinediones, DPP-4 inhibitors, GLP-1 receptor agonists, and SGLT2 inhibitors.

A synergistic effect may be calculated, for example, using suitable methods such as, for example, the Sigmoid-$E_{max}$ equation (Holford & Schemer, 19981, Clin. Pharmacokinet. 6: 429-453), the equation of Loewe additivity (Loewe & Muischnek, 1926, Arch. Exp. Pathol Pharmacol. 114: 313-326) and the median-effect equation (Chou & Talalay, 1984, Adv. Enzyme Regul. 22:27-55). Each equation referred to above may be applied to experimental data to generate a corresponding graph to aid in assessing the effects of the drug combination. The corresponding graphs associated with the equations referred to above are the concentration-effect curve, isobologram curve and combination index curve, respectively.

Administration/Dosage/Formulations

The regimen of administration may affect what constitutes an effective amount. The therapeutic formulations may be administered to the subject either prior to or after the onset of a disease or disorder contemplated in the invention. Further, several divided dosages, as well as staggered dosages may be administered daily or sequentially, or the dose may be continuously infused, or may be a bolus injection. Further, the dosages of the therapeutic formulations may be proportionally increased or decreased as indicated by the exigencies of the therapeutic or prophylactic situation.

Administration of the compositions of the present invention to a patient, preferably a mammal, more preferably a human, may be carried out using known procedures, at dosages and for periods of time effective to treat a disease or disorder contemplated in the invention. An effective amount of the therapeutic compound necessary to achieve a therapeutic effect may vary according to factors such as the state of the disease or disorder in the patient; the age, sex, and weight of the patient; and the ability of the therapeutic compound to treat a disease or disorder contemplated in the invention. Dosage regimens may be adjusted to provide the optimum therapeutic response. For example, several divided doses may be administered daily or the dose may be proportionally reduced as indicated by the exigencies of the therapeutic situation. A non-limiting example of an effective dose range for a therapeutic compound of the invention is from about 1 and 5,000 mg/kg of body weight/per day. One of ordinary skill in the art would be able to study the relevant factors and make the determination regarding the effective amount of the therapeutic compound without undue experimentation.

Actual dosage levels of the active ingredients in the pharmaceutical compositions of this invention may be varied so as to obtain an amount of the active ingredient that is effective to achieve the desired therapeutic response for a particular patient, composition, and mode of administration, without being toxic to the patient.

In particular, the selected dosage level depends upon a variety of factors including the activity of the particular compound employed, the time of administration, the rate of excretion of the compound, the duration of the treatment, other drugs, compounds or materials used in combination with the compound, the age, sex, weight, condition, general health and prior medical history of the patient being treated, and like factors well, known in the medical arts.

A medical doctor, e.g., physician or veterinarian, having ordinary skill in the art may readily determine and prescribe the effective amount of the pharmaceutical composition required. For example, the physician or veterinarian could start doses of the compounds of the invention employed in the pharmaceutical composition at levels lower than that required in order to achieve the desired therapeutic effect and gradually increase the dosage until the desired effect is achieved.

In particular embodiments, it is especially advantageous to formulate the compound in dosage unit form for ease of administration and uniformity of dosage. Dosage unit form as used herein refers to physically discrete units suited as unitary dosages for the patients to be treated; each unit containing a predetermined quantity of therapeutic compound calculated to produce the desired therapeutic effect in association with the required pharmaceutical vehicle. The dosage unit forms of the invention are dictated by and directly dependent on (a) the unique characteristics of the therapeutic compound and the particular therapeutic effect to be achieved, and (b) the limitations inherent in the art of compounding/formulating such a therapeutic compound for the treatment of a disease or disorder contemplated in the invention.

In one embodiment, the compositions of the invention are formulated using one or more pharmaceutically acceptable excipients or carriers. In one embodiment, the pharmaceutical compositions of the invention comprise a therapeutically effective amount of a compound of the invention and a pharmaceutically acceptable carrier.

The carrier may be a solvent or dispersion medium containing, for example, water, ethanol, polyol (for example, glycerol, propylene glycol, and liquid polyethylene glycol, and the like), suitable mixtures thereof, and vegetable oils.

In one embodiment, the compositions of the invention are administered to the patient in dosages that range from one to five times per day or more. In another embodiment, the compositions of the invention are administered to the patient in range of dosages that include, but are not limited to, once every day, every two, days, every three days to once a week, and once every two weeks. It is readily apparent to one skilled in the art that the frequency of administration of the various combination compositions of the invention varies from individual to individual depending on many factors including, but not limited to, age, disease or disorder to be treated, gender, overall health, and other factors. Thus, the invention should not be construed to be limited to any particular dosage regime and the precise dosage and composition to be administered to any patient is determined by the attending physical taking all other factors about the patient into account.

Compounds of the invention for administration may be in the range of from about 1 µg to about 10,000 mg, about 20 µg to about 9,500 mg, about 40 µg to about 9,000 mg, about 75 µg to about 8,500 mg, about 150 µg to about 7,500 mg, about 200 µg to about 7,000 mg, about 3050 µg to about 6,000 mg, about 500 µg to about 5,000 mg, about 750 µg to about 4,000 mg, about 1 mg to about 3,000 mg, about 10 mg to about 2,500 mg, about 20 mg to about 2,000 mg, about 25 mg to about 1,500 mg, about 30 mg to about 1,000 mg, about 40 mg to about 900 mg, about 50 mg to about 800 mg, about 60 mg to about 750 mg, about 70 mg to about 600 mg, about 80 mg to about 500 mg, and any and all whole or partial increments therebetween.

In one embodiment, the present invention is directed to a packaged pharmaceutical composition comprising a container holding a therapeutically effective amount of a compound of the invention, alone or in combination with a second pharmaceutical agent; and instructions for using the compound to treat, prevent, or reduce one or more symptoms of a disease or disorder contemplated in the invention.

Formulations may be employed in admixtures with conventional excipients, i.e., pharmaceutically acceptable organic or inorganic carrier substances suitable for oral, parenteral, nasal, intravenous, subcutaneous, enteral, or any other suitable mode of administration, known to the art. The pharmaceutical preparations may be sterilized and if desired mixed with auxiliary agents, e.g., lubricants, preservatives, stabilizers, wetting agents, emulsifiers, salts for influencing osmotic pressure buffers, coloring, flavoring and/or aromatic substances and the like. They may also be combined where desired with other active agents, e.g., anti-cancer agents, anti-diabetic agents.

Routes of administration of any of the compositions of the invention include oral, nasal, rectal, intravaginal, parenteral, buccal, sublingual or topical. The compounds for use in the invention may be formulated for administration by any suitable route, such as for oral or parenteral, for example, transdermal, transmucosal (e.g., sublingual, lingual, (trans) buccal, (trans)urethral, vaginal (e.g., trans- and perivaginally), (intra)nasal and (trans)rectal), intravesical, intrapulmonary, intraduodenal, intragastrical, intrathecal, subcutaneous, intramuscular, intradermal, intra-arterial, intravenous, intrabronchial, inhalation, and topical administration.

Suitable compositions and dosage forms include, for example, tablets, capsules, caplets, pills, gel caps, troches, dispersions, suspensions, solutions, syrups, granules, beads, transdermal patches, gels, powders, pellets, magmas, lozenges, creams, pastes, plasters, lotions, discs, suppositories, liquid sprays for nasal or oral administration, dry powder or aerosolized formulations for inhalation, compositions and formulations for intravesical administration and the like. It should be understood that the formulations and compositions that would be useful in the present invention are not limited to the particular formulations and compositions that are described herein.

Oral Administration

For oral application, particularly suitable are tablets, dragees, liquids, drops, suppositories, or capsules, caplets and gelcaps. The compositions intended for oral use may be prepared according to any method known in the art and such compositions may contain one or more agents selected from the group consisting of inert, non-toxic pharmaceutically excipients that are suitable for the manufacture of tablets. Such excipients include, for example an inert diluent such as lactose; granulating and disintegrating agents such as cornstarch; binding agents such as starch; and lubricating agents such as magnesium stearate. The tablets may be uncoated or they may be coated by known techniques for elegance or to delay the release of the active ingredients. Formulations for oral use may also be presented as hard gelatin capsules wherein the active ingredient is mixed with an inert diluent.

Parenteral Administration

As used herein, "parenteral administration" of a pharmaceutical composition includes any route of administration characterized by physical breaching of a tissue of a subject and administration of the pharmaceutical composition through the breach in the tissue. Parenteral administration thus includes, but is not limited to, administration of a pharmaceutical composition by injection of the composition, by application of the composition through a surgical incision, by application of the composition through a tissue-penetrating non-surgical wound, and the like. In particular, parenteral administration is contemplated to include, but is not limited to, subcutaneous, intravenous, intraperitoneal, intramuscular, intrasternal injection, and kidney dialytic infusion techniques.

Formulations of a pharmaceutical composition suitable for parenteral administration comprise the active ingredient combined with a pharmaceutically acceptable carrier, such as sterile water or sterile isotonic saline. Such formulations may be prepared, packaged, or sold in a form suitable for bolus administration or for continuous administration. Injectable formulations may be prepared, packaged, or sold in unit dosage form, such as in ampules or in multidose containers containing a preservative. Formulations for parenteral administration include, but are not limited to, suspensions, solutions, emulsions in oily or aqueous vehicles, pastes, and implantable sustained-release or biodegradable formulations. Such formulations may further comprise one or more additional ingredients including, but not limited to, suspending, stabilizing, or dispersing agents. In one embodiment of a formulation for parenteral administration, the active ingredient is provided in dry (i.e., powder or granular) form for reconstitution with a suitable vehicle (e.g., sterile pyrogen-free water) prior to parenteral administration of the reconstituted composition.

Additional Administration Forms

Additional dosage forms of this invention include dosage forms as described in U.S. Pat. Nos. 6,340,475; 6,488,962; 6,451,808; 5,972,389; 5,582,837; and 5,007,790. Additional dosage forms of this invention also include dosage forms as described in U.S. Patent Applications Nos. 20030147952; 20030104062; 20030104053; 20030044466; 20030039688; and 20020051820. Additional dosage forms of this invention also include dosage forms as described in PCT Applications Nos. WO 03/35041; WO 03/35040; WO 03/35029; WO 03/35177; WO 03/35039; WO 02/96404; WO 02/32416; WO 01/97783; WO 01/56544; WO 01/32217; WO 98/55107; WO 98/11879; WO 97/47285; WO 93/18755; and WO 90/11757.

Controlled Release Formulations and Drug Delivery Systems

In one embodiment, the formulations of the present invention may be, but are not limited to, short-term, rapid-offset, as well as controlled, for example, sustained release, delayed release and pulsatile release formulations.

The term sustained release is used in its conventional sense to refer to a drug formulation that provides for gradual release of a drug over an extended period of time, and that may, although not necessarily, result in substantially constant blood levels of a drug over an extended time period. The period of time may be as long as a month or more and should be a release which is longer that the same amount of agent administered in bolus form.

In one embodiment of the invention, the compounds of the invention are administered to a patient, alone or in combination with another pharmaceutical agent, using a sustained release formulation.

The term delayed release is used herein in its conventional sense to refer to a drug formulation that provides for an initial release of the drug after some delay following drug administration and that may, although not necessarily, includes a delay of from about 10 minutes up to about 12 hours.

The term pulsatile release is used herein in its conventional sense to refer to a drug formulation that provides release of the drug in such a way as to produce pulsed plasma profiles of the drug after drug administration.

The term immediate release is used in its conventional sense to refer to a drug formulation that provides for release of the drug immediately after drug administration.

As used herein, short-term refers to any period of time up to and including about 8 hours, about 7 hours, about 6 hours, about 5 hours, about 4 hours, about 3 hours, about 2 hours, about 1 hour, about 40 minutes, about 20 minutes, or about 10 minutes and any or all whole or partial increments thereof after drug administration after drug administration.

As used herein, rapid-offset refers to any period of time up to and including about 8 hours, about 7 hours, about 6 hours, about 5 hours, about 4 hours, about 3 hours, about 2 hours, about 1 hour, about 40 minutes, about 20 minutes, or about 10 minutes, and any and all whole or partial increments thereof after drug administration.

Dosing

The therapeutically effective amount or dose of a compound of the present invention depends on the age, sex and weight of the patient, the current medical condition of the patient and the progression of a disease or disorder contemplated in the invention. The skilled artisan is able to determine appropriate dosages depending on these and other factors.

A suitable dose of a compound of the present invention may be in the range of from about 0.01 mg to about 5,000 mg per day, such as from about 0.1 mg to about 1,000 mg, for example, from about 1 mg to about 500 mg, such as about 5 mg to about 250 mg per day. The dose may be administered in a single dosage or in multiple dosages, for example from 1 to 4 or more times per day. When multiple dosages are used, the amount of each dosage may be the same or different. For example, a dose of 1 mg per day may be administered as two 0.5 mg doses, with about a 12-hour interval between doses.

It is understood that the amount of compound dosed per day may be administered, in non-limiting examples, every day, every other day, every 2 days, every 3 days, every 4 days, or every 5 days. For example, with every other day administration, a 5 mg per day dose may be initiated on Monday with a first subsequent 5 mg per day dose administered on Wednesday, a second subsequent 5 mg per day dose administered on Friday, and so on.

In the case wherein the patient's status does improve, upon the doctor's discretion the administration of the inhibitor of the invention is optionally given continuously; alternatively, the dose of drug being administered is temporarily reduced or temporarily suspended for a certain length of time (i.e., a "drug holiday"). The length of the drug holiday optionally varies between 2 days and 1 year, including by way of example only, 2 days, 3 days, 4 days, 5 days, 6 days, 7 days, 10 days, 12 days, 15 days, 20 days, 28 days, 35 days, 50 days, 70 days, 100 days, 120 days, 150 days, 180 days, 200 days, 250 days, 280 days, 300 days, 320 days, 350 days, or 365 days. The dose reduction during a drug holiday includes from 10%-100%, including, by way of example only, 10%, 15%, 20%, 25%, 30%, 35%, 40%, 45%, 50%, 55%, 60%, 65%, 70%, 75%, 80%, 85%, 90%, 95%, or 100%.

Toxicity and therapeutic efficacy of such therapeutic regimens are optionally determined in cell cultures or experimental animals, including, but not limited to, the determination of the $LD_{50}$ (the dose lethal to 50% of the population) and the $ED_{50}$ (the dose therapeutically effective in 50% of the population). The dose ratio between the toxic and therapeutic effects is the therapeutic index, which is expressed as the ratio between $LD_{50}$ and $ED_{50}$. The data obtained from cell culture assays and animal studies are optionally used in formulating a range of dosage for use in human. The dosage of such compounds lies preferably within a range of circulating concentrations that include the $ED_{50}$ with minimal toxicity. The dosage optionally varies within this range depending upon the dosage form employed and the route of administration utilized.

Definitions

As used herein, each of the following terms has the meaning associated with it in this section.

Unless defined otherwise, all technical and scientific terms used herein generally have the same meaning as commonly understood by one of ordinary skill in the art to which this invention belongs. Generally, the nomenclature used herein and the laboratory procedures in pharmacology, pharmaceutical science, separation science and organic chemistry are those well-known and commonly employed in the art. It should be understood that the order of steps or order for performing certain actions is immaterial, so long as the present teachings remain operable. Moreover, two or more steps or actions can be conducted simultaneously or not.

As used herein, the articles "a" and "an" refer to one or to more than one (i.e., to at least one) of the grammatical object of the article. By way of example, "an element" means one element or more than one element.

As used herein, the term "about" is understood by persons of ordinary skill in the art and varies to some extent on the context in which it is used. As used herein when referring to a measurable value such as an amount, a temporal duration, and the like, the term "about" is meant to encompass variations of ±20% or ±10%, more preferably ±5%, even more preferably ±1%, and still more preferably ±0.1% from the specified value, as such variations are appropriate to perform the disclosed methods.

As used herein, the term "composition" or "pharmaceutical composition" refers to a mixture of at least one compound useful within the invention with a pharmaceutically acceptable carrier. The pharmaceutical composition facilitates administration of the compound to a patient or subject. Multiple techniques of administering a compound exist in the art including, but not limited to, intravenous, oral, aerosol, parenteral, ophthalmic, nasal, pulmonary and topical administration.

A "disease" as used herein is a state of health of an animal wherein the animal cannot maintain homeostasis, and wherein if the disease is not ameliorated then the animal's health continues to deteriorate.

The terms "patient," "subject" or "individual" are used interchangeably herein, and refer to any animal, or cells thereof whether in vitro or in situ, amenable to the methods described herein. In a non-limiting embodiment, the patient, subject or individual is a human. In other embodiments, the patient is a non-human mammal including, for example, livestock and pets, such as ovine, bovine, porcine, canine, feline and murine mammals. In yet other embodiments, the patient is an avian animal or bird. Preferably, the patient, individual or subject is human.

As used herein, the term "pharmaceutically acceptable" refers to a material, such as a carrier or diluent, which does not abrogate the biological activity or properties of the compound, and is relatively non-toxic, i.e., the material may be administered to an individual without causing undesirable biological effects or interacting in a deleterious manner with any of the components of the composition in which it is contained.

As used herein, the term "pharmaceutically acceptable carrier" means a pharmaceutically acceptable material, composition or carrier, such as a liquid or solid filler, stabilizer, dispersing agent, suspending agent, diluent, excipient, thickening agent, solvent or encapsulating material, involved in carrying or transporting a compound useful within the invention within or to the patient such that it may perform its intended function. Typically, such constructs are carried or transported from one organ, or portion of the body, to another organ, or portion of the body. Each carrier must be "acceptable" in the sense of being compatible with the other ingredients of the formulation, including the compound useful within the invention, and not injurious to the patient. Some examples of materials that may serve as pharmaceutically acceptable carriers include: sugars, such as lactose, glucose and sucrose; starches, such as corn starch and potato starch; cellulose, and its derivatives, such as sodium carboxymethyl cellulose, ethyl cellulose and cellulose acetate; powdered tragacanth; malt; gelatin; talc; excipients, such as cocoa butter and suppository waxes; oils, such as peanut oil, cottonseed oil, safflower oil, sesame oil, olive oil, corn oil and soybean oil; glycols, such as propylene glycol; polyols, such as glycerin, sorbitol, mannitol and polyethylene glycol; esters, such as ethyl oleate and ethyl laurate; agar; buffering agents, such as magnesium hydroxide and aluminum hydroxide; surface active agents; alginic acid; pyrogen-free water; isotonic saline; Ringer's solution; ethyl alcohol; phosphate buffer solutions; and other non-toxic compatible substances employed in pharmaceutical formulations. As used herein, "pharmaceutically acceptable carrier" also includes any and all coatings, antibacterial and antifungal agents, and absorption delaying agents, and the like that are compatible with the activity of the compound useful within the invention, and are physiologically acceptable to the patient. Supplementary active compounds may also be incorporated into the compositions. The "pharmaceutically acceptable carrier" may further include a pharmaceutically acceptable salt of the compound useful within the invention. Other additional ingredients that can be included in the pharmaceutical compositions used in the practice of the invention are known in the art and described, for example in Remington's Pharmaceutical Sciences (Genaro, Ed., Mack Publishing Co., 1985, Easton, Pa.), which is incorporated herein by reference.

As used herein, the language "pharmaceutically acceptable salt" refers to a salt of the administered compounds prepared from pharmaceutically acceptable non-toxic acids, including inorganic acids, organic acids, solvates, hydrates, or clathrates thereof.

The term "prevent," "preventing" or "prevention," as used herein, means avoiding or delaying the onset of symptoms associated with a disease or condition in a subject that has not developed such symptoms at the time the administering of an agent or compound commences.

A "therapeutic" treatment is a treatment administered to a subject who exhibits signs of pathology, for the purpose of diminishing or eliminating those signs.

As used herein, the term "therapeutically effective amount" refers to an amount that is sufficient or effective to prevent or treat (delay or prevent the onset of, prevent the progression of, inhibit, decrease or reverse) a disease or condition described or contemplated herein, including alleviating symptoms of such disease or condition.

As used herein, the term "treatment" or "treating" is defined as the application or administration of a therapeutic agent, i.e., a compound of the invention (alone or in combination with another pharmaceutical agent), to a patient, or application or administration of a therapeutic agent to an isolated tissue or cell line from a patient (e.g., for diagnosis or ex vivo applications), who has a condition contemplated herein, a symptom of a condition contemplated herein or the potential to develop a condition contemplated herein, with the purpose to cure, heal, alleviate, relieve, alter, remedy, ameliorate, improve or affect a condition contemplated herein, the symptoms of a condition contemplated herein or the potential to develop a condition contemplated herein. Such treatments may be specifically tailored or modified, based on knowledge obtained from the field of pharmacogenomics.

As used herein, the term "alkenyl," employed alone or in combination with other terms, means, unless otherwise stated, a stable monounsaturated or di-unsaturated straight chain or branched chain hydrocarbon group having the stated number of carbon atoms. Examples include vinyl, propenyl (or allyl), crotyl, isopentenyl, butadienyl, 1,3-pentadienyl, 1,4-pentadienyl, and the higher homologs and isomers. A functional group representing an alkene is exemplified by —$CH_2$—CH=$CH_2$.

As used herein, the term "alkoxy" employed alone or in combination with other terms means, unless otherwise stated, an alkyl group having the designated number of carbon atoms, as defined elsewhere herein, connected to the rest of the molecule via an oxygen atom, such as, for example, methoxy, ethoxy, 1-propoxy, 2-propoxy (or isopropoxy) and the higher homologs and isomers. A specific example is ($C_1$-$C_3$)alkoxy, such as, but not limited to, ethoxy and methoxy.

As used herein, the term "alkyl" by itself or as part of another substituent means, unless otherwise stated, a straight or branched chain hydrocarbon having the number of carbon atoms designated (i.e., $C_1$-$C_{10}$ means one to ten carbon atoms) and includes straight, branched chain, or cyclic substituent groups. Examples include methyl, ethyl, propyl, isopropyl, butyl, isobutyl, tert-butyl, pentyl, neopentyl, hexyl, and cyclopropylmethyl. A specific embodiment is ($C_1$-$C_6$)alkyl, such as, but not limited to, ethyl, methyl, isopropyl, isobutyl, n-pentyl, n-hexyl and cyclopropylmethyl.

As used herein, the term "alkynyl," employed alone or in combination with other terms, means, unless otherwise stated, a stable straight chain or branched chain hydrocarbon group with a triple carbon-carbon bond, having the stated number of carbon atoms. Non-limiting examples include ethynyl and propynyl, and the higher homologs and isomers. The term "propargylic" refers to a group exemplified by —$CH_2$—C≡CH. The term "homopropargylic" refers to a group exemplified by —$CH_2CH_2$—C≡CH. The term "substituted propargylic" refers to a group exemplified by —$CR_2$—C≡CR', wherein each occurrence of R' is independently H, alkyl, substituted alkyl, alkenyl or substituted alkenyl, with the proviso that at least one R' group is not hydrogen. The term "substituted homopropargylic" refers to a group exemplified by —$CR'_2CR'_2$—C≡CR', wherein each occurrence of R' is independently H, alkyl, substituted alkyl, alkenyl or substituted alkenyl, with the proviso that at least one R' group is not hydrogen.

As used herein, the term "aromatic" refers to a carbocycle or heterocycle with one or more polyunsaturated rings and having aromatic character, i.e. having (4n+2) delocalized π (pi) electrons, where n is an integer.

As used herein, the term "cycloalkyl" by itself or as part of another substituent refers to, unless otherwise stated, a cyclic chain hydrocarbon having the number of carbon atoms designated (i.e., $C_3$-$C_6$ refers to a cyclic group comprising a ring group consisting of three to six carbon atoms) and includes straight, branched chain or cyclic substituent groups. Examples of ($C_3$-$C_6$)cycloalkyl groups are cyclopropyl, cyclobutyl, cyclopentyl and cyclohexyl. Cycloalkyl rings can be optionally substituted. Non-limiting examples of cycloalkyl groups include: cyclopropyl, 2-methyl-cyclopropyl, cyclopropenyl, cyclobutyl, 2,3-dihydroxycyclobutyl, cyclobutenyl, cyclopentyl, cyclopentenyl, cyclopentadienyl, cyclohexyl, cyclohexenyl, cycloheptyl, cyclooctanyl, decalinyl, 2,5-dimethylcyclopentyl, 3,5-dichlorocyclohexyl, 4-hydroxycyclohexyl, 3,3,5-trimethylcyclohex-1-yl, octahydropentalenyl, octahydro-1H-indenyl, 3a,4,5,6,7,7a-hexahydro-3H-inden-4-yl, decahydroazulenyl; bicyclo[6.2.0]decanyl, decahydronaphthalenyl, and dodecahydro-1H-fluorenyl. The term "cycloalkyl" also includes bicyclic hydrocarbon rings, non-limiting examples of which include, bicyclo-[2.1.1]hexanyl, bicyclo[2.2.1]heptanyl, bicyclo[3.1.1]heptanyl, 1,3-dimethyl[2.2.1] heptan-2-yl, bicyclo[2.2.2]octanyl, and bicyclo[3.3.3]undecanyl.

As used herein, the term "halide" refers to a halogen atom bearing a negative charge. The halide anions are fluoride ($F^-$), chloride ($Cl^-$), bromide ($Br^-$), and iodide ($I^-$).

As used herein, the term "halo" or "halogen" alone or as part of another substituent refers to, unless otherwise stated, a fluorine, chlorine, bromine, or iodine atom.

As used herein, the term "heteroalkyl" by itself or in combination with another term refers to, unless otherwise stated, a stable straight or branched chain alkyl group consisting of the stated number of carbon atoms and one or two heteroatoms selected from the group consisting of O, N, and S, and wherein the nitrogen and sulfur atoms may be optionally oxidized and the nitrogen heteroatom may be optionally quaternized. The heteroatom(s) may be placed at any position of the heteroalkyl group, including between the rest of the heteroalkyl group and the fragment to which it is attached, as well as attached to the most distal carbon atom in the heteroalkyl group. Examples include: —O—$CH_2$—$CH_2$—$CH_3$, —$CH_2$—$CH_2$—$CH_2$—OH, —$CH_2$—$CH_2$—NH—$CH_3$, —$CH_2$—S—$CH_2$—$CH_3$, and —$CH_2CH_2$—S (=O)—$CH_3$. Up to two heteroatoms may be consecutive, such as, for example, —$CH_2$—NH—$OCH_3$, or —$CH_2$—$CH_2$—S—S—$CH_3$.

As used herein, the term "heterocycle" or "heterocyclyl" or "heterocyclic" by itself or as part of another substituent refers to, unless otherwise stated, an unsubstituted or substituted, stable, mono- or multi-cyclic heterocyclic ring system that consists of carbon atoms and at least one heteroatom selected from the group consisting of N, O, and S, and wherein the nitrogen and sulfur heteroatoms may be optionally oxidized, and the nitrogen atom may be optionally quaternized. The heterocyclic system may be attached, unless otherwise stated, at any heteroatom or carbon atom that affords a stable structure. A heterocycle may be aromatic or non-aromatic in nature. In certain embodiments, the heterocycle is a heteroaryl.

As used herein, the term "heteroaryl" or "heteroaromatic" refers to a heterocycle having aromatic character. A polycyclic heteroaryl may include one or more rings that are partially saturated. Examples include tetrahydroquinoline and 2,3-dihydrobenzofuryl.

Examples of non-aromatic heterocycles include monocyclic groups such as aziridine, oxirane, thiirane, azetidine, oxetane, thietane, pyrrolidine, pyrroline, imidazoline, pyrazolidine, dioxolane, sulfolane, 2,3-dihydrofuran, 2,5-dihydrofuran, tetrahydrofuran, thiophane, piperidine, 1,2,3,6-tetrahydropyridine, 1,4-dihydropyridine, piperazine, morpholine, thiomorpholine, pyran, 2,3-dihydropyran, tetrahydropyran, 1,4-dioxane, 1,3-dioxane, homopiperazine, homopiperidine, 1,3-dioxepane, 4,7-dihydro-1,3-dioxepin and hexamethyleneoxide.

Examples of heteroaryl groups include pyridyl, pyrazinyl, pyrimidinyl (such as, but not limited to, 2- and 4-pyrimidinyl), pyridazinyl, thienyl, furyl, pyrrolyl, imidazolyl, thiazolyl, oxazolyl, pyrazolyl, isothiazolyl, 1,2,3-triazolyl, 1,2,4-triazolyl, 1,3,4-triazolyl, tetrazolyl, 1,2,3-thiadiazolyl, 1,2,3-oxadiazolyl, 1,3,4-thiadiazolyl and 1,3,4-oxadiazolyl.

Examples of polycyclic heterocycles include indolyl (such as, but not limited to, 3-, 4-, 5-, 6- and 7-indolyl), indolinyl, quinolyl, tetrahydroquinolyl, isoquinolyl (such as, but not limited to, 1- and 5-isoquinolyl), 1,2,3,4-tetrahydroisoquinolyl, cinnolinyl, quinoxalinyl (such as, but not limited to, 2- and 5-quinoxalinyl), quinazolinyl, phthalazinyl, 1,8-naphthyridinyl, 1,4-benzodioxanyl, coumarin, dihydrocoumarin, 1,5-naphthyridinyl, benzofuryl (such as, but not limited to, 3-, 4-, 5-, 6- and 7-benzofuryl), 2,3-dihydrobenzofuryl, 1,2-benzisoxazolyl, benzothienyl (such as, but not limited to, 3-, 4-, 5-, 6-, and 7-benzothienyl), benzoxazolyl, benzothiazolyl (such as, but not limited to, 2-benzothiazolyl and 5-benzothiazolyl), purinyl, benzimidazolyl, benztriazolyl, thioxanthinyl, carbazolyl, carbolinyl, acridinyl, pyrrolizidinyl, and quinolizidinyl.

The aforementioned listing of heterocyclic and heteroaryl moieties is intended to be representative and not limiting.

As used herein, the term "substituted" refers to that an atom or group of atoms has replaced hydrogen as the substituent attached to another group.

As used herein, the term "substituted alkyl," "substituted cycloalkyl," "substituted alkenyl" or "substituted alkynyl" refers to alkyl, cycloalkyl, alkenyl or alkynyl, as defined above, substituted by one, two or three substituents selected from the group consisting of halogen, —OH, alkoxy, tetrahydro-2-H-pyranyl, —NH$_2$, —N(CH$_3$)$_2$, (1-methyl-imidazol-2-yl), pyridin-2-yl, pyridin-3-yl, pyridin-4-yl, —C(=O)OH, trifluoromethyl, —C≡N, —C(=O)O(C$_1$-C$_4$)alkyl, —C(=O)NH$_2$, —C(=O)NH(C$_1$-C$_4$)alkyl, —C(=O)N((C$_1$-C$_4$)alkyl)$_2$, —SO$_2$NH$_2$, —C(=NH)NH$_2$, and —NO$_2$, preferably containing one or two substituents selected from halogen, —OH, alkoxy, —NH$_2$, trifluoromethyl, —N(CH$_3$)$_2$, and —C(=O)OH, more preferably selected from halogen, alkoxy and —OH. Examples of substituted alkyls include, but are not limited to, 2,2-difluoropropyl, 2-carboxycyclopentyl and 3-chloropropyl.

For aryl, aryl-(C$_1$-C$_3$)alkyl and heterocyclyl groups, the term "substituted" as applied to the rings of these groups refers to any level of substitution, namely mono-, di-, tri-, tetra-, or penta-substitution, where such substitution is permitted. The substituents are independently selected, and substitution may be at any chemically accessible position. In certain embodiments, the substituents vary in number between one and four. In another embodiment, the substituents vary in number between one and three. In yet another embodiment, the substituents vary in number between one and two. In yet another embodiment, the substituents are independently selected from the group consisting of C$_{1-6}$ alkyl, —OH, C$_{1-6}$ alkoxy, halo, amino, acetamido and nitro. As used herein, where a substituent is an alkyl or alkoxy group, the carbon chain may be branched, straight or cyclic.

Unless otherwise noted, when two substituents are taken together to form a ring having a specified number of ring atoms (e.g., R$^2$ and R$^3$ taken together with the nitrogen to which they are attached to form a ring having from 3 to 7 ring members), the ring can have carbon atoms and optionally one or more (e.g., 1 to 3) additional heteroatoms independently selected from nitrogen, oxygen, or sulfur. The ring can be saturated or partially saturated, and can be optionally substituted.

Whenever a term or either of their prefix roots appear in a name of a substituent the name is to be interpreted as including those limitations provided herein. For example, whenever the term "alkyl" or "aryl" or either of their prefix roots appear in a name of a substituent (e.g., arylalkyl, alkylamino) the name is to be interpreted as including those limitations given elsewhere herein for "alkyl" and "aryl" respectively.

In certain embodiments, substituents of compounds are disclosed in groups or in ranges. It is specifically intended that the description include each and every individual sub-combination of the members of such groups and ranges. For example, the term "C$_{1-6}$ alkyl" is specifically intended to individually disclose C$_1$, C$_2$, C$_3$, C$_4$, C$_5$, C$_6$, C$_1$-C$_6$, C$_1$-C$_5$, C$_1$-C$_4$, C$_1$-C$_3$, C$_1$-C$_2$, C$_2$-C$_6$, C$_2$-C$_5$, C$_2$-C$_4$, C$_2$-C$_3$, C$_3$-C$_6$, C$_3$-C$_5$, C$_3$-C$_4$, C$_4$-C$_6$, C$_4$-C$_5$, and C$_5$-C$_6$ alkyl.

Ranges: throughout this disclosure, various aspects of the invention can be presented in a range format. It should be understood that the description in range format is merely for convenience and brevity and should not be construed as an inflexible limitation on the scope of the invention. Accordingly, the description of a range should be considered to have specifically disclosed all the possible sub-ranges as well as individual numerical values within that range. For example, description of a range such as from 1 to 6 should be considered to have specifically disclosed sub-ranges such as from 1 to 3, from 1 to 4, from 1 to 5, from 2 to 4, from 2 to 6, from 3 to 6 etc., as well as individual and partial numbers within that range, for example, 1, 2, 2.7, 3, 4, 5, 5.3, and 6. This applies regardless of the breadth of the range.

The following abbreviations are used herein: 2-DG: 2-deoxyglucose; ADP: Adenosine diphosphate; AMP: Adenosine monophosphate; AMPK: 5' AMP-activated protein kinase; AMP-PNP: Adenylyl-imidodiphosphate; ATP: Adenosine triphosphate; BCA: bicinchoninic acid; BSA: bovine serum albumin; CHAPS: 3-[(3-Cholamidopropyl)dimethylammonio]-1-propanesulfonate; DAG: diacylglycerol; DCFDA: 2',7'-dichlorofluorescin diacetate; DMSO: dimethylsulfoxide; DPBS: Dulbecco's phosphate-buffered saline; DTT: dithiothreitol; HEPES: 4-(2-hydroxyethyl)-1-piperazineethanesulfonic acid; IP$_3$: inositol 1,4,5-trisphosphate; kDa: kiloDalton; KRH: Krebs-Ringer-HEPES-bicarbonate buffer; LC-MS: liquid chromatography-mass spectrometry; NAC: N-acetyl cysteine; PBS: phosphate buffered saline; PIP$_3$: phosphatidylinositol 3,4,5-trisphosphate; ROS: reactive oxygen species; RT: room temperature; TLC: thin layer chromatography; TNP-ATP: 2,4,6-trinitrophenol-adenosine triphosphate.

Those skilled in the art will recognize, or be able to ascertain using no more than routine experimentation, numerous equivalents to the specific procedures, embodiments, claims, and examples described herein. Such equivalents were considered to be within the scope of this invention and covered by the claims appended hereto. For example, it should be understood, that modifications in reaction conditions, including but not limited to reaction times, reaction size/volume, and experimental reagents, such as solvents, catalysts, pressures, atmospheric conditions, e.g., nitrogen atmosphere, and reducing/oxidizing agents, with art-recognized alternatives and using no more than routine experimentation, are within the scope of the present application.

It is to be understood that, wherever values and ranges are provided herein, the description in range format is merely for convenience and brevity and should not be construed as an inflexible limitation on the scope of the invention. Accordingly, all values and ranges encompassed by these values and ranges are meant to be encompassed within the scope of the present invention. Moreover, all values that fall within these ranges, as well as the upper or lower limits of a range of values, are also contemplated by the present application. The description of a range should be considered to have specifically disclosed all the possible sub-ranges as well as individual numerical values within that range and, when appropriate, partial integers of the numerical values within ranges. For example, description of a range such as from 1 to 6 should be considered to have specifically disclosed sub-ranges such as from 1 to 3, from 1 to 4, from 1 to 5, from 2 to 4, from 2 to 6, from 3 to 6 etc., as well as individual numbers within that range, for example, 1, 2, 2.7, 3, 4, 5, 5.3, and 6. This applies regardless of the breadth of the range.

The following examples further illustrate aspects of the present invention. However, they are in no way a limitation of the teachings or disclosure of the present invention as set forth herein.

EXAMPLES

The invention is now described with reference to the following Examples. These Examples are provided for the purpose of illustration only, and the invention is not limited to these Examples, but rather encompasses all variations that are evident as a result of the teachings provided herein.

Materials and Methods
Chemicals and Reagents

BI-D1870, BI-2536, volasertib, palbociclib hydrochloride, GDC-0941, SAR405 were purchased from Cayman Chemical. Insulin was purchased from Sigma Aldrich. Rapamycin and metformin hydrochloride were purchased from Abcam. N-acetyl-L-cysteine (NAC) was purchased from MP Biomedical. 1,2-dipalmitoyl-sn-glycero-3-phosphoserine, or DPPS, and D-myo-phosphatidylinositol 5-phosphate diCl6, or PI(5)P, were purchased from Echelon Biosciences.

High-Throughput Screen

Four compound libraries were screened at the Yale Center for Molecular Discovery. Lipid vesicles [2:1 mixture of DPPS and PI(5)P] were prepared by sonication and extrusion in a buffer containing 0.1% CHAPS, 20 mM HEPES pH 7.3, 200 mM NaCl, 20 mM $MgCl_2$, aliquoted, and stored at −80° C. Immediately before assay, thawed lipid suspension was sonicated and extruded again, and mixed with PI5P4Kα freshly purified in the same buffer. 9 μl lipid/kinase mixture was dispensed into each well of a white solid-bottom 384-well plate (Corning 3574). 20 nl of library compound (10 mM DMSO solution) was transferred to the well by an Aquarius system (Tecan). The plates were shaken for 30 s. 1 μl ATP solution was then added to initiate the reaction (final concentrations: PI(5)P 100 μM; lipid kinase 2 μg/ml; ATP 40 μM; library compound 20 μM). After incubating at RT in the dark for 1 h, 5 μl ADP-Glom reagent (Promega) was added to stop the reaction. After 40 min further incubation, 10 μl Kinase Detection reagent (Promega) was added. After 30 min, the luminescence was measured with an EnVision Multimode Plate Reader.

Enzymatic and Fluorescent Binding Assays

In vitro kinase assay based on ADP (product) detection was performed similarly in a white solid-bottom 96-well plate (Corning 3600). Within each well, 10 μl final reaction mixture contains 100 μM PI(5)P, 2 μg/ml PI5P4Kα, 10 μM ATP (in FIG. 1B, ATP concentration varied from 10 μM to 100 μM), 10 mM $MgCl_2$, 0.1% CHAPS and 20 mM HEPES pH 7.3. After reaction, 10 μl ADP-Glo™ reagent and 20 μl Kinase Detection reagent were used for luminescence reading. Kinase assay based on $PI(4,5)P_2$ (product) detection was carried out in a 50 μl assay mixture containing 40 μM PI(5)P, 0.4 μg/ml PI5P4Kα, 20 μM ATP (unless otherwise stated), 10 mM $MgCl_2$, 20 mM HEPES pH 7.3, and 10 mCi [γ-$^{32}$P]-ATP for 1 h at RT. For PI5P4Kβ, which is less active, the reaction was carried out with 4 μg/ml enzyme for 3 h. The reaction was terminated by 5 μl 12N HCl. After termination, 175 μl PBS buffer and 380 μl methanol/chloroform mix (1:1, v/v) containing 10 μg/ml bovine brain extract (type I; Folch Fraction I; Sigma Aldrich) were added. The lower organic phase, containing the extracted lipids, was collected and dried under vacuum. The dried lipids were re-suspended in 25 μl methanol/chloroform mix (2:1, v/v), and separated by thin-layer chromatography (TLC). For TLC, heat activated 1% potassium oxalate-coated silica gel 60 plates were used (20 cm×20 cm, Merck), and the running solvent contained water, acetic acid, methanol, acetone, and chloroform (3:32:24:30:64 mix by volume). Radiolabeled lipid product was quantified with a phosphor imager (Bio-Rad Molecular Imager FX). BI-D1870, BI-2536, volasertib and palbociclib were purchased from Cayman Chemical. Except for palbociclib, which was dissolved in water, all commercial and synthesized inhibitors were dissolved in DMSO as 10 mM stock solutions and stored at −80° C. The inhibitor was usually incubated with the enzyme at RT for 20 min before the reaction was initiated.

A competitive binding assay was employed to directly measure the $K_d$ of BI-D1870 for PI5P4Kα. Different amounts of kinase were mixed with 6 μM TNP-ATP (a fluorescent ATP analog) in a buffer containing 20 mM Tris HCl pH 7.4, 500 mM NaCl, 10 mM $MgCl_2$, 5 mM DTT, 2% DMSO (total volume 100 μl). Samples were gently shaken for 20 min on an orbital shaker at RT and read from a black solid-bottom 96-well plate (Corning 3650) using Spectra-Max M5 plate reader (excitation 410 nm; emission 540 nm). The change in fluorescence was used to determine $K_d$ for TNP-ATP (13 μM). Increasing amounts of BI-D1870 were then added to a mixture of 6.8 μM PI5P4Kα and 10 μM TNP-ATP in the same buffer. The $K_d$ was calculated to be ~1.3 μM.

Chemical Synthesis and Characterization

Unless otherwise noted, all reagents were obtained from commercial suppliers and used without further purification. Reaction progress was monitored by UV/MS on an Agilent 6120 Quadrupole HPLC/MSD and Agilent 1260 Infinity. Organic extracts were dried over $MgSO_4$ and then concentrated under reduced pressure. Flash-column chromatography was performed on a Teledyne ISCO automated chromatography system using either normal phase RediSep Rf silica gel cartridges or reverse phase RediSep Rf 50 g C18 silica gel cartridges. Methanol-$d_4$ and Chloroform-$d_3$ were obtained from commercial sources and used as received. NMR chemical shifts are reported in ppm relative to $CD_3OD$ (3.31, 4.78 ppm $^1H$ and 49.0 ppm $^{13}C$) and $CDCl_3$ (1.56, 7.26 ppm $^1H$ and 77.16 ppm $^{13}C$). HRMS were obtained on an Agilent 6550 iFunnel QTOF LCMS.

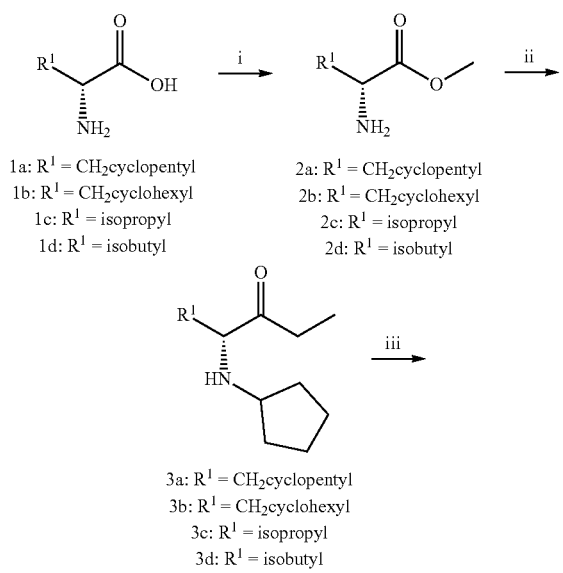

35
-continued

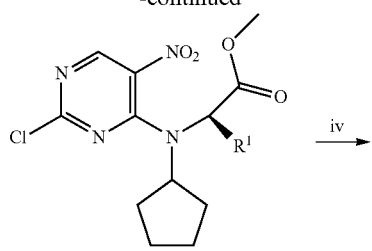

4a: R¹ = CH₂cyclopentyl
4b: R¹ = CH₂cyclohexyl
4c: R¹ = isopropyl
4d: R¹ = isobutyl iv →

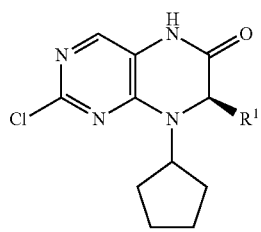

5a: R¹ = CH₂cyclopentyl
5b: R¹ = CH₂cyclohexyl
5c: R¹ = isopropyl
5d: R¹ = isobutyl v →

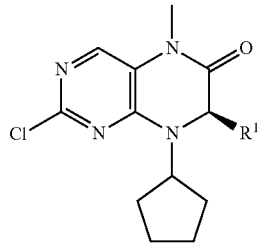

6a: R¹ = CH₂cyclopentyl
6b: R¹ = CH₂cyclohexyl
6c: R¹ = isopropyl
6d: R¹ = isobutyl v →

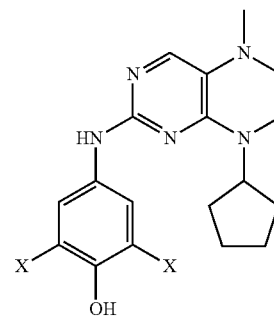

7a: R¹ = CH₂cyclopentyl, X = Cl
7b: R¹ = CH₂cyclohexyl, X = Cl
7c: R¹ = isopropyl, X = F
7d: R¹ = isobutyl, X = Cl

36

(R)-8-cyclopentyl-7-(cyclopentylmethyl)-2-((3,5-dichloro-4-hydroxyphenyl)amino)-5-methyl-7,8-dihydropteridin-6(5H)-one (7a)

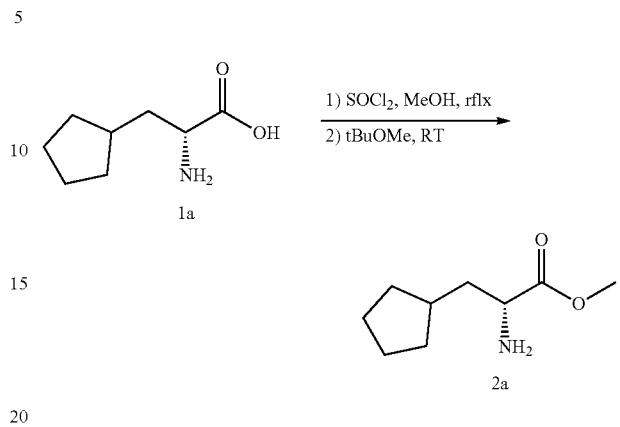

To a round bottom flask equipped with a stir bar was added 1a (3.00 g, 19.1 mmol) in methanol (19 mL). The solution was cooled to 0° C., and SOCl₂ (2.90 mL, 40.1 mmol) was added dropwise. The reaction mixture was then refluxed for 2 h and then concentrated. The remaining oil was diluted with tert-butyl methyl ether (20 mL) and stirred for 30 min at rt. The precipitate was filtered and washed with diethyl ether and dried under vacuum to give 2a (3.77 g, quant.). The product was used in the next step without further purification.

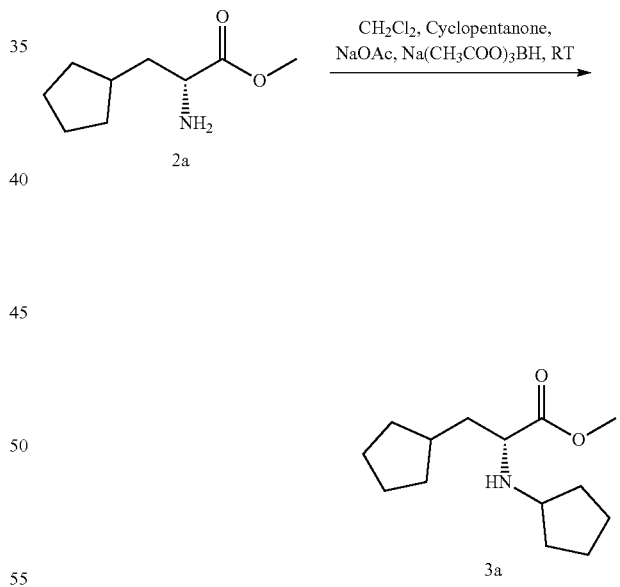

Methyl ester 2a (3.77 g, 22 mmol) was dissolved in CH₂Cl₂ (37 mL) and cooled to 0° C. Cyclopentanone (4.87 mL, 55 mmol), sodium acetate (1.86 g, 22.7 mmol), and sodium triacetoxyborohydride (6.90 g, 32.6 mmol) were subsequently added to the solution. The reaction mixture was stirred and allowed to warm to rt over 1 h. The reaction mixture was diluted with sat. NaHCO₃ and extracted with CH₂Cl₂. The organics were washed with water, dried, and concentrated to afford 3a (4.95 g, quant.) which was used in the next step without further purification.

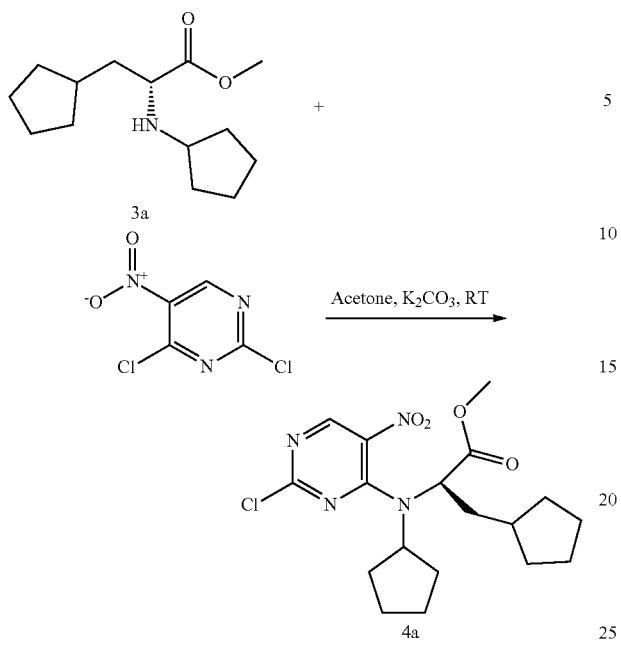

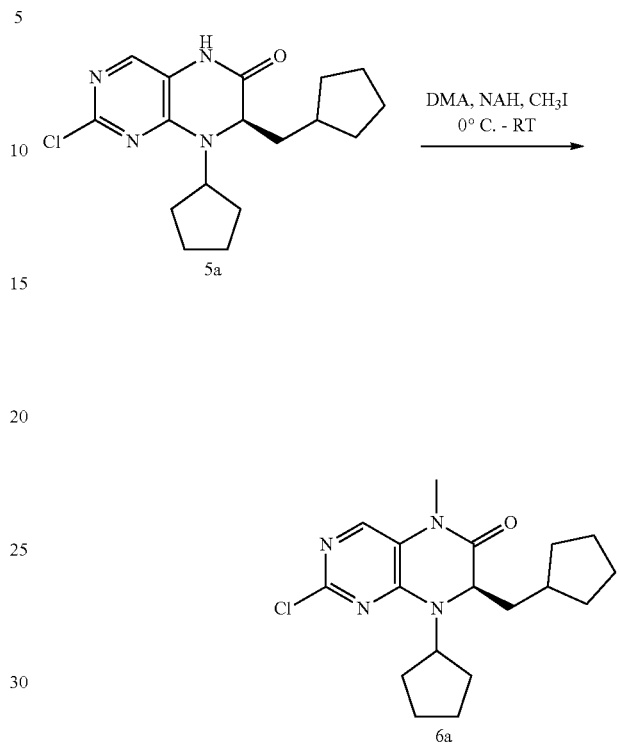

centration, the crude product was purified by silica gel column chromatography eluting with ethyl acetate in hexane to give 5a (1.40 g, 84.1%).

To a flame dried and N₂ flushed round bottom flask was added 3a (4.81 g, 20.1 mmol) dissolved in dry acetone (50 mL). The solution was cooled to 0° C., and then K₂CO₃ (3.06 g, 22.1 mmol) and 2,4-dichloro-5-nitropyrimidine (4.29 g, 22.1 mmol dissolved in acetone) were added. The reaction mixture was stirred overnight at rt. Solvent was removed under reduced pressure. The residue was washed with water, extracted with ethyl acetate, dried and concentrated. The crude product was purified by silica gel column chromatography eluting with ethyl acetate in hexane to give 4a (2.01 g, 25.3%). The product was however still contaminated with some impurities that were removed during purification the next step.

To a round bottom flask equipped with a stir bar and cooled to 0° C. was added 5a (1.40 g, 4.18 mmol) in DMA (10 mL). NaH (125 mg, 5.43 mmol, 60% dispersion in mineral oil) and CH₃I (340 μL, 5.43 mmol) were subsequently added. The reaction mixture was stirred for 30 min at 0° C., and then for 2.5 h at rt. The reaction was then quenched with cooled water, and the resulting mixture was extracted with ethyl acetate. The residue was washed with water three times. The organics was dried and concentrated. The crude product was purified by silica gel column chromatography eluting with ethyl acetate in hexane to afford 6a (1.00 g, 72.8%).

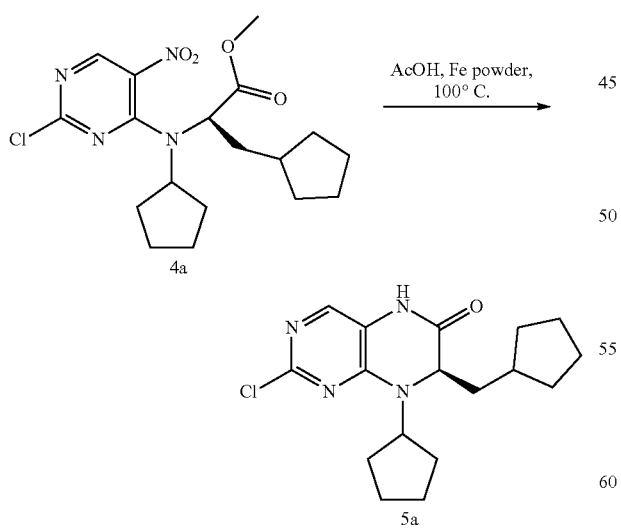

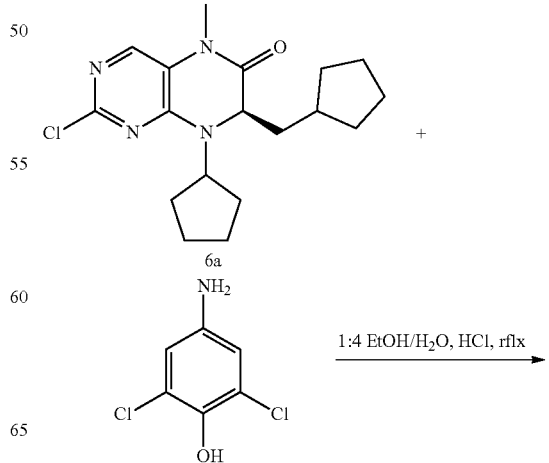

Next, 4a (2.01 g, 5.08 mmol) was dissolved in glacial acetic acid (11.5 mL) and reacted with Fe powder (696 mg, 12.5 mmol). The reaction mixture was stirred for 4 h at 100° C. The solution was filtered through celite, and after con-

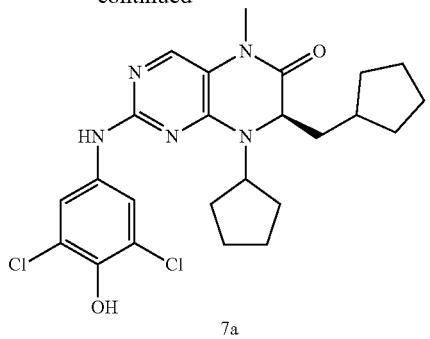

7a

The methylated pteridine intermediate 6a (330 mg, 1.0 mmol) and 4-amino-2,6-dichloro phenol (279 mg, 1.57 mmol) were suspended in a 1:4 mixture of ethanol and water. To this mixture was added conc. HCl (181 μL, 2.11 mmol), and the reaction mixture was refluxed overnight. The mixture was cooled down to rt, and the volatiles were evaporated. The crude product was then purified by reverse phase chromatography (gradient elution: 10-100% MeCN in H$_2$O+0.1% TFA) to yield 7a (380 mg, 77.1%) upon lyophilization.

Characterization of 7a by NMR and MS: $^1$H NMR (400 MHz, CD$_3$OD) δ (7.51 (s, 1H), 7.43 (s, 2H), 4.42 (dd, J=8.2, 3.7 Hz, 1H), 4.26 (p, J=8.8 Hz, 1H), 3.27 (s, 3H), 2.12-1.44 (m, 17H), 1.12 (m, 2H). $^{13}$C NMR (101 MHz, CD$_3$OD) δ (164.69, 154.38, 151.39, 149.35, 130.37, 126.01, 124.62, 123.59, 117.91, 63.20, 62.06, 41.01, 36.86, 34.58, 33.05, 29.79, 29.65, 28.93, 26.29, 25.83, 24.45, 24.38. HRMS-ESI (m z): [M+H]$^+$ calcd. for C$_{24}$H$_{29}$Cl$_2$N$_5$O$_2$, 490.1776, found 490.1776.

(R)-7-(cyclohexylmethyl)-8-cyclopentyl-2-((3,5-dichloro-4-hydroxyphenyl)amino)-5-methyl-7,8-dihydropteridin-6(5H)-one (7b)

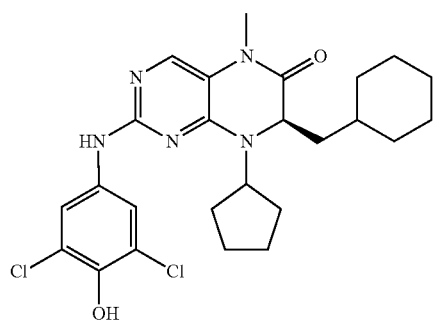

7b 7b was prepared in a similar manner as described for 7a using 1b (3.0 g, 17.5 mmol) to give 2b (2.98 g, quant.). The entire amount of 2b was converted to 3b (4.18 g. quant.). The S$_N$Ar reaction of 3b yielded 4b (2.49 g, 36.7%), which upon cyclization and methylation afforded 5b (1.49 g, 70.5%) and 6b (1.17 g, 75.5%), respectively. A portion of 6b (200 mg, 0.551 mmol) was taken forward to give 254 mg of 7b in 91.4% yield after purification by reverse phase chromatography (gradient elution: 10-100% MeCN in H$_2$O+ 0.1% TFA) and lyophilization.

Characterization of 7b by NMR and MS: $^1$H NMR (500 MHz, CD$_3$OD) δ (7.55 (s, 1H), 7.44 (s, 2H), 4.44 (dd, J=9.7, 4.0 Hz, 1H), 4.38-4.27 (m, 1H), 3.28 (s, 3H), 2.09-1.80 (m, 5H), 1.76-1.51 (m, 10H), 1.44-1.33 (m, 1H), 1.30-1.10 (m, 3H), 1.03-0.87 (m, 2H). $^{13}$C NMR (151 MHz, CD$_3$OD) δ (164.55, 154.53, 151.37, 149.04, 130.56, 125.50, 125.16, 123.53, 117.90, 62.68, 59.95, 42.73, 35.23, 35.21, 33.35, 30.12, 29.91, 28.98, 27.35, 27.28, 27.05, 24.49, 24.24. HRMS-ESI (m z): [M+H]$^+$ calcd. for C$_{25}$H$_{31}$Cl$_2$N$_5$O$_2$, 504.1933, found 504.1919.

(R)-8-cyclopentyl-2-((3,5-dichloro-4-hydroxyphenyl)amino)-7-isobutyl-5-methyl-7,8-dihydropteridin-6(5H)-one (7c)

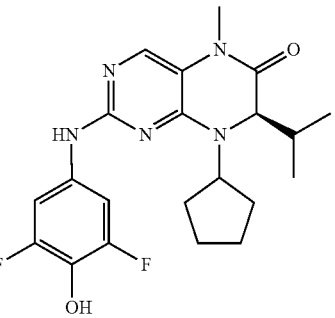

7c 7c was prepared in a similar manner as described for 7a using 1c (12 g, 91.5 mmol) to give 2c (15.9 g, quant.). The entire amount of 2c was converted to 3c (21.5 g, quant.). The S$_N$Ar reaction of 3c yielded 4c (6.26 g, 16.7%), which upon cyclization and methylation afforded 5c (2.16 g, 41.4%) and 6c (1.17 g, 51.8%), respectively. A portion of 6c (506 mg, 1.57 mmol) was taken forward to give 690 mg of 7c in 94.8% yield after purification by reverse phase chromatography (gradient elution: 10-100% MeCN in H$_2$O+0.1% TFA) and lyophilization.

Characterization of 7c by NMR and MS: H NMR (400 MHz, CD$_3$OD) δ (7.67 (s, 1H), 7.54 (s, 2H), 4.44 (p, J=7.7 Hz, 1H), 4.32 (dd, J=10.0, 3.9 Hz, 1H), 3.29 (s, 3H), 2.14-1.96 (m, 2H), 1.88-1.58 (m, 8H), 1.52 (m, 1H), 1.00 (d, J=6.3 Hz, 3H), 0.88 (d, J=6.5 Hz, 3H). $^{13}$C NMR (151 MHz, CD$_3$OD) δ (164.69, 154.31, 152.83, 147.92, 131.88, 129.17, 124.07, 123.41, 117.64, 61.88, 60.00, 43.60, 30.23, 30.10, 28.91, 25.85, 24.43, 24.13, 24.03, 21.81. HRMS-ESI (m z): [M+H]$^+$ calcd. for C$_{22}$H$_{27}$Cl$_2$N$_5$O$_2$, 464.1620, found 464.1607.

(R)-8-cyclopentyl-2-((3,5-dichloro-4-hydroxyphenyl)amino)-7-isopropyl-5-methyl-7,8-dihydropteridin-6(5H)-one (7d)

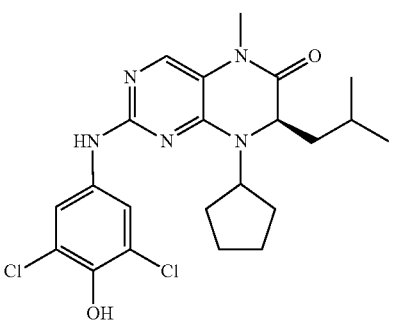

7d 7d was prepared in a similar manner as described for 7a using 1d (1.0 g, 8.54 mmol) to give 2d (1.01 g, quant.). The entire amount of 2d was converted to 3d (810 mg, quant.). The $S_NAr$ reaction of 3d yielded 4d (220 mg, 15.2%), which upon cyclization and methylation afforded 5d (110 mg, 60.5%) and 6d (40 mg, 34.7%), respectively. 6d (40 mg, 0.130 mmol) was reacted with 4-amino-2,6-difluorophenol (28.2 mg, 0.194 mmol) to give 11 mg of 7d in 20.3% yield after purification by reverse phase chromatography (gradient elution: 10-100% MeCN in $H_2O$+0.1% TFA) and lyophilization.

Characterization of 7d by NMR and MS: $^1$H NMR (600 MHz, $CD_3OD$) δ (7.46 (s, 1H), 7.12-7.05 (m, 2H), 4.30 (d, J=3.5 Hz, 1H), 4.19-4.12 (m, 1H), 3.28 (s, 3H), 2.30-2.21 (m, 1H), 2.10-2.00 (m, 2H), 1.97-1.88 (m, 2H), 1.72-1.61 (m, 2H), 1.60-1.51 (m, 2H), 1.13 (dd, J=6.9, 1.8 Hz, 3H), 0.79 (dd, J=6.9, 1.8 Hz, 3H). $^{19}$F NMR (470 MHz, $CD_3OD$) δ −134.57. HRMS-ESI (m z): [M+H]$^+$ calcd. for $C_{21}H_{25}F_2N_5O_2$, 418.2059; found 418.2056.

The following compounds were prepared following the experimentals illustrated elsewhere herein, and characterized by physical methods and by biological assays illustrated elsewhere herein:

(R)-8-cyclopentyl-2-((3,5-dichloro-4-hydroxyphenyl)amino)-7-(pyridine-2-ylmethyl)-5-methyl-7,8-dihydropteridin-6(5H)-one (7e)

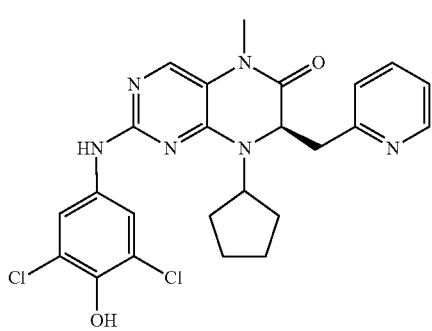

(7e)

$K_i$(PI5P4Kα)=20-60 nM
$K_i$(PI5P4Kβ)=20-60 nM (R)-2-((1H-benzo[d][1,2,3]triazol-5-yl)amino)-8-cyclopentyl-7-(cyclopentylmethyl)-5-methyl-7,8-dihydropteridin-6(5H)-one (7f)

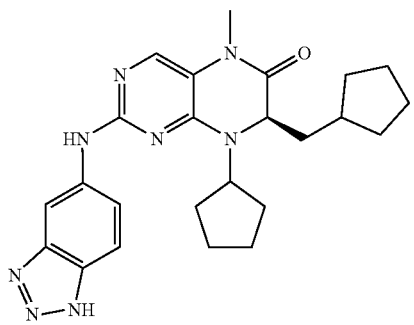

(7f)

$K_i$(PI5P4Kα)=200-700 nM
$K_i$(PI5P4Kβ)=80-230 nM (R)-2-((8-cyclopentyl-7-(cyclopentylmethyl)-5-methyl-6-oxo-5,6,7,8-tetrahydropteridin-2-yl)amino)thiazole-5-carboxylic acid (7g)

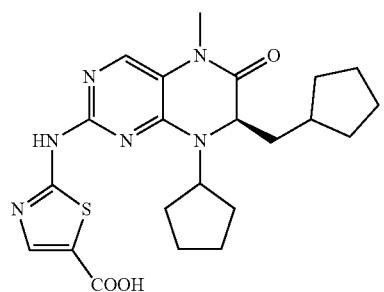

(7g)

$K_i$(PI5P4Kα)=30-90 nM
$K_i$(PI5P4Kβ)=100-280 nM (R)-4-((8-cyclopentyl-7-(cyclopentylmethyl)-5-methyl-6-oxo-5,6,7,8-tetrahydropteridin-2-yl)amino)thiophene-2-carboxylic acid (7h)

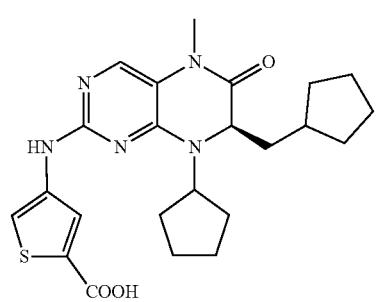

(7h)

$K_i$(PI5P4Kα)=110-220 nM
$K_i$(PI5P4Kβ)=80-160 nM (R)-4-((8-cyclopentyl-7-(cyclopentylmethyl)-5-methyl-6-oxo-5,6,7,8-tetrahydropteridin-2-yl)amino)-2,6-difluorobenzoic acid (7i)

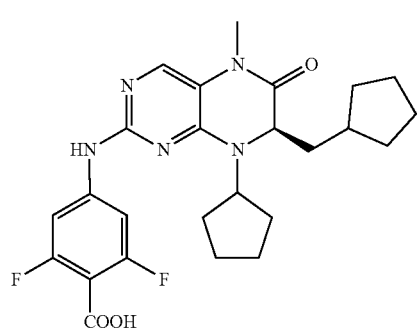

(7i)

$K_i$(PI5P4Kα)=55-110 nM
$K_i$(PI5P4Kβ)=75-150 nM (R)-2-((8-cyclopentyl-5-methyl-6-oxo-7-(pyridin-2-ylmethyl)-5,6,7,8-tetrahydropteridin-2-yl)amino)thiazole-5-carboxylic acid (7j)

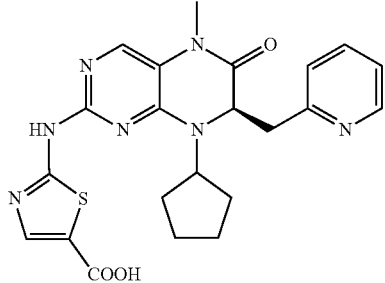

(7j)

$K_i(PI5P4K\alpha)$=50-100 nM
$K_i(PI5P4K\beta)$=400-800 nM (R)-2-((1H-benzo[d][1,2,3]triazol-5-yl)amino)-8-cyclopentyl-5-methyl-7-(pyridin-2-ylmethyl)-7,8-dihydropteridin-6(5H)-one (7k)

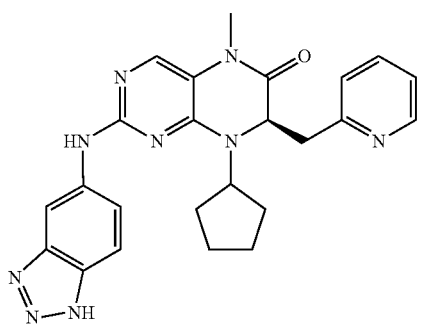

(7k)

$K_i(PI5P4K\alpha)$=130-260 nM
$K_i(PI5P4K\beta)$=100-200 nM (R)-8-cyclopentyl-2-((3,5-dichloro-4-hydroxyphenyl)amino)-5-methyl-7-(pyrrolidin-1-ylmethyl)-7,8-dihydropteridin-6(5H)-one (7l)

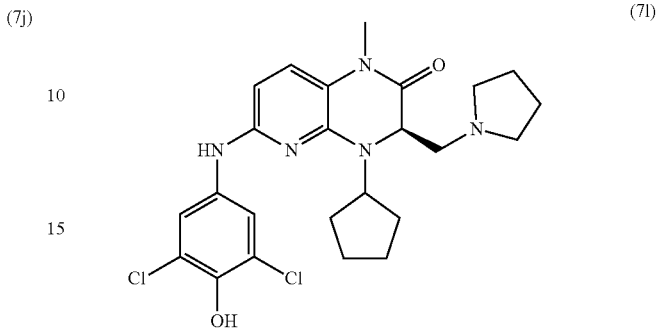

(7l)

$K_i(PI5P4K\alpha)$=160-320 nM
$K_i(PI5P4K\beta)$=500-1000 nM

Cell Culture, siRNA Knockdown and Mutant Expression

BT-474 and MCF7 breast cancer cells, C2Cl2 mouse myoblast cells, and HEK 293T cells were maintained in high-glucose DMEM medium containing 10% FBS. L6 rat myoblast cells were maintained in α-MEM medium containing 10% FBS. For differentiation into myotubes, C2Cl2 cells were kept in DMEM medium containing 2% horse serum for 5 days, and L6 cells were kept in α-MEM medium containing 2% FBS for 7 days. Amino-acid-free DMEM medium was prepared using powder from USBio, and MEM amino acids solution was from Gibco. Media were all supplemented with 100 U/ml penicillin/streptomycin. Cell lines were purchased from ATCC.

Before siRNA knockdown, C2Cl2 cells fully differentiated into myotubes. BT-474 cells were digested and diluted to give 30%-50% confluence 24 hrs after plating. Transfection of siRNA was achieved using Lipofectamine RNAiMAX reagent (Invitrogen) following manufacturer's protocol. For C2Cl2 myotubes, a final siRNA concentration of 100 nM was used in forward transfection. For BT-474 cells, a final siRNA concentration of 50 nM was used in reverse transfection. The siRNAs used are summarized below:

| Name | Source | siRNA ID or sequence | Target |
| --- | --- | --- | --- |
| Mouse PI5P4K2A oligo 1 | Sigma Aldrich | SASI_Mm01_00044773 | NM_008845 |
| Mouse PI5P4K2A oligo 2 | Sigma Aldrich | SASI_Mm01_00044774 | NM_008845 |
| Mouse PI5P4K2B oligo 1 | Thermo Scientific | GCAAGAUCAAGGUGGACAATT | NM_054051 |
| Mouse PI5P4K2B oligo 2 | Thermo Scientific | GCAUUUCGUGUGCCAGAAATT | NM_054051 |
| Human PI5P4K2A oligo 1 | Sigma Aldrich | SASI_Hs01_00192410 | NM_005028 |
| Human PI5P4K2A oligo 2 | Sigma Aldrich | SASI_Hs01_00192409 | NM_005028 |
| Human PI5P4K2B oligo 1 | Sigma Aldrich | SASI_Hs01_00186318 | NM_003559 |
| Human PI5P4K2B oligo 2 | Sigma Aldrich | SASI_Hs01_00186315 | NM_003559 |
| Negative Control (oligo "3") | Sigma Aldrich | SIC001 | |

Lentivirus was used to generate BT474 cell lines that stably expressed wildtype and mutant PI5P4Kβ. HEK 293T cells were used for lentiviral amplification. PI5P4Kβ wildtype and V148F/T201M double mutant were cloned into pLVX-IRES-Puro lentiviral vector (Clontech) along with a Kozak sequence and a 3×-Flag-tag at the N terminus using the in-fusion cloning reagents (Clontech). The expression plasmid, along with pMLV-Gag-Pol and pVSV-G plasmids, were transfected into HEK 293T cells. Viruses were collected 48 hrs after transfection and filtered. BT-474 cells were infected in the presence of 8 μg/ml polybrene (EMD Millipore), and stable lines were selected in basal media supplemented with 1 μg/ml puromycin (Gebico). Protein expression was confirmed by western blot with anti-Flag antibody (Cell Signaling Technology).

Immunoblot Analysis

After wash with cold DPBS buffer, cells were lysed in RIPA buffer that contained 50 mM Tris-HCl pH 8.0, 150 mM NaCl, 1 mM EDTA, 1 mM EGTA, 1% NP-40, 0.5% sodium deoxycholate, 0.1% SDS, and protease and phosphatase inhibitor cocktails (Roche). Total protein concentrations were measured using a BCA assay (Thermo scientific). Cell lysate (about 80 μg protein) was resolved by SDS-PAGE and blotted onto PVDF membranes. The membranes were probed overnight at 4° C. with appropriate primary antibodies (Cell Signaling Technology) and incubated with secondary fluorescent antibodies (LI-COR Biosciences) for 1 hr at room temperature before imaging by an Odyssey CLx system.

Adenine Nucleotides Measurement

BT-474 cells were plated on white solid-bottom 96-well plates in sextuplicate (corning 3917; $2 \times 10^4$ cells per well). C2Cl2 cells were plated and differentiated on the same type of plates. After treatment with compound overnight, total cellular ATP levels were measured by a luminescent ATP detection assay kit (Abcam) following manufacturer's protocol and normalized against the total protein concentration.

Figure 14A:
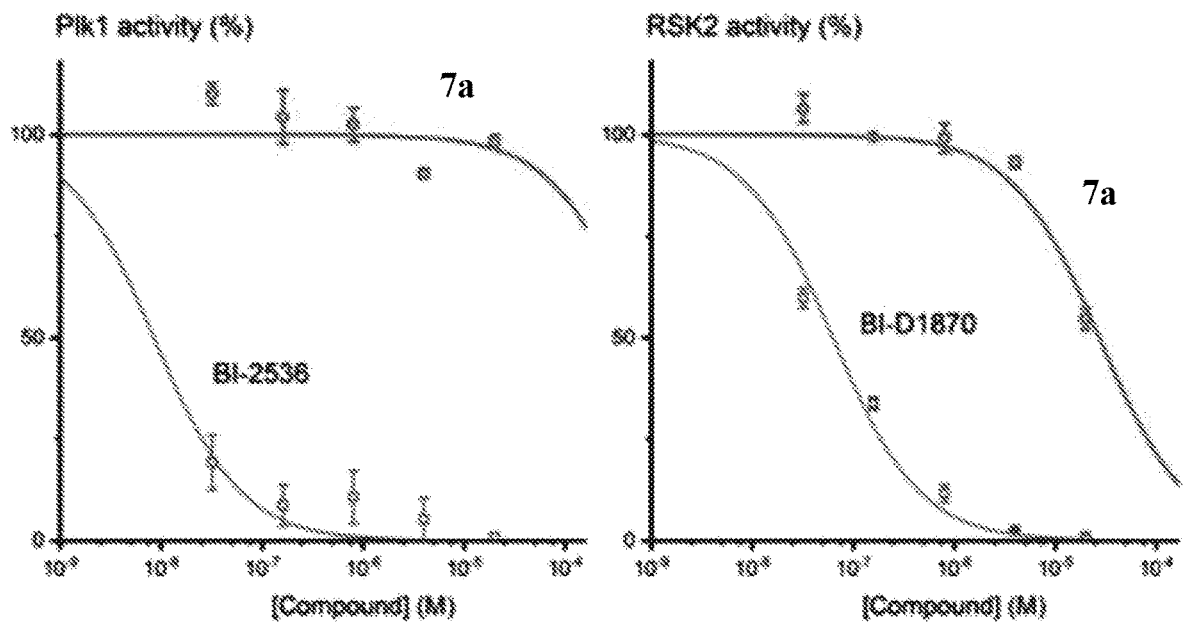

To measure nucleotide concentration using HPLC or LC-MS/MS, cells were rinsed three times with DPBS buffer at room temperature and lysed in ice-cold 0.4M perchloric acid (500 μl acid per $10^6$ cells). The culture dishes were sealed and transferred to a −80° C. freezer. Cell lysates were then thawed on ice, scraped off, and centrifuged at 14,000 rpm at 4° C. for 10 min. The pellet was solubilized in 0.2M NaOH and set aside for measurement of protein concentration. The supernatant was transferred to clean tubes and neutralized with 3M KHCO$_3$. The neutralized sample was kept on ice for 10 min and then transferred to a −80° C. freezer. After 2 hrs, thawed sample was centrifuged again to remove the precipitated perchlorate, filtered, adjusted according to protein concentration, aliquoted and stored at −80° C. The sample was thawed on ice just before the HPLC or LC-MS/MS experiment. (HPLC-Caroline). Sample (and AMP, ADP and ATP standards) was applied to an Agilent 1290 Infinity LC System equipped with a Hypercarb column (100 mm×4.6 mm, 5 mm; ThermoFisher Scientific) and coupled to an Agilent 6490 Triple Quad LC/MS. The nucleotides were separated using 20 mM ammonium acetate in water (solvent A) and 5% acetonitrile in water buffered with 20 mM ammonium acetate (solvent B), which were both adjusted with ammonium hydroxide to pH 9.0. The flow rate was 0.7 mL/min, and the column temperature was maintained at 35° C. The gradient elution program was: 0-2 min, 0-5% B; 2-12 min, 5-10% B; 12-22 min, 10-20% B; 22-25 min, 20-100% B; 25-30 min, 100% B, and then back to 100% A for 1 min, which was maintained for another 9 min to recondition the column. Mass spectrometric ESI ionization was performed in the negative ion mode and the source parameters were set as follows: gas temperature, 200° C.; gas flow, 12 L/min; nebulizer pressure, 35 psi; sheath gas temperature, 200° C.; sheath gas flow, 12 L/min; capillary voltage, −4,000V; fragmentor voltage, 380V. Quantification and confirmation of each compound was performed in the multiple reaction monitoring (MRM) mode (FIG. 14D).

Glucose Uptake, Glycolysis and ROS

To measure 2-deoxyglucose (2-DG) uptake, L6 myotubes were treated with compound or DMSO control overnight in the absence of serum in α-MEM. Following treatment, cells were washed twice with KRH buffer (50 mM HEPES pH 7.4, 137 mM NaCl, 4.7 mM KCl, 1.85 mM CaCl$_2$, 1.3 mM MgSO$_4$) containing 0.1% BSA. Residual wash buffer was removed by aspiration. Cells were then incubated for 10 min at 37° C. in a KRH buffer containing 0.1% BSA, 5 mM unlabeled 2-DG and 2 μCi/ml [1,2-$^3$H(N)]-2-deoxy-D-glucose (PerkinElmer). The uptake was terminated by washing four times with ice-cold KRH buffer containing 0.1% BSA. Nonspecific 2-DG uptake into cells was determined in the presence of 10 μM cytochalasin B, which inhibits glucose transporters, and subtracted. The cells were lysed with 0.05 M NaOH for 2 hrs at 37° C. 10 μl cell lysate was used to quantify protein concentration by BCA assay. The remaining sample was transferred to a scintillation vial containing 3 ml Opti-Fluor liquid scintillation cocktail (PerkinElmer), and radioactivity was determined using a Beckman Coulter LS 6500 scintillation system and normalized against protein concentration.

To measure glucose consumption and lactate production, a total of $1 \times 10^5$ cells were seeded into each well of a 12-well plate and cultured in the presence of compound for 48 hrs. The culture media were collected and deproteinized by centrifugation using an Amicon Ultra centrifugal filter (3 kDa cut-off), while cells were lysed and used for protein concentration determination by BCA assay. The media were assayed immediately for glucose and lactate levels using colorimetric assay kits from BioVision following the manufacturer's protocols. The values were normalized against protein concentration. All measurements were made in triplicate.

2',7'-dichlorofluorescin diacetate (DCFDA) was used to assess intracellular ROS levels. DCFDA is deacetylated in the cell and oxidized by ROS to a fluorescent product 2',7'-dichlorofluorescein (DCF). BT-474 cells were plated on a black clear-bottom 96-well plate (Corning 3603; $2 \times 10^4$ cells per well). ROS was measured by a DCFDA cellular ROS detection assay kit (Abcam) following the manufacturer's protocol. The cells were treated with compound for 6 hrs before fluorescence was measured using a SpectraMax M5 plate reader (excitation 485 nm, emission 535 nm).

Proliferation and Cell Cycle Analysis

To measure cell number using the CellTiter-Glo 2.0 assay kit (Promega), cultured cells were equilibrated to room temperature for 30 min, and an equal volume of the CellTiter-Glo reagent was added and mixed for 2 min on an orbital shaker. The plates were incubated for another 10 min before luminescence was recorded using a SpectraMax M5 plate reader. To assess the effect of compound on growth, cells were plated onto white solid-bottom 96-well plates (coming 3917) at 2,000 cells per well in sextuplicate. After 24 hrs, compound (or DMSO control) was added to the wells, and cell number was determined after culturing for 0, 24, 48, and 72 hrs.

To monitor cell cycle progression, cells were harvested by trypsinization, washed with DPBS, and fixed with cold 70% ethanol for 30 min at 4° C. Before analysis, $2 \times 10^6$ cells were washed with DPBS three times and treated with 100 μl 100 μg/ml ribonuclease (DNase-free; Sigma Aldrich) for 10 min at room temperature. Samples were then stained for total DNA using 400 μl DPBS containing 50 μg/ml propidium iodide (Invitrogen). Cell cycle distribution was analyzed by a BD LSR II flow cytometer.

Example 1: Discovery of the
2-Amino-Dihydropteridinone Pharmacophore

Figure 1B:
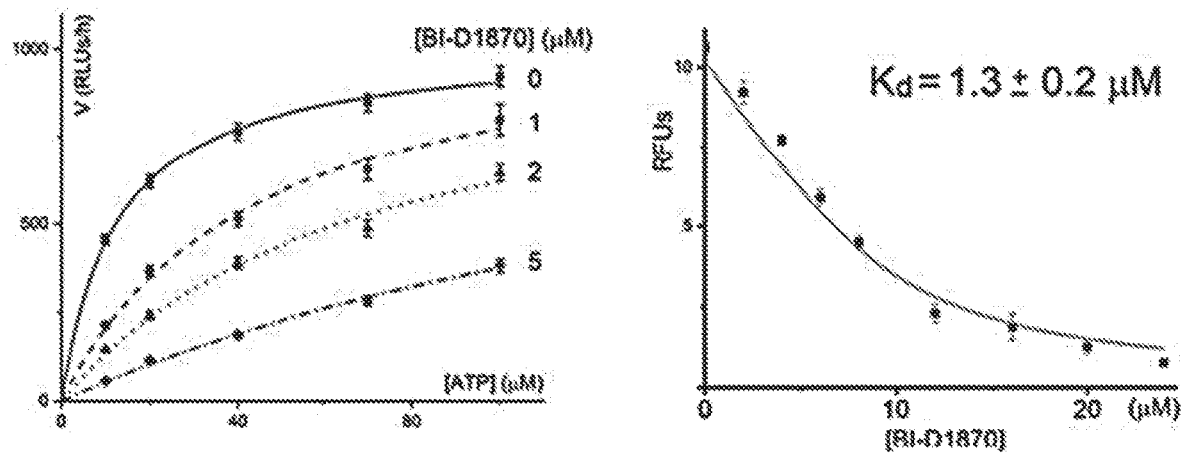
Figure 1C:
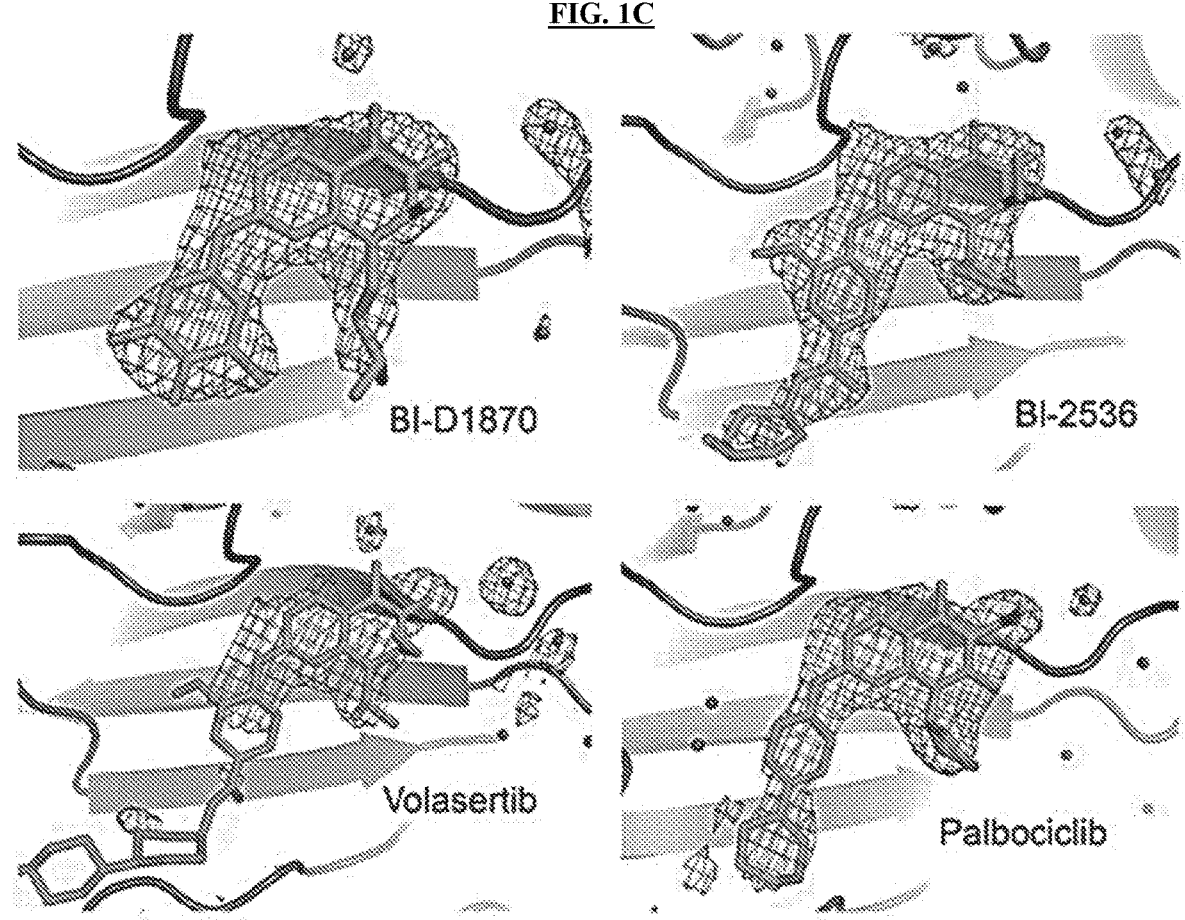
Figure 6A:
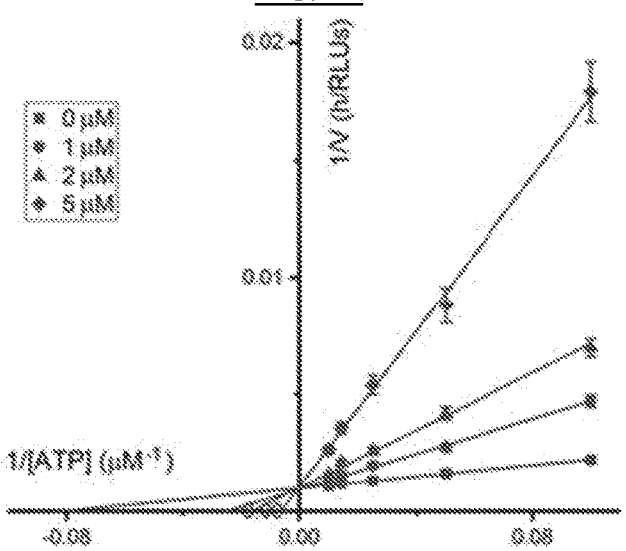
FIGS. 6A-6B are graphs showing that 2-amino-dihydropteridinone compounds (and a similar compound, palbociclib) are competitive with ATP binding to PI5P4Kα.
Figure 6B:
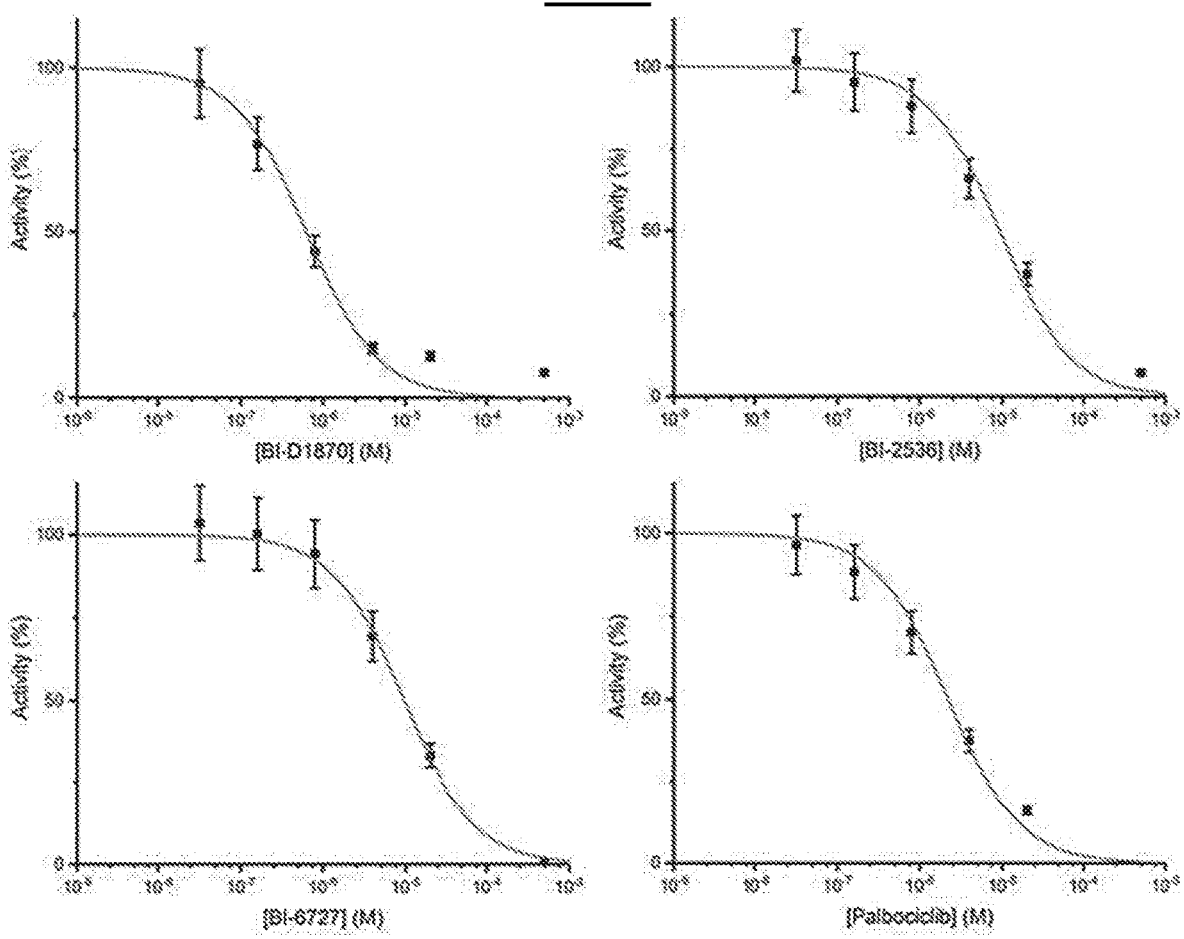
Figure 7A:
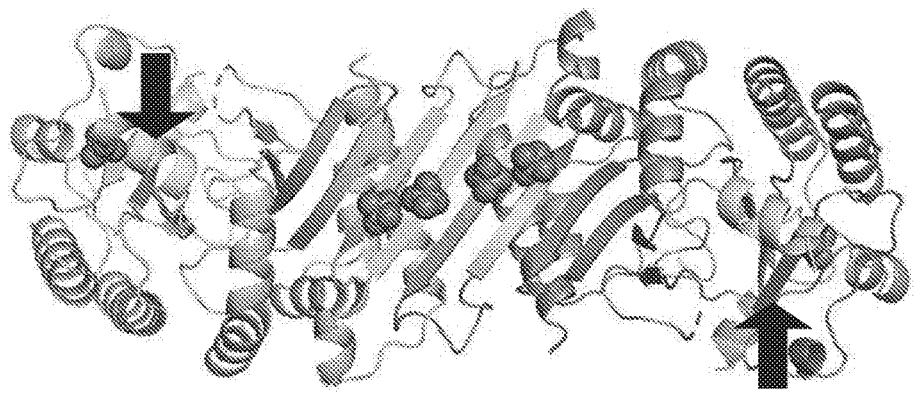
FIGS. 7A-7E are crystallographic analyses that illustrate the structure of the specificity loop of PI5P4Kα. PI5P4Kα crystals were obtained from two conditions. In both forms, extensive electron density in the shape of an α-helix was observed that corresponds to the N-terminal portion of the specificity loop.
Figure 7B:
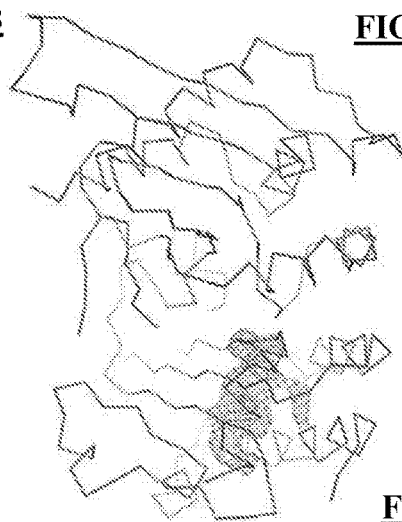
Figure 7D:
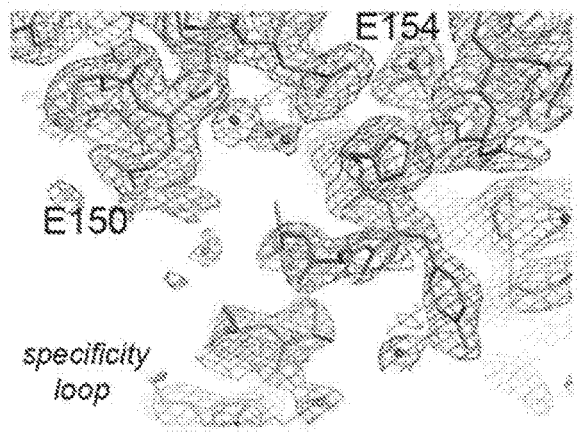
Figure 7C:
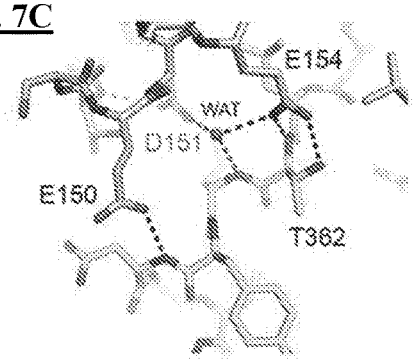
Figure 7E:
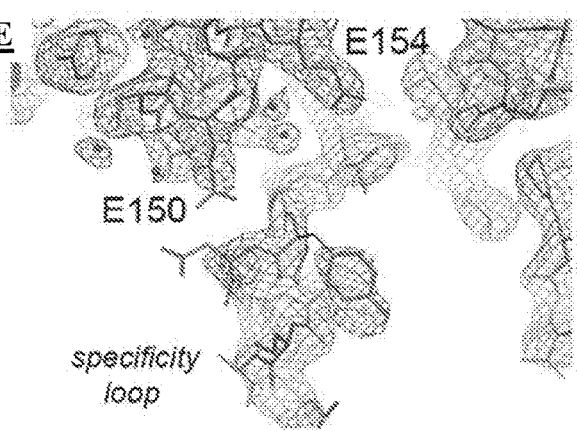

High-throughput screening of 5,758 small molecules, which included 725 FDA-approved drugs, 435 synthetic kinase inhibitors, 450 compounds from the NIH clinical collection and 4,148 other bioactive compounds, was conducted at the Yale Center for Molecular Discovery to identify novel leads against PI5P4Kα. The assay protocol is similar to that reported in Davis et al. PloS one, 2013, 8, e54127, but differs in lipid substrate preparation. Instead of dissolving the lipid in DMSO and mixing it with assay buffer by sonication, a dried 1:2 mixture of PI(5)P and phosphatidylserine was suspended in the buffer, sonicated and passed through a 0.2 μm extruder, which yielded unilamellar liposomes. Substrate prepared this way produced consistent results in a 384-well high-throughput assay format (Z'~0.8). The top-ranking compound from the screen was a dihydropteridinone derivative called BI-D1870, which is an inhibitor for protein kinase RSK (FIG. 1A). Kinetic studies showed that BI-D1870 was competitive with ATP and had a $K_i$ of ~1 μM, which was confirmed by directly measuring its binding affinity for PI5P4Kα (FIG. 1B; FIG. 6A). Crystallographic analysis showed that BI-D1870 was bound within the ATP binding pocket of the lipid kinase (FIG. 1C). The screen also produced three other compounds with identical or similar core structures: BI-2536, volasertib, and palbociclib, which are all protein kinase inhibitors but have slightly higher $K_i$s for PI5P4Kα (FIG. 1A; FIG. 6B).

Figure 1D:
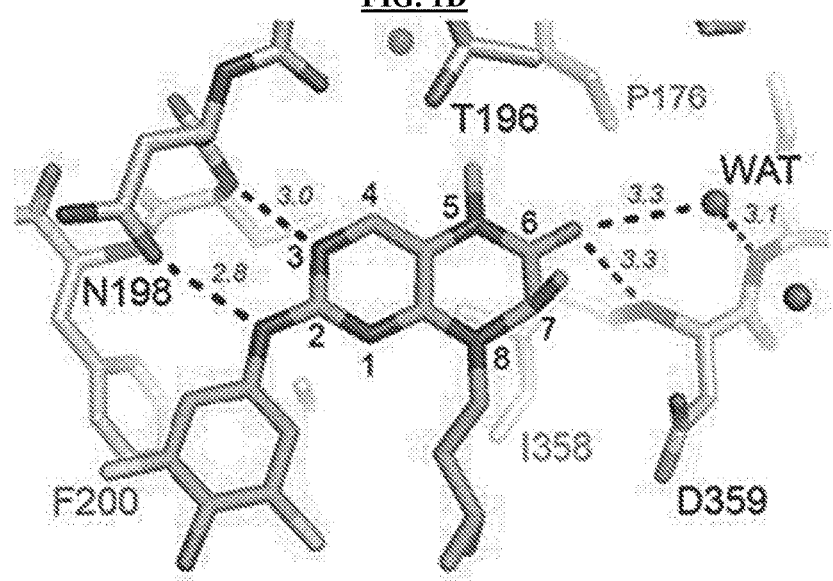

Crystal structures of PI5P4Kα in complex with AMP-PNP and with the lead compounds were solved to assist in the design of potent and PI5P4K-specific inhibitors (Tables 1 and 2). The structures also shed new light on enzyme mechanism, especially regarding the "specificity loop" (FIGS. 7A-7E), and ATP binding (FIGS. 8A-8D). The crystallographic analysis showed that all four compounds shared the same binding mode; the compounds bind to their respective protein kinase targets differently, with the core adopting opposing orientations (FIGS. 1C-1D). The common 2-amino dihydropteridinone moiety is bound within the adenine binding pocket of PI5P4Kα: the 2-amino group forms a hydrogen bond with Asn-198 (a hydrogen bond between Asn-198 and Lys-140 helps orient the oxygen toward the 2-amino group); the N3 of pteridine is hydrogen bonded to the backbone amide of Val-199; the 6-carbonyl replaces a water that is hydrogen bonded to the backbone amide of Asp-359 ("WAT1" in FIG. 9A). The 6-acetyl group of palbociclib is similarly posed to form hydrogen bonds with Asp-359 and Ile-360 (the latter mediated through a water molecule). The other aromatic ring linked to the 2-amino group, e.g., the difluorophenol group in BI-D1870, is snugly fit inside a hydrophobic cleft formed between Phe-134 and Phe-200. Phe-134 is flexible and adopts a different conformation in the complex with AMP-PNP.

TABLE 1

Crystallographic statistics for apo and AMP-PNP bound PI5P4Kα (space group: $P6_122$).

| Data Collection | Apo | $^d$Apo (2) | AMP-PNP | $^d$AMP-PNP (2) |
|---|---|---|---|---|
| Wavelength (Å) | 1.075 | 1.075 | 1.075 | 1.075 |
| Unit cell (a, c; Å) | 135.7, 95.1 | 135.7, 94.3 | 136.1, 95.1 | 135.9, 94.9 |
| $^a$Resolution (Å) | 40-2.2 | 40-2.5 | 40-2.1 | 40-2.0 |
|  | (2.28-2.20) | (2.59-2.50) | (2.18-2.10) | (2.07-2.00) |
| Redundancy | 14.2 | 18.6 | 13.6 | 37.1 |
| Completeness (%) | 97.8 | 100.0 | 99.7 | 97.7 |
| <I/σ> | 10.8 | 18.4 | 11.0 | 10.3 |
| $^{a,b}R_{merge}$ | 0.093 (0.870) | 0.087 (0.766) | 0.074 (0.711) | 0.091 (0.726) |
| Refinement | | | | |
| Unique reflections | 24,766 | 17,349 | 29,179 | 32,904 |
| Number of atoms | | | | |
| Protein | 2,440 | 2,466 | 2,468 | 2,429 |
| Ligand | — | — | 33 | 33 |
| Solvent | 168 | 135 | 197 | 205 |
| $^cR_{work}/R_{free}$ | 0.208/0.245 | 0.197/0.233 | 0.213/0.251 | 0.213/0.251 |
| B-factor (Å$^2$) | 54 | 64 | 49 | 52 |
| r.m.s. deviations | | | | |
| Bond lengths (Å) | 0.010 | 0.007 | 0.009 | 0.008 |
| Bond angles (°) | 1.225 | 1.065 | 1.196 | 1.165 |
| PDB accession code | 6DV7 | 6DV8 | 6DVF | 6DVG |

$^a$Highest resolution shell is shown in parentheses.

$^bR_{merge} = \Sigma \mid I_i - <I> \mid / \Sigma I_i$ $^cR_{work} = \Sigma \mid F_o - F_c \mid / \Sigma F_o$. $R_{free}$ is the cross-validation R factor for the test set of reflections (5% of the total) omitted in model refinement.

$^d$This crystal form, although in the same space group, was obtained from a different crystallization condition.

TABLE 2

Crystallographic statistics for PI5P4Kα inhibitor complexes (space group: P6₁22).

| Data Collection | BI-D1870 | BI-2536 | Volasertib | Palbociclib |
|---|---|---|---|---|
| Wavelength (Å) | 1.181 | 0.979 | 0.979 | 0.979 |
| Unit cell (a, c; Å) | 136.3, 95.4 | 136.4, 95.0 | 136.1, 95.2 | 135.9, 95.0 |
| $^a$Resolution (Å) | 40-2.7 | 40-2.6 | 40-2.3 | 40-2.7 |
|  | (2.80-2.70) | (2.69-2.60) | (2.38-2.30) | (2.80-2.70) |
| Redundancy | 14.2 | 9.6 | 14.2 | 14.4 |
| Completeness (%) | 100.0 | 97.5 | 100.0 | 100.0 |
| <I/σ> | 10.3 | 12.0 | 13.6 | 10.5 |
| $^{a,b}R_{merge}$ | 0.149 (0.713) | 0.082 (0.827) | 0.077 (0.577) | 0.074 (0.842) |
| Refinement |  |  |  |  |
| Unique reflections | 14,142 | 15,422 | 22,411 | 14,011 |
| Number of atoms |  |  |  |  |
| Protein | 2,366 | 2,367 | 2,379 | 2,377 |
| Ligand | 28 | 38 | 45 | 33 |
| Solvent | 115 | 81 | 135 | 81 |
| $^cR_{work}/R_{free}$ | 0.193/0.242 | 0.195/0.236 | 0.214/0.258 | 0.197/0.253 |
| B-factor (Å$^2$) | 61 | 70 | 61 | 72 |
| r.m.s. deviations |  |  |  |  |
| Bond lengths (Å) | 0.008 | 0.008 | 0.007 | 0.008 |
| Bond angles (°) | 1.256 | 1.228 | 1.088 | 1.243 |
| PDB accession code | 6DTY | 6DVJ | 6DW8 | 6DWL |

$^a$Highest resolution shell is shown in parentheses.
$^bR_{merge} = \Sigma \mid I_i - <I> \mid / \Sigma I_i$
$^cR_{work} = \Sigma \mid F_o - F_c \mid / \Sigma F_o$. $R_{free}$ is the cross-validation R factor for the test set of reflections (5% of the total) omitted in model refinement.

Example 2: Synthesis of Potent and Selective PI5P4K Inhibitors

The binding mode of the compounds discovered in the screen resembled that of BI-2536 bound to Plk1 (FIG. 10A). Like other type I inhibitors, BI-2536 recognizes the active, DFG-in, conformation of the kinase: the DFG-in conformation enables the backbone amides of Asp-194 and Phe-195 to engage the 6-carbonyl of dihydropteridinone through water-mediated hydrogen bonds. Since dihydropteridinone is not compatible with the inactive DFG-out conformation of protein kinase, due to steric constraints imposed by its 6-carbonyl, a major consideration in engineering novel protein kinase inhibitors to selectively target PI5P4K was to incorporate structural features that would have a conflict with the active conformation of protein kinase in general.

Figure 2A:
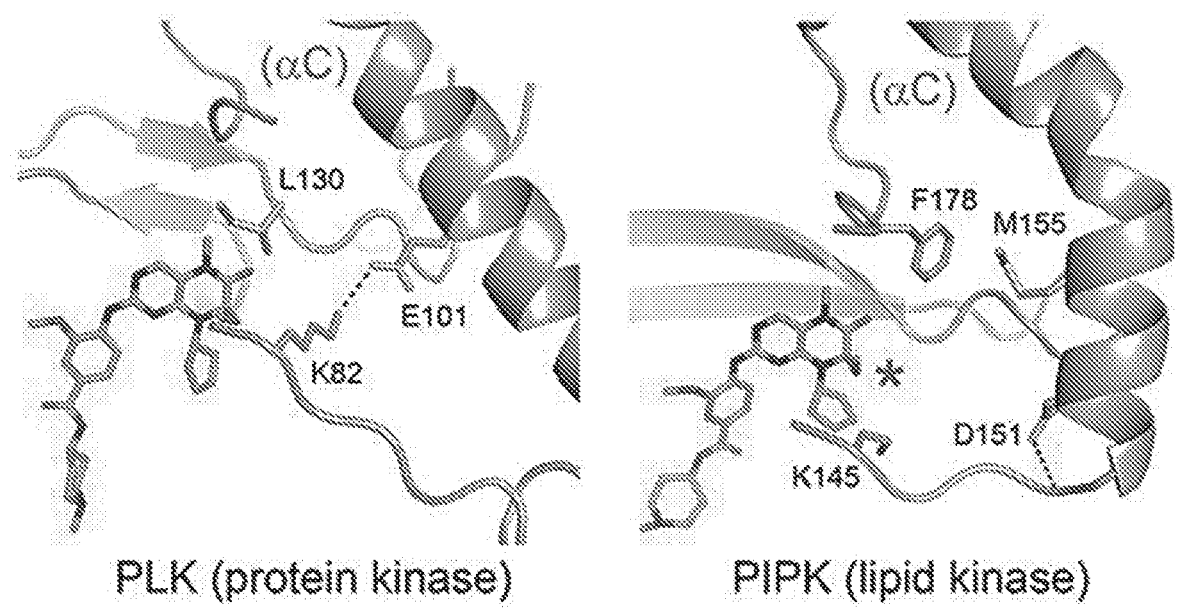
FIGS. 2A-2D are graphs and diagrams showing the potency and selectivity of the novel lipid kinase inhibitors of the invention.
Figure 8A:
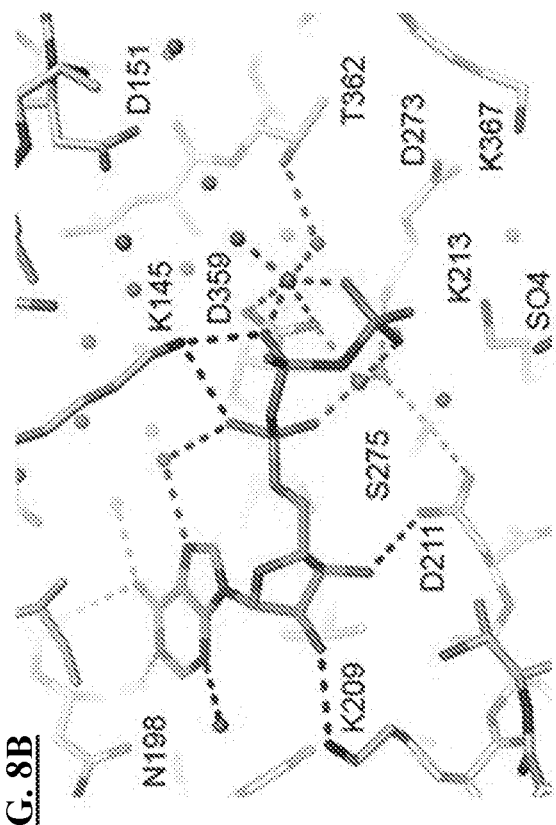
FIGS. 8A-8D are diagrams showing the binding mode of ATP with PI5P4Kα.
Figure 8B:
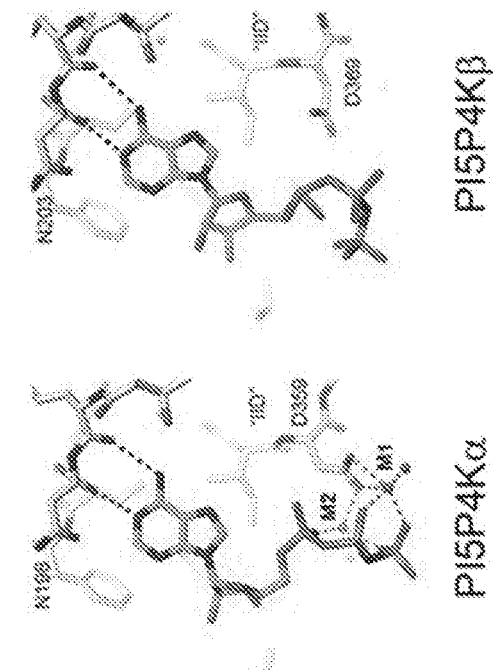
Figure 8C:
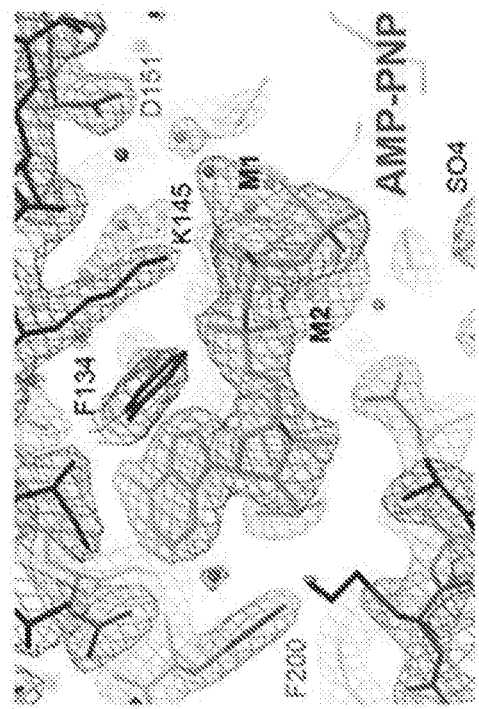
Figure 8D:
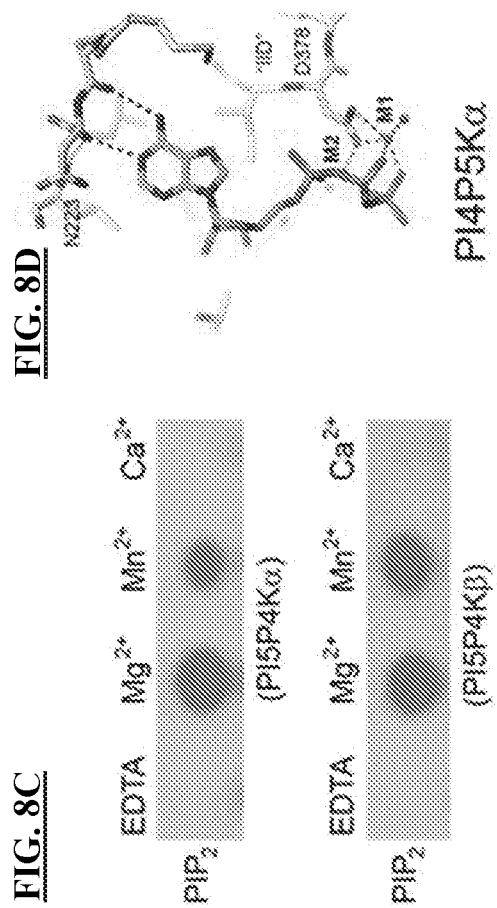
Figure 9A:
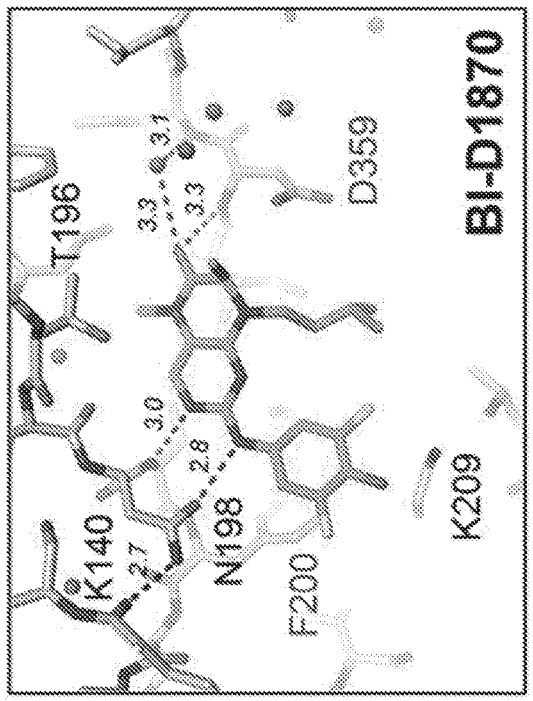
FIGS. 9A-9D are diagrams detailing the binding interactions between the lead compounds and PI5P4Kα. Hydrogen bonds are shown as dashed lines with bond lengths indicated. Waters are shown as red spheres. In the apo structure, the backbone amide groups of Asp-359 and Ile-360 attract two water molecules, WAT1 and WAT2, which are hydrogen bonded to a chain of other well-ordered water molecules within the active site. WAT1 is displaced by a carbonyl oxygen of the bound compounds. In the complex with palbociclib, Asp-125 from the Gly-rich loop undergoes a conformational change to engage the piperazine side chain of the compound.
Figure 9B:
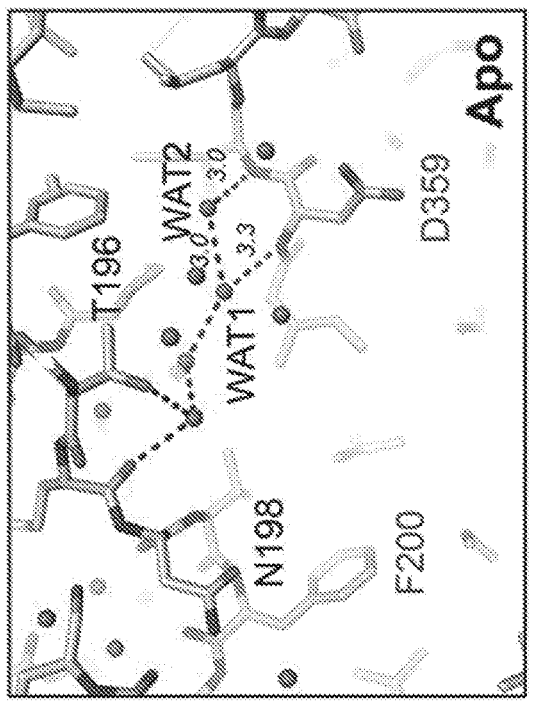
Figure 9C:
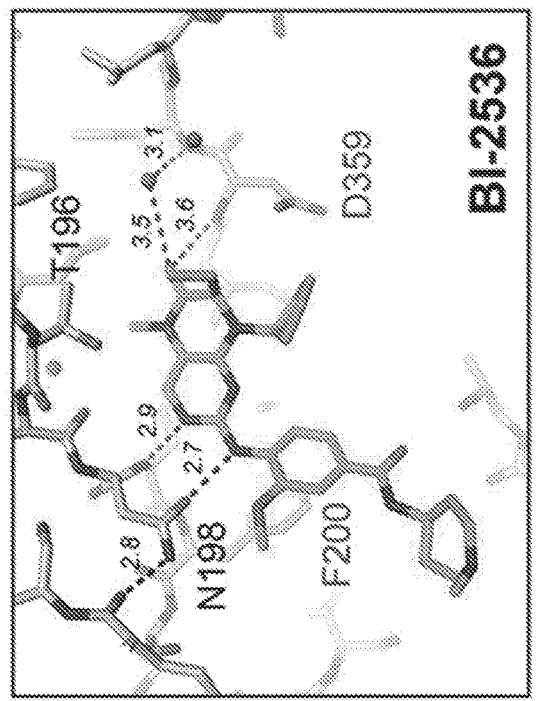
Figure 9D:
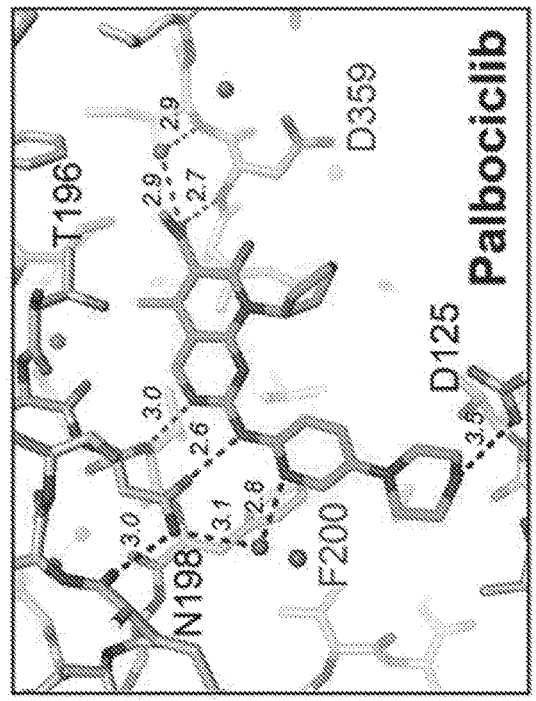

In Plk1, as in all active protein kinases, there is a conserved salt bridge between Lys-82 (from a central β-strand in the N-lobe) and Glu-101 (from αC), which stabilizes the lysine for ATP binding. In PI5P4Kα, the salt bridge is missing. The helix that corresponds to αC is bent near where the glutamate is in Plk1, whereas the glutamate is replaced by a hydrophobic residue (Met-155). The kink is a defining feature of the lipid kinase family, contributing to the formation of a flat protein surface for membrane binding. Although Asp-151, on the preceding turn of the helix, is highly conserved, it does not interact with the lysine and is instead hydrogen bonded to Thr-148 (FIGS. 8A-8B). In Plk1, the salt bridge is immediately adjacent to the C7 ethyl side chain of BI-2536, whereas in PI5P4Kα, the kinked helix, as well as the missing salt bridge, create a deep hydrophobic pocket that is accessible from C7 of the pteridine ring (asterisk in FIG. 2A; FIGS. 10B-10C). Therefore, in the novel compounds synthesized, a bulky hydrophobic group was introduced at the C7 position of the 2-amino-dihydropteridinone pharmacophore, which would enhance the complementary fit with PI5P4K, while preventing the compounds from binding to any active protein kinase.

Figure 2B:
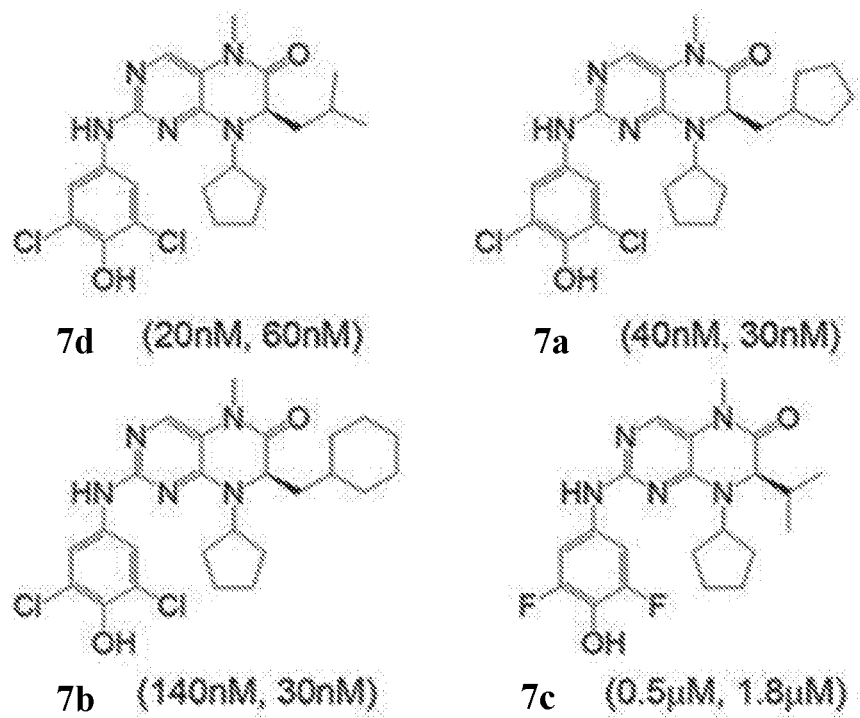
Figure 2C:
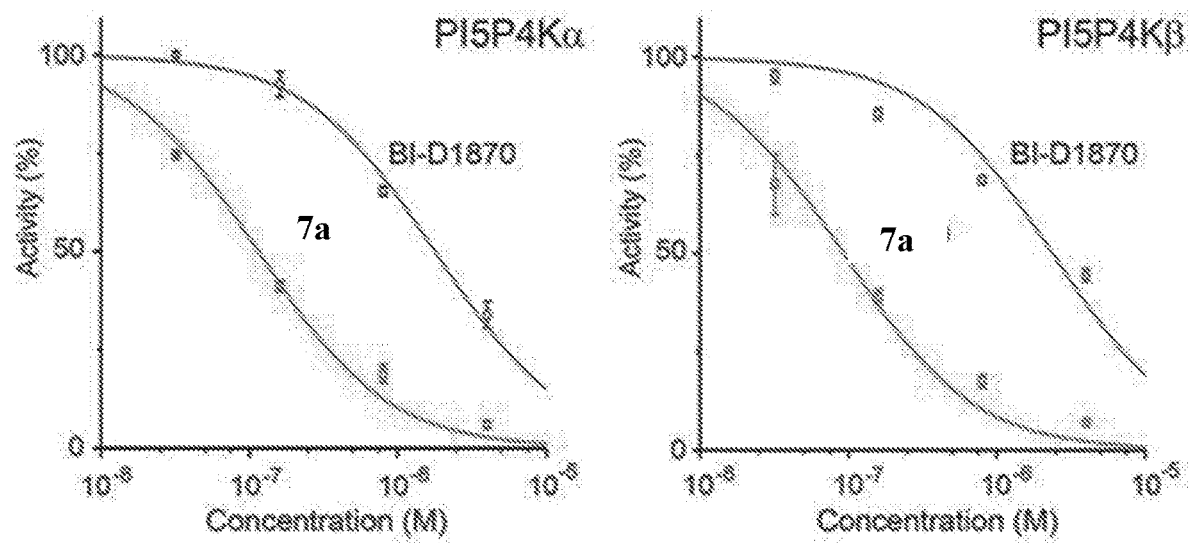

A large synthetic effort was made to attach various hydrophobic side chains to C7, and to swap side chains at the 2-amino group, and at N8, of the screened compounds. Combining the difluorophenol side chain of BI-D1870 with the 8-CH$_2$cyclopentyl side chain of BI-2536 was found early on to enhance binding, and this feature was maintained. From a pool of 19 newly synthesized compounds, some demonstrated exceptional potency toward both PI5P4Kα and PI5P4Kβ (FIGS. 2B-2C; FIGS. 12A-12D). 7d, with an isobutyl C$_7$ side chain, was the most potent against PI5P4Kα (K$_i$~20 nM, representing a 50-fold gain over parent compound BI-D1870). Replacing the isobutyl with a cyclopentyl in 7a improved potency toward PI5P4Kβ (K$_i$~30 nM). Increasing the size of the side chain further in 7b started to weaken the affinity with PI5P4Kα, but had no effect on PI5P4Kβ binding, making this compound a prototype for differentiating the two isoforms. The isopropyl side chain in 7c severely reduced the gain in potency over the initially screened compounds. Given its structural similarity to the more active compounds (7a, 7b and 7d), 7c was useful as a control compound in cell-based experiments.

Figure 2D:
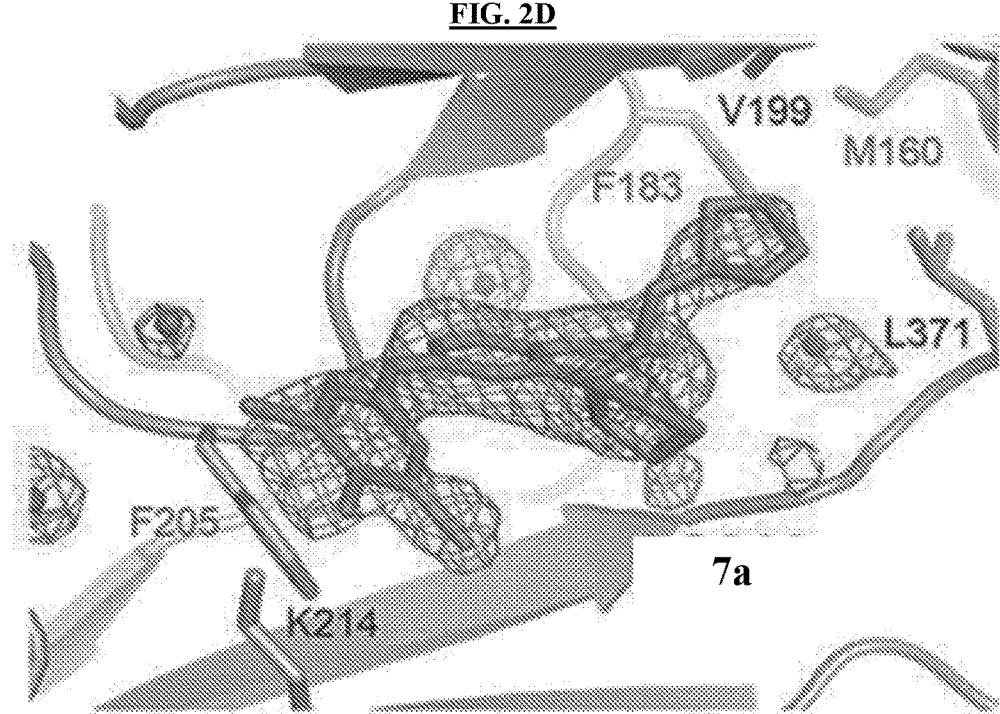

7a was co-crystallized with PI5P4Kβ (Table 3). Difference Fourier map confirmed that the compound was bound at the ATP-binding site, projecting its 7-CH$_2$cyclopentyl side chain into the lipid-kinase-specific pocket (FIG. 2D). Inhibitor binding caused little conformational change in PI5P4Kβ except for the Gly-rich loop, which caps the ATP-binding site, and has been found to adopt a number of conformations in the apo form (FIGS. 13A-13D).

TABLE 3

Crystallographic statistics for PI5P4Kβ (space group: P2₁).

| Data Collection | Apo | CC260 |
|---|---|---|
| Wavelength (Å) | 0.979 | 0.979 |
| Cell Dimensions (Å) | a = 71.7, b = 51.2, c = 107.1<br>β = 94.6° | a = 73.5, b = 51.7, c = 107.6<br>β = 95.4° |
| $^a$Resolution (Å) | 40-2.5 (2.59-2.50) | 40-2.7 (2.80-2.70) |
| Redundancy | 2.6 | 3.9 |
| Completeness (%) | 89.0 | 98.8 |
| <I/σ> | 4.6 | 7.0 |
| $^{a,b}R_{merge}$ | 0.129 (0.660) | 0.122 (0.968) |
| Refinement | | |
| Unique reflections | 23,433 | 21,128 |
| Number of Atoms | | |
| Protein | 4,588 | 4,708 |
| Ligand | — | 33 |
| Solvent | 115 | 138 |
| $^cR_{work}/R_{free}$ | 0.201/0.283 | 0.187/0.280 |
| B-factor (Å²) | 61 | 71 |
| r.m.s. deviations | | |
| Bond lengths (Å) | 0.012 | 0.012 |
| Bond angles (°) | 1.645 | 1.631 |
| PDB accession code | 6DWP | 6E0J |

$^a$Highest resolution shell is shown in parentheses.
$^bR_{merge} = \Sigma \mid I_i - <I> \mid / \Sigma I_i$
$^cR_{work} = \Sigma \mid F_o - F_c \mid / \Sigma F_o$. $R_{free}$ is the cross-validation R factor for the test set of reflections (5% of the total) omitted in model refinement.

Figure 14C:
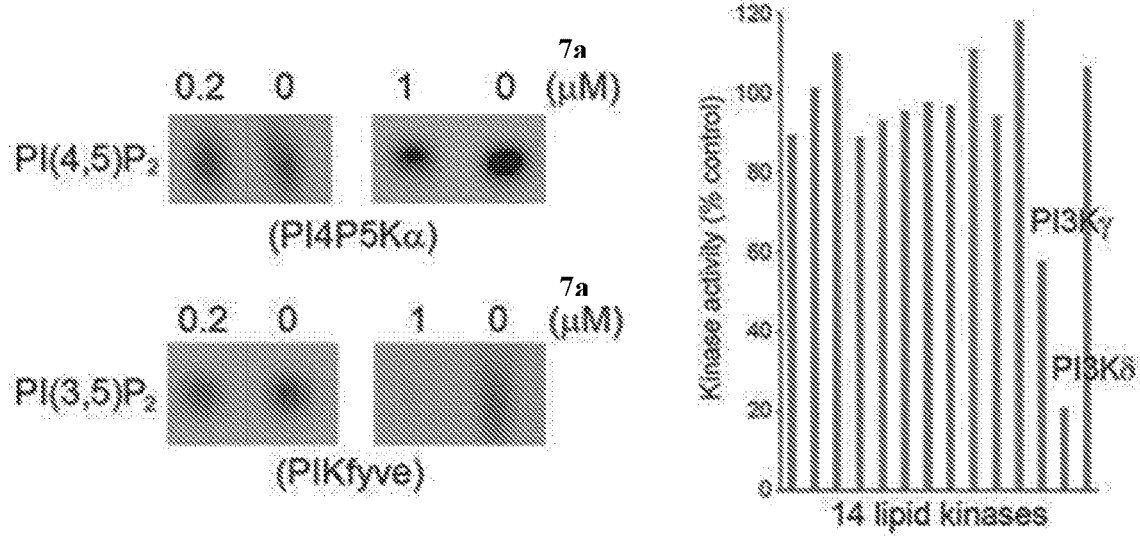
Figure 14B:
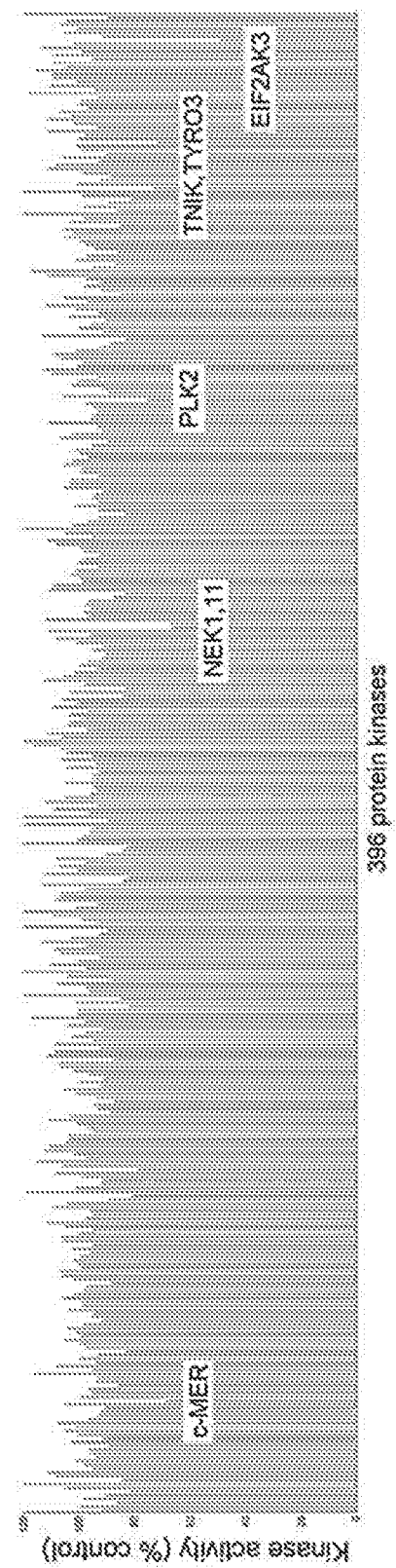
Figure 16A:
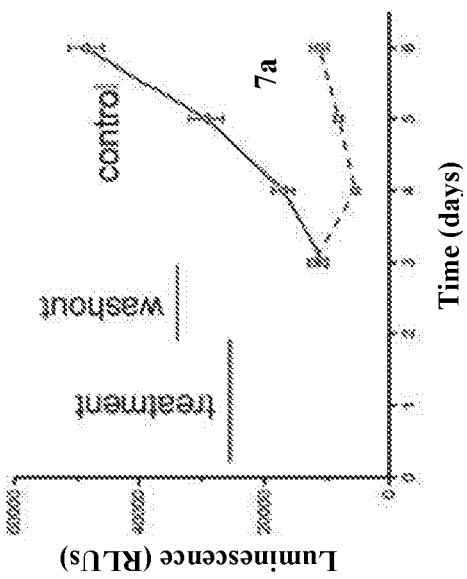
FIGS. 16A-16D are graphs and a scheme showing that PI5P4Kα/β inhibition disrupted cell metabolism.
Figure 16B:
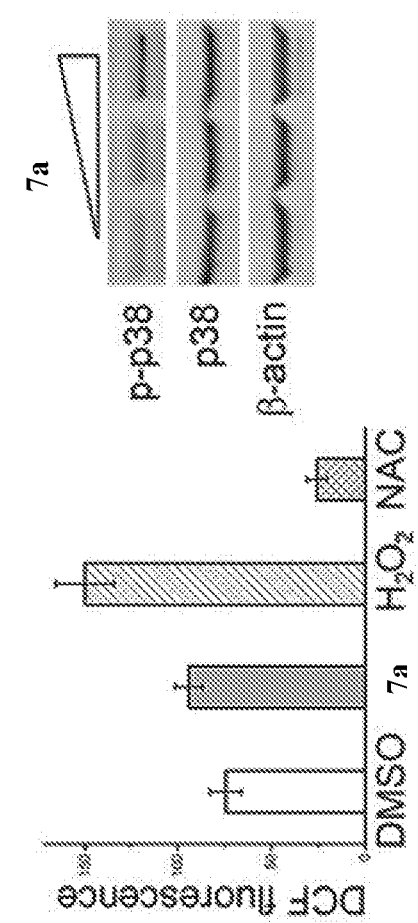
Figure 16C:
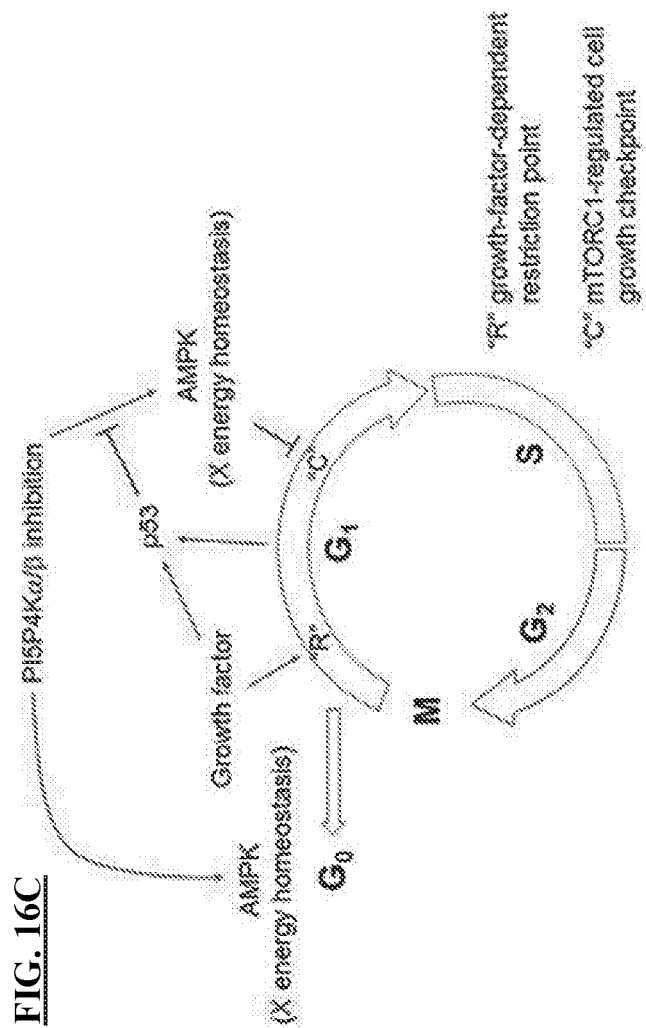
Figure 16D:
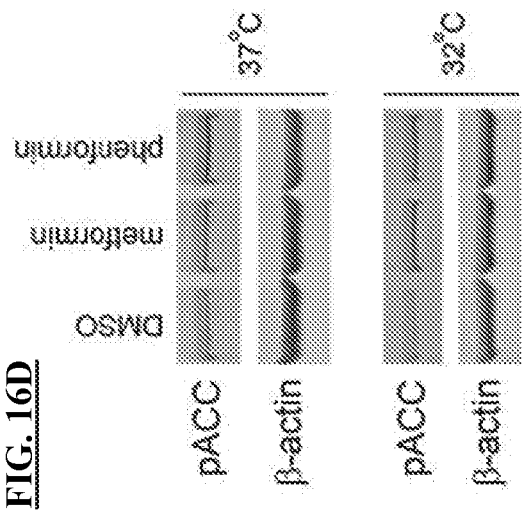
Figure 17A:
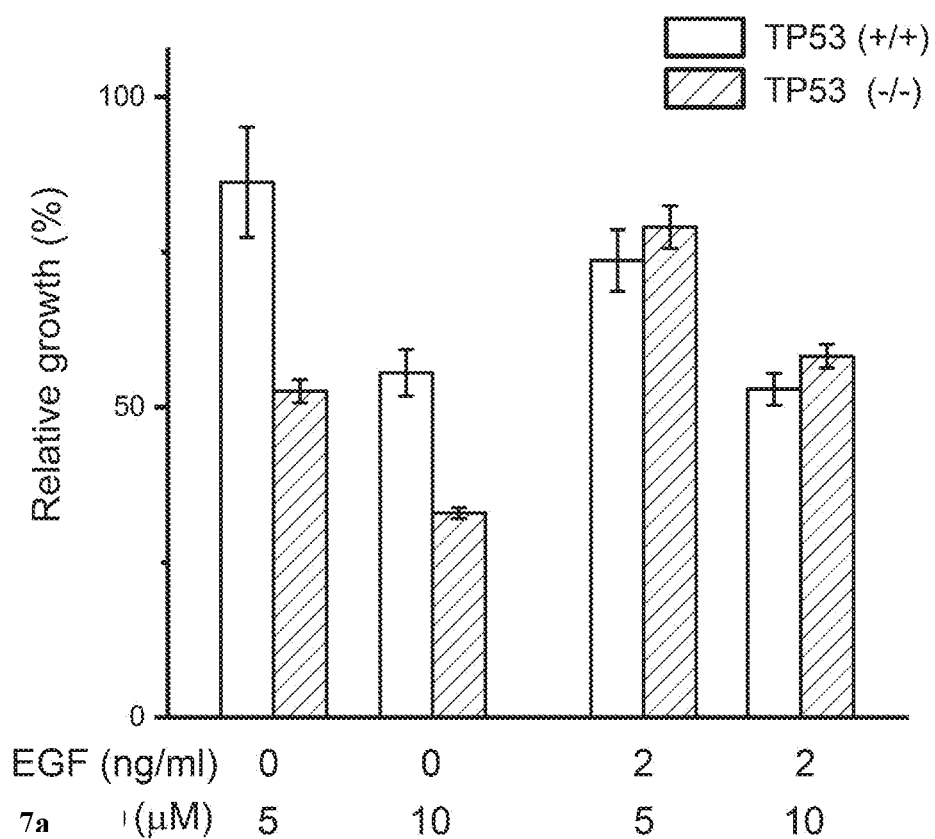
FIG. 17A: Dose response relationship of 7a on the growth rates of a pair of isogenic MCF10A cell lines that differ only in p53 status (MCF10A is a triple negative breast cancer cell line). Without EGF supplement, the growth of p53(−/−) cells is more sensitive to 7a. However, the difference is lost when EGF is added to the culture media.
Figure 17B:
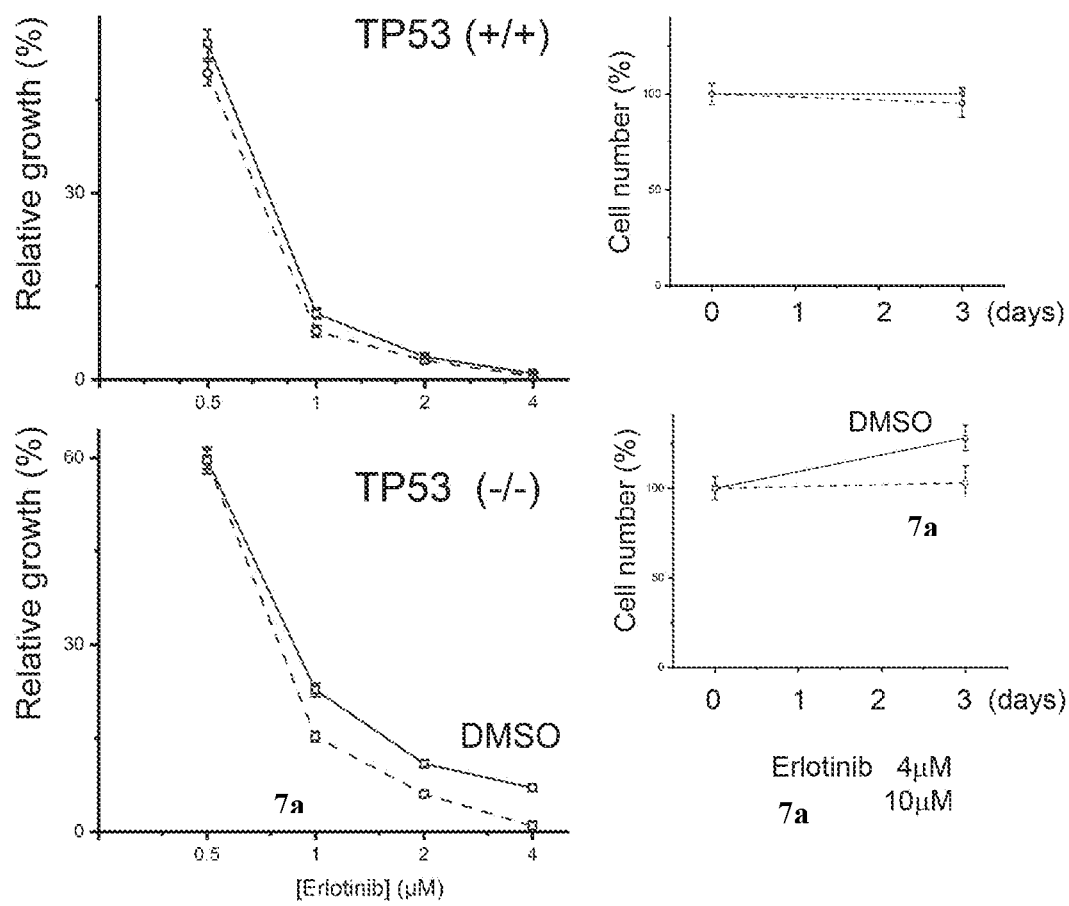
Figure 17C:
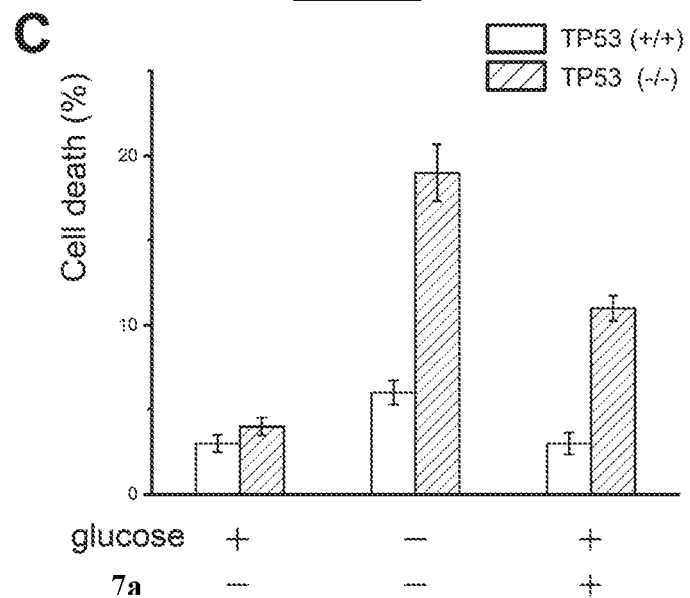
FIG. 17C: Cell death upon serum withdrawal is measured by trypan blue staining. p53(−/−) Cells are more susceptible to metabolic perturbations caused by glucose starvation. Similarly, 7a, by interfering with cells' energy metabolism, selectively kills p53(−/−) cells.

To test if the new compounds demonstrated selectivity against protein kinases, 7a was assayed against Plk1 and RSK2, the targets of parent compounds BI-2536 and BI-D1870 (FIGS. 14A-14D). 7a no longer inhibited Plk1, and only inhibited RSK2 weakly ($K_i$~1 μM, 50 times less potent than BI-D1870). 7a was also profiled against a panel of 396 protein kinases (including atypical kinases; FIG. 14B). At a compound concentration of 0.5 μM, only 7 protein kinases were mildly inhibited (EIF2AK3, 50% activity remaining; NEK11, 66%; NEK1, 67%; c-MER, 67%; TYRO3, 72%; TNIK, 73%; PLK2, 75%), and the $K_i$s of 7a for these kinases were estimated to range from 250-1,000 nM, substantially higher than the $K_i$ for PI5P4Kβ.

PI4P5K (type 1 PIPK), PI5P4K (type 2) and PIKfyve (type 3) have homologous kinase domains. 7a showed little activity against PI4P5Kα ($K_i$~5 μM), and modestly inhibited PIKfyve ($K_i$~200 nM; FIG. 14C). Further profiling against a panel of 14 lipid kinases showed that 7a did not inhibit most PI3Ks, PI4Ks or sphingosine kinases, but modestly inhibited PI3Kγ ($K_i$~200 nM), and quite potently inhibited PI3Kδ ($K_i$~120 nM).

Example 3: PI5P4Kβ Inhibition Causes AMPK Activation in Cultured Myotubes

It was previously observed that PIP4K2B$^{-/-}$ mice were hypersensitive to insulin, with significantly enhanced Akt activity, particularly in skeletal muscles, upon hormone stimulation (Lamia et al. Molecular and cellular biology 2004, 24, 5080-5087). Interpretation of the phenotype was complicated, however, by the fact that the gene knockout also affected development, producing slightly growth-retarded animals. Now equipped with a potent small-molecule inhibitor for PI5P4Kβ, the effect of acutely inhibiting the lipid kinase activity on cell signaling could be directly tested. In cultured C2Cl2 myotubes, overnight incubation with 20 μM 7a increased hormone-induced Akt phosphorylation, especially at Ser-473 (FIG. 3A).

This result is in general agreement with the observation made in PIP4K2B$^{-/-}$ mice, but contradicts with the finding that, in dPIP4K$^{-/-}$ flies (Drosophila has only one PI5P4K isoform), Akt phosphorylation at Ser-505, the counterpart of mammalian Ser-473, was reduced, at least during the larval stage (Gupta et al., PNAS, 2013, 110, 5963-5968). Without intending to be limited to any particular theory, it is possible that the effect of PI5P4K inhibition on Akt activation is context-dependent. A portion of the increase in Akt phosphorylation could be caused by PI5P4Kα inhibition, as 7a was found to be equally potent toward PI5P4Kα, because acute removal of PI5P4Kα in cell culture through auxin degron has been found to increase Ser-473 phosphorylation (Bulley et al. PNAS, 2016, 113, 10571-10576).

Upon 7a treatment, both basal and insulin-induced phosphorylation of S6K at Thr-389 was reduced, confirming that mTORC1 activity was suppressed in C2Cl2 myotubes (FIG. 3A). Akt is a major activator of mTORC1 (Laplante, et al., 2012, Cell 149:274-293). The seemingly conflicting observations that 7a enhanced Akt phosphorylation but suppressed mTORC1 prompted further investigation into whether other inputs to mTORC1 were altered by PI5P4Kβ inhibition (FIG. 3B). It was found that, although 7a reduced overall level of S6K phosphorylation, mTORC1 activity remained sensitive to the presence of amino acids in culture media (FIG. 3B). In both C2Cl2 and L6 myotubes, 7a significantly increased phosphorylation of acetyl-CoA carboxylase (ACC), another major substrate for AMPK, in a dose-dependent manner (FIG. 3B). The possibility that PI5P4Kβ inhibition caused AMPK activation was corroborated by siRNA knockdown of PI5P4Kβ expression in C2Cl2 myotubes (FIG. 3C). Knockdown of the more active isoform, PI5P4Kα, had no obvious effect on ACC phosphorylation. These results agree with genetic experiments showing that only PIP4K2B$^{-/-}$ mice, and not PIP4K2A$^{-/-}$ mice, are growth retarded and manifest hypersensitive to insulin, and suggest a causal link from AMPK activation to the observed developmental and metabolic phenotypes.

Based on these results, one plausible explanation for the enhanced insulin sensitivity in myocytes is the suppression of mTORC1 activity. In a negative feedback loop, mTORC1 and S6K phosphorylate insulin receptor substrate (IRS) on multiple serine residues, reducing its ability to activate PI3K (FIG. 3B). 7a treatment reduced IRS phosphorylation at Ser-302, a known S6K site (FIG. 3D). Rapamycin, which almost eliminates Ser-302 phosphorylation, only modestly increased Akt phosphorylation, whereas 7a had a more pronounced effect, suggesting that additional signaling components were invoked upon PI5P4Kβ inactivation (FIG. 3D).

The signaling circuitry illustrated in FIG. 3B involves two classes of lipid kinase PI3Ks. Class I PI3K, upon activation by IRS, converts $PI(4,5)P_2$ to $PI(3,4,5)P_3$, which recruits Akt to plasma membrane for phosphorylation. Class III PI3K, or Vps34, is required for mTORC1 activation by amino acids. In C2Cl2 myotubes, 7a did not interfere with their functions (FIG. 3E). This agrees with in vitro profiling results showing that p110α/p85α and Vps34 are not inhibited by the compound.

Parent compounds BI-D1870 and BI-2536 did not induce ACC phosphorylation in myotubes, suggesting that AMPK activation is a new biological activity associated with the chemical modifications introduced into 7a (FIG. 3F). 7c, a structurally similar compound that does not potently inhibit PI5P4Kα or PI5P4Kβ in vitro, also failed to induce ACC phosphorylation. 7b, more potent against PI5P4Kβ than PI5P4Kα, enhanced ACC phosphorylation to a similar degree as 7a, or 7d. Taken together, these experimental results indicate that PI5P4Kβ is the intracellular target of 7a responsible for the elevated AMPK activity.

Example 4: PI5P4Kβ Inhibition Disrupts Energy Homeostasis in Myotubes

Enhanced AMPK signaling suggests that cell energy status was perturbed upon PI5P4Kβ inhibition. Measurements of intracellular ATP levels, either using a bioluminescence assay (FIG. 4A), or by HPLC (FIGS. 15A-15B), consistently showed a 15% reduction in compound-treated myotubes. In contrast, ADP concentration remained unchanged. AMP, which has a much lower concentration and overlapped with other metabolites upon HPLC fractionation, was quantified by triple quadrupole LC-MS/MS, which identifies the metabolite not only by its molecular weight, but also by its known fragmentation pattern (FIG. 15C). The tandem mass spectrometry experiment revealed that 7a treatment caused a 30% increase in AMP concentration, or a 50% increase in AMP/ATP ratio (FIG. 4B). Without intending to be limited by any particular theory, the accumulation of intracellular AMP explains the observed increase in ACC phosphorylation by AMPK.

Figure 4C:
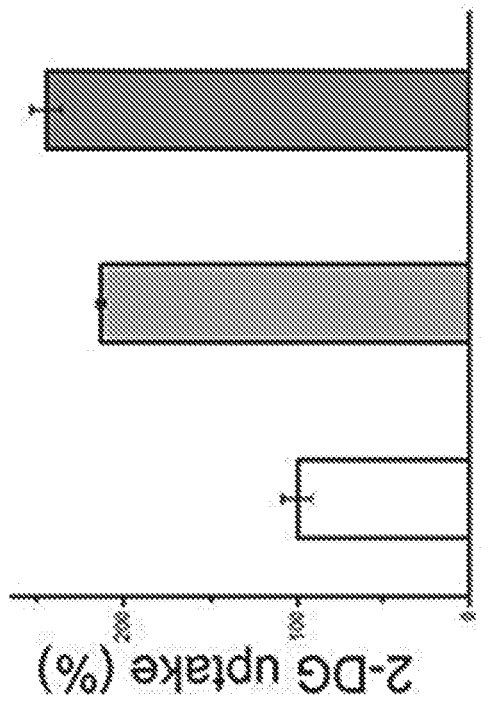
Figure 4D:
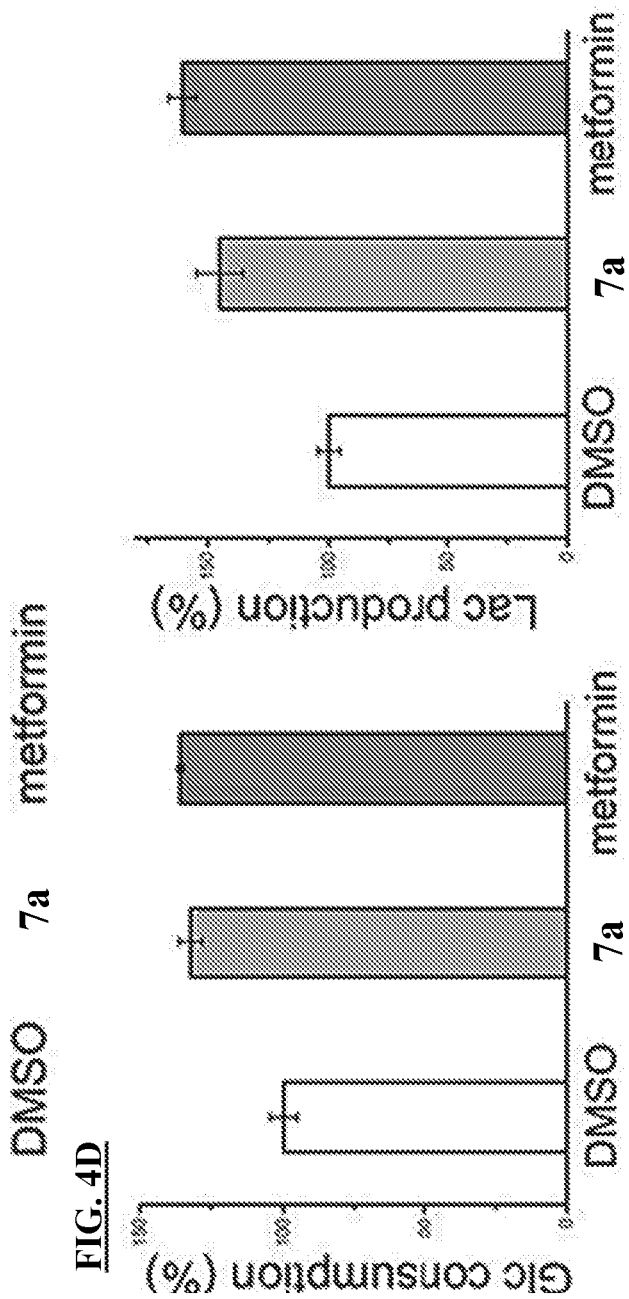

Skeletal muscle cells respond to energy stress by mobilizing glucose transporter GLUT4 to the plasma membrane to facilitate glucose uptake from the environment. The rate of glucose uptake into cultured L6 myotubes was measured using $^{13}C$-labeled 2-deoxyglucose. Like metformin, a widely prescribed anti-diabetic drug, 7a doubled the rate of glucose uptake, suggesting that, besides its ability to induce heightened hormone response, PI5P4Kβ inhibition has the potential to lower blood glucose levels in an insulin-independent manner (FIG. 4C). After 2 days of cell culture, 7a increased glucose consumption by 32% and increased lactate secretion by 45% (FIG. 4D). Metformin had similar effects. The slightly greater increase in lactate production suggests that a larger proportion, about 38%, of the consumed glucose had been used for lactate fermentation, which produces ATP quickly (albeit less efficiently), as the myocytes attempted (but failed) to restore energy homeostasis.

Figure 5A:
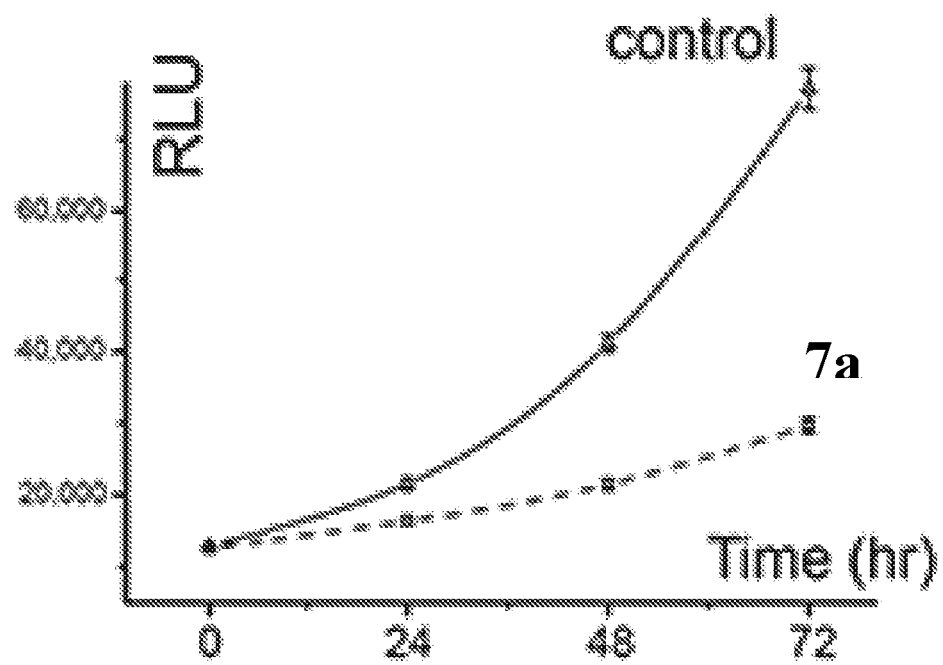
FIGS. 5A-5I are graphs showing that PI5P4Kα/β inhibition caused cell cycle arrest.
Figure 5A:
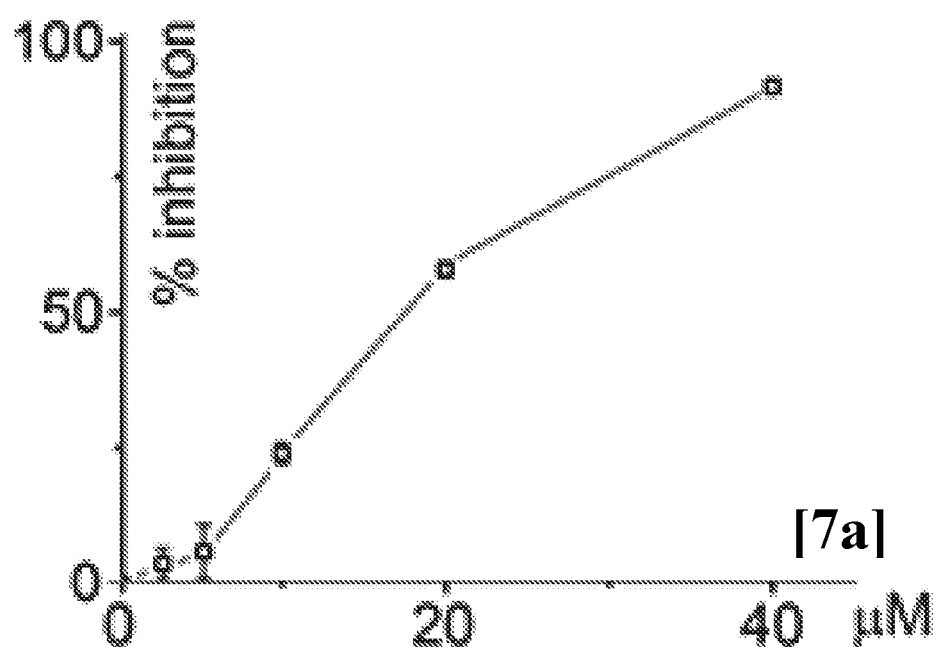
Figure 5B:
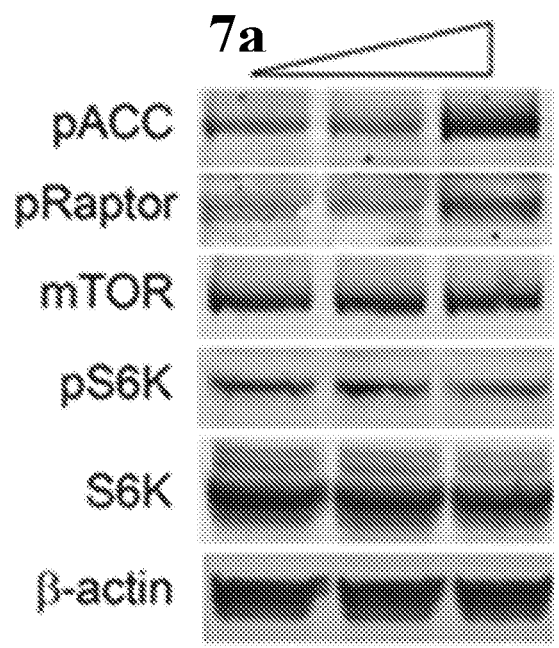
Figure 5C:
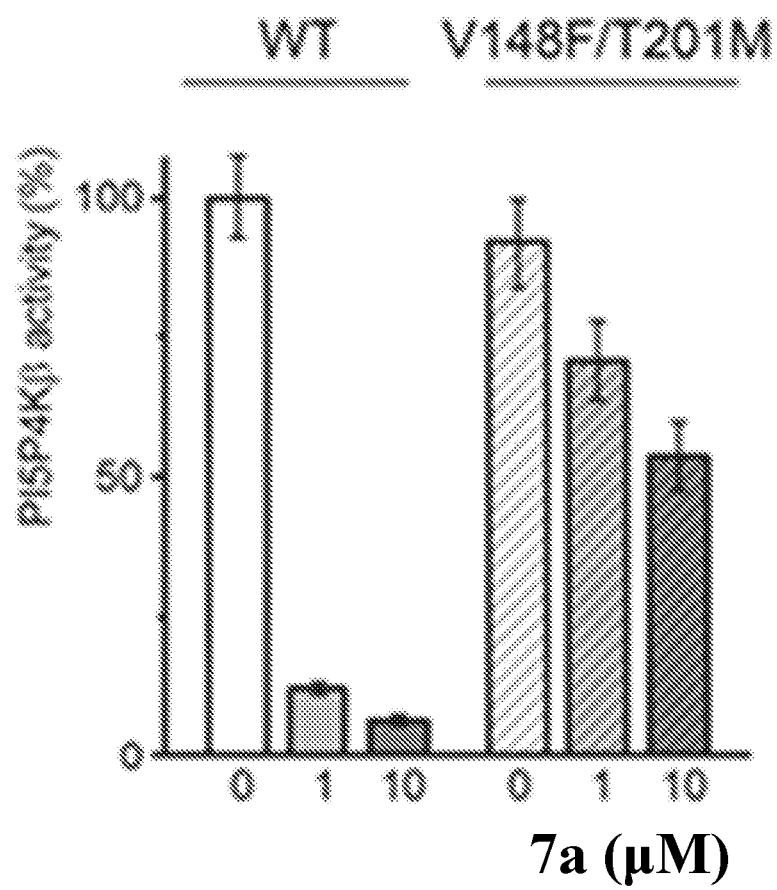
Figure 5C:
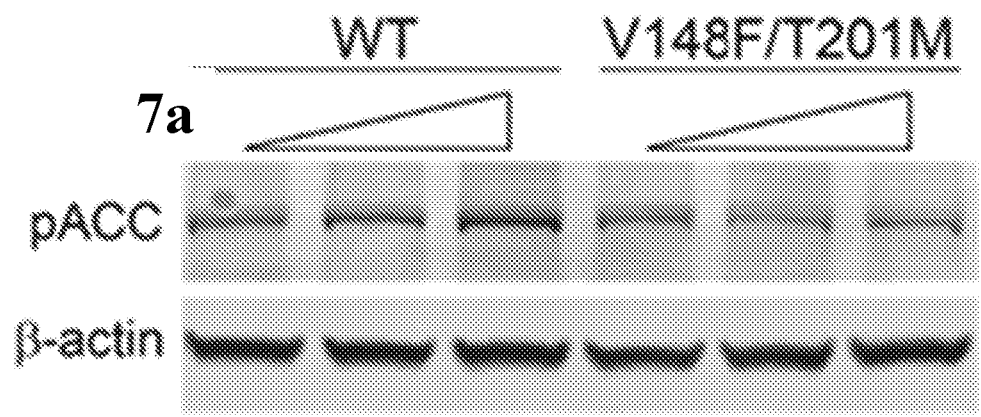
Figure 5D:
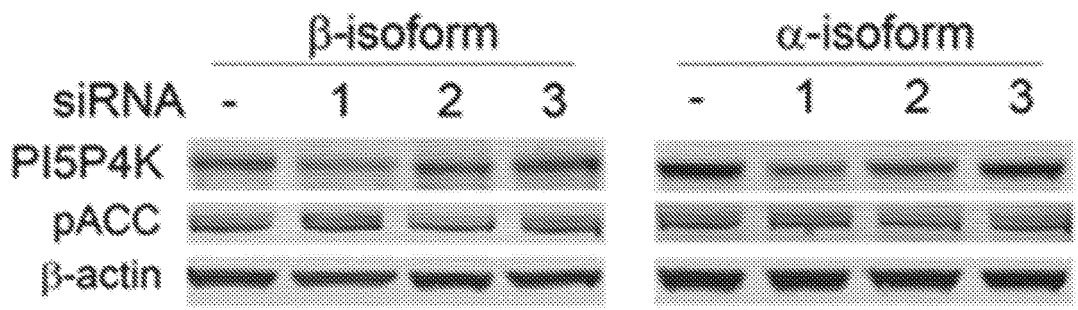
Figure 5E:
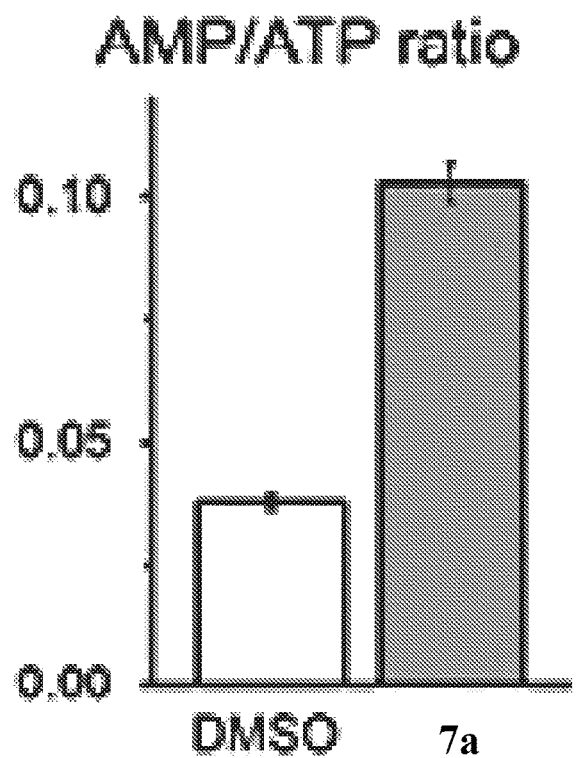
Figure 13A:
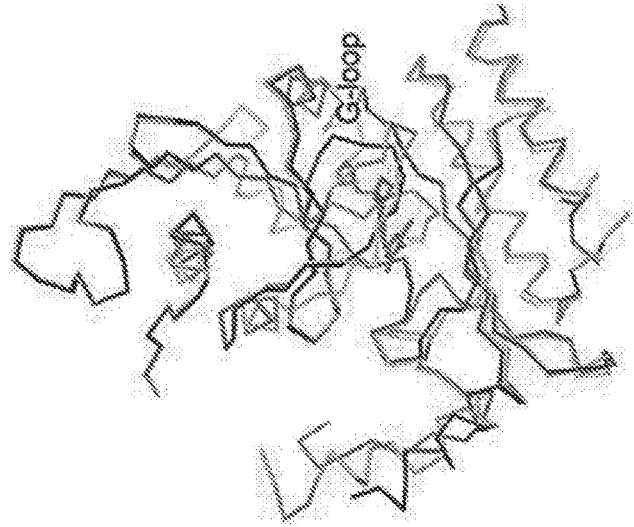
FIGS. 13A-13D are diagrams showing the crystal structures of PI5P4Kβ and its complex with 7a. In the co-crystal, the inhibitor is found in only one of the two protomers in the asymmetric unit.
Figure 13B:
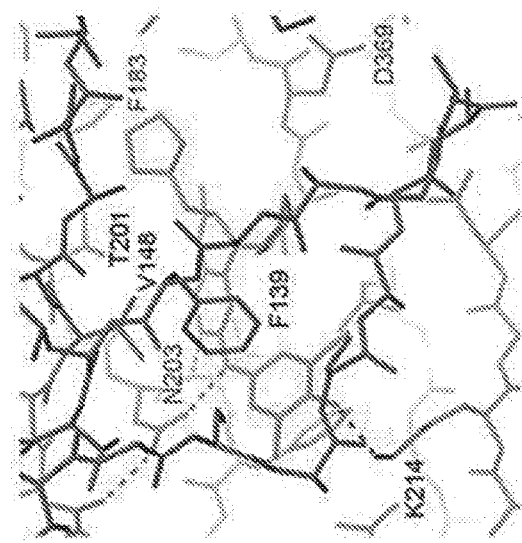
Figure 13D:
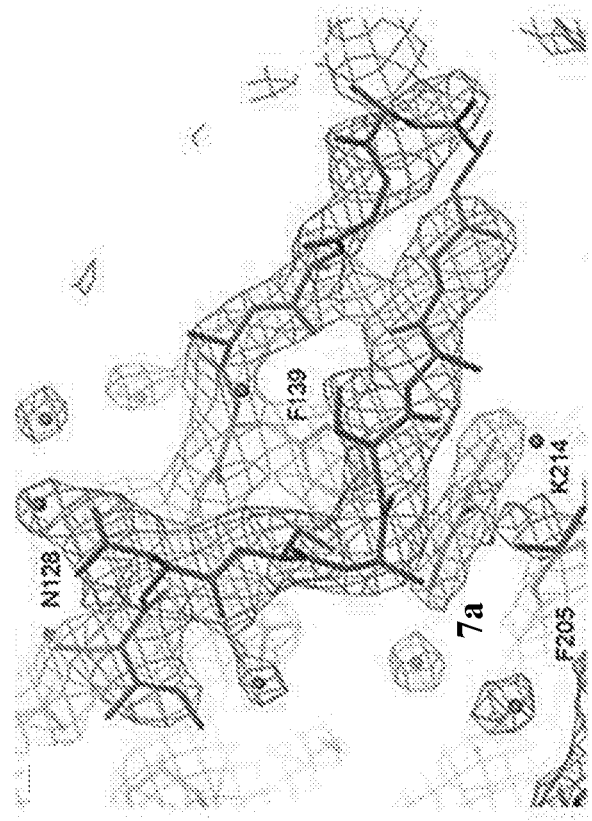
Figure 13C:
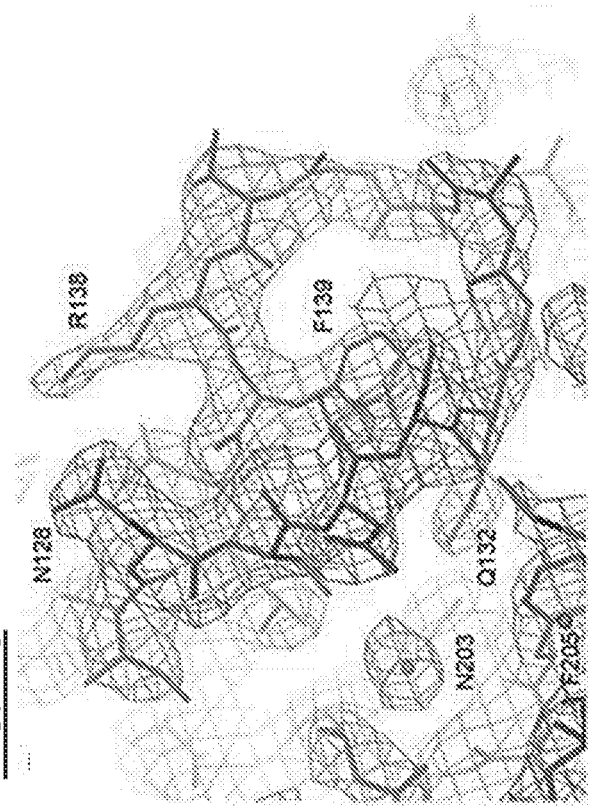

Example 5: PI5P4Kα/β Inhibition Suppresses Cancer Cell Growth 7a inhibited the growth of BT474 cells, a breast cancer cell line where PI5P4Kβ is overexpressed, in a dose-dependent manner (FIG. 5A). Without intending to be limited to any particular theory, this effect is possibly due to inhibition of both PI5P4Kα and PI5P4Kβ. Western blot analyses showed that AMPK was activated in compound-treated BT474 cells, as phosphorylation of ACC and raptor (another AMPK substrate and a component of mTORC1) were both increased (FIG. 5B). Raptor phosphorylation caused a reduction of mTORC1 activity, resulting in less S6K phosphorylation. To interrogate if AMPK activation was caused by PI5P4Kβ inhibition, a cell line that stably expressed a mutant form of the kinase (V148F/T201M) that is refractory to 7a inhibition was generated. As suggested by the crystal structure, the bulkier side chains at positions 148 and 201 sterically clash with the inhibitor but would have a minimal impact on ATP binding (FIG. 13B). In vitro kinase assay confirmed that the mutant retained about 90% wildtype activity but had a weaker affinity for 7a ($K_i$>10 µM; FIG. 5C). Expressing the double mutant in BT474 cells prevented 7a-induced AMPK activation, whereas cells similarly constructed to express the wildtype kinase remained sensitive to the inhibitor (FIG. 5C). Without intending to be limited to any particular theory, this result suggests that PI5P4Kβ is the intracellular target of 7a linked to AMPK activation. In agreement with this conclusion, siRNA knockdown of PI5P4Kβ expression in BT474 cells increased ACC phosphorylation (FIG. 5D). siRNA knockdown of PI5P4Kα also slightly increased ACC phosphorylation, suggesting that, in this cell line at least, PI5P4Kα plays a role in controlling AMPK activity. Tandem mass spectrometry showed that, in BT474 cells, the AMP/ATP ratio is higher than that in C2Cl2 myotubes, and that 7a treatment further increased AMP/ATP ratio by 3-fold, which explains the increase in AMPK activity (FIG. 5E).

Figure 5F:
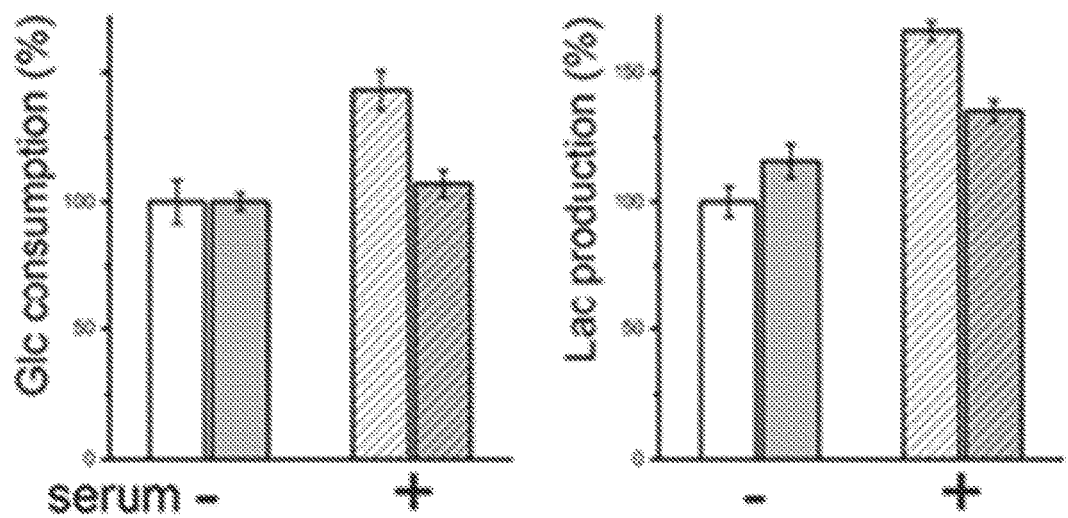
Figure 5G:
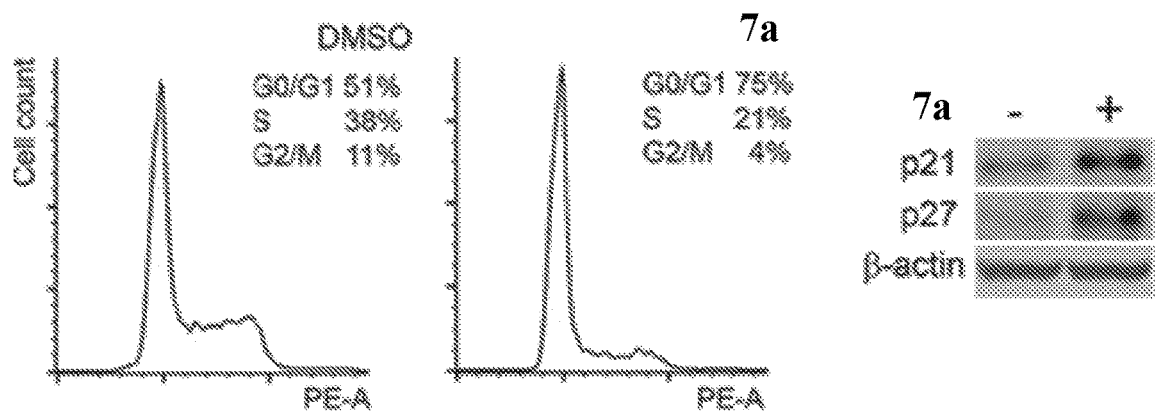
Figure 5H:
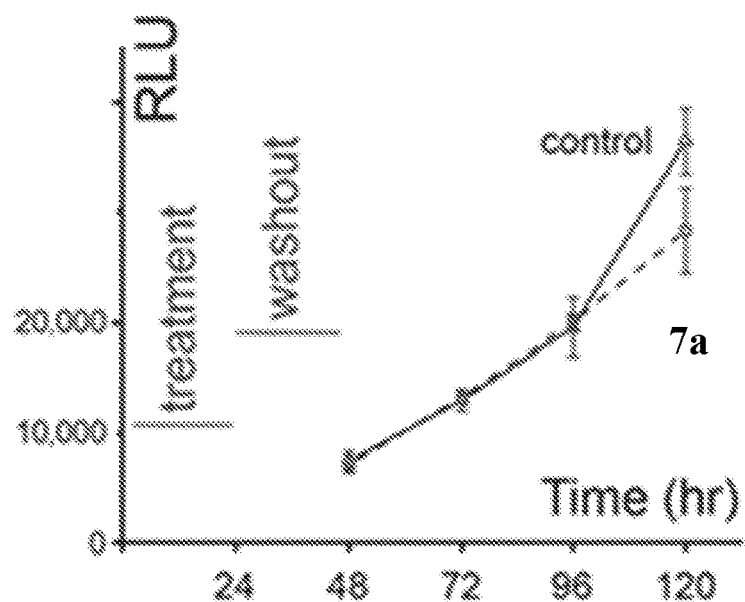

While culturing BT474 cells, it was observed that 7a treatment significantly delayed acidification of the media that contained serum, which was opposite of what was observed previously in the myotube experiment. In the absence of the test compound, serum caused a major increase in both glucose consumption and lactate secretion (FIG. 5F). Although 7a slightly increased lactate fermentation in the absence of serum, it prevented the metabolic switch that was induced by serum. Transition of cells from a resting state to a proliferative state is often accompanied by enhanced aerobic glycolysis (the Warburg effect). Therefore, it was tested whether pharmacological inhibition of the lipid kinases hindered cell cycle progression. Flow cytometry analysis showed that 7a treatment caused accumulation of cells in the $G_0/G_1$ phase, which was corroborated by increased levels of p21 and p27, known cell-cycle inhibitors (FIG. 5G). The arrest at the Gi/S checkpoint appeared to be transient. Upon removal of the inhibitor from culture media, the cells were able to fully recover and regain the ability to proliferate, at a rate comparable to untreated cells (FIG. 5H).

Figure 5I:
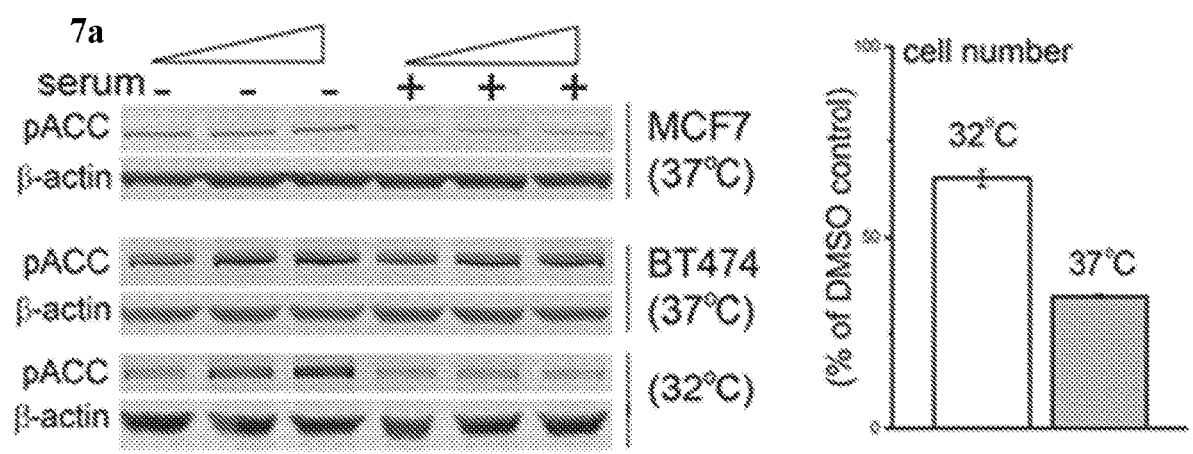

The synthetic lethal interaction between PI5P4Kα/β and tumor suppressor p53 prompted the examination into the role of p53 in the activation of AMPK when the lipid kinases were inhibited. The effects of 7a, in the absence of serum, on BT474 cells, which harbor a temperature sensitive p53 mutation (E285K), and MCF7 cells, which have the wild-type p53, were compared. 7a treatment caused AMPK activation in both cell lines (FIG. 5I). Lowering the culturing temperature of BT474 cells to 32° C., which restores p53 function, had no effect on AMPK activation. The experiments were then repeated with serum. AMPK was activated in BT474 cells at 37° C. In BT474 cells cultured at 32° C., or in MCF7 cells, 7a treatment no longer caused AMPK activation. Without intending to be limited to any particular theory, these results indicate a serum-dependent function of p53 that can resolve the energy stress induced by PI5P4α/β inhibition. At 32° C., the growth of BT474 cells also became less sensitive to 7a inhibition (FIG. 5I).

ENUMERATED EMBODIMENTS

The following exemplary embodiments are provided, the numbering of which is not to be construed as designating levels of importance.

Embodiment 1 provides a compound of Formula (IA) or a salt, solvate, enantiomer, diastereoisomer, or tautomer thereof:

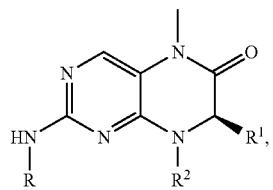

(IA)

wherein:
R is

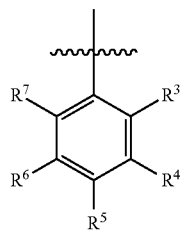

or heteroaryl, wherein the heteroaryl is optionally substituted with at least one selected from the group consisting of $C_1$-$C_6$ alkyl, $C_3$-$C_8$ cycloalkyl, $C_1$-$C_6$ alkoxy, $C_3$-$C_8$ cycloalkoxy, halogen, —OH, —C(=O)OH, —C(=O)$C_1$-$C_6$ alkyl, —C(=O)$C_3$-$C_8$ cycloalkyl, thiol, $C_1$-$C_6$ thioalkoxy, and —NR'R', wherein each occurrence of R' is independently H or $C_1$-$C_6$ alkyl or the two R' bound to the N combine to form 3-7 membered heterocyclyl;

$R^1$ is selected from the group consisting of $C_1$-$C_6$ alkyl (such as, but not limited to, —CH(CH$_3$)$_2$), $C_3$-$C_8$ cycloalkyl, $C_1$-$C_6$ heteroalkyl, $C_3$-$C_8$ heterocycloalkyl, $C_2$-$C_6$ alkenyl, and $C_2$-$C_6$ alkynyl; wherein in $R^1$ each occurrence of alkyl, cycloalkyl, heteroalkyl, heterocycloalkyl, alkenyl, or alkynyl is optionally substituted with at least one substituent selected from the group consisting of $C_1$-$C_6$ alkyl, $C_3$-$C_8$ cycloalkyl, $C_1$-$C_6$ alkoxy, $C_3$-$C_8$ cycloalkoxy, halogen, —OH, thiol, $C_1$-$C_6$ thioalkoxy, phenyl, heteroaryl, hetero-cyclyl, and —NR"R", wherein each occurrence of R' is independently H or $C_1$-$C_6$ alkyl or the two R" bound to the N combine to form 3-7 membered heterocyclyl;

$R^2$ is selected from the group consisting of $C_1$-$C_6$ alkyl, $C_3$-$C_8$ cycloalkyl, $C_1$-$C_6$ heteroalkyl, $C_3$-$C_8$ heterocycloalkyl, $C_2$-$C_6$ alkenyl, and $C_2$-$C_6$ alkynyl; wherein in $R^2$ each occurrence of alkyl, cycloalkyl, heteroalkyl, heterocycloalkyl, alkenyl, or alkynyl is optionally substituted with at least one substituent selected from the group consisting of $C_1$-$C_6$ alkyl, $C_3$-$C_8$ cycloalkyl, $C_1$-$C_6$ alkoxy, $C_3$-$C_8$ cycloalkoxy, halogen, —OH, thiol, $C_1$-$C_6$ thioalkoxy, phenyl, heteroaryl, heterocyclyl, and —NR'''R''', wherein each occurrence of R' is independently H or $C_1$-$C_6$ alkyl or the two R''' bound to the N combine to form 3-7 membered heterocyclyl;

$R^3$ is selected from the group consisting of H, halogen, $C_1$-$C_6$ alkyl, and $C_3$-$C_8$ cycloalkyl;

$R^4$ is selected from the group consisting of H, halogen, $C_1$-$C_6$ alkyl, $C_3$-$C_8$ cycloalkyl, —OH, —C(=O)OH, —C(=O)$C_1$-$C_6$ alkyl, and —C(=O)$C_3$-$C_8$ cycloalkyl;

$R^5$ is selected from the group consisting of H, —OH, —C(=O)OH, —C(=O)$C_1$-$C_6$ alkyl, and —C(=O)$C_3$-$C_8$ cycloalkyl;

$R^6$ is selected from the group consisting of H, halogen, $C_1$-$C_6$ alkyl, $C_3$-$C_8$ cycloalkyl, —OH, —C(=O)OH, —C(=O)$C_1$-$C_6$ alkyl, and —C(=O)$C_3$-$C_8$ cycloalkyl; and $R^7$ is selected from the group consisting of H, halogen, $C_1$-$C_6$ alkyl, and $C_3$-$C_8$ cycloalkyl.

Embodiment 2 provides the compound of Embodiment 1, which is:

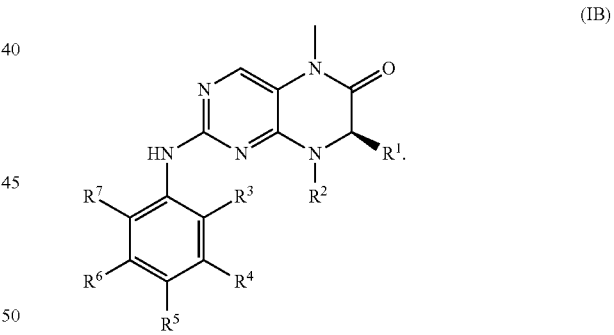

(IB)

Embodiment 3 provides a compound of Formula (IIA) or a salt, solvate, enantiomer, diastereoisomer, or tautomer thereof:

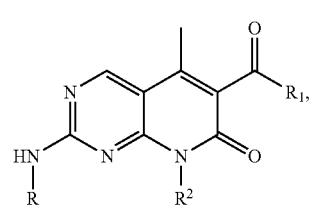

(IIA)

wherein:

R is

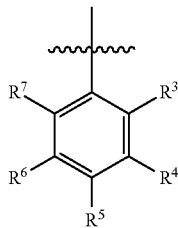

R⁵ or heteroaryl, wherein the heteroaryl is optionally substituted with at least one selected from the group consisting of $C_1$-$C_6$ alkyl, $C_3$-$C_8$ cycloalkyl, $C_1$-$C_6$ alkoxy, $C_3$-$C_8$ cycloalkoxy, halogen, —OH, —C(=O)OH, —C(=O)$C_1$-$C_6$ alkyl, —C(=O)$C_3$-$C_8$ cycloalkyl, thiol, $C_1$-$C_6$ thioalkoxy, and —NR'R', wherein each occurrence of R' is independently H or $C_1$-$C_6$ alkyl or the two R' bound to the N combine to form 3-7 membered heterocyclyl;

$R^1$ is selected from the group consisting of $C_1$-$C_6$ alkyl (such as, but not limited to, —CH(CH₃)₂), $C_3$-$C_8$ cycloalkyl, $C_1$-$C_6$ heteroalkyl, $C_3$-$C_8$ heterocycloalkyl, $C_2$-$C_6$ alkenyl, and $C_2$-$C_6$ alkynyl; wherein in $R^1$ each occurrence of alkyl, cycloalkyl, heteroalkyl, heterocycloalkyl, alkenyl, or alkynyl is optionally substituted with at least one substituent selected from the group consisting of $C_1$-$C_6$ alkyl, $C_3$-$C_8$ cycloalkyl, $C_1$-$C_6$ alkoxy, $C_3$-$C_8$ cycloalkoxy, halogen, —OH, thiol, $C_1$-$C_6$ thioalkoxy, phenyl, heteroaryl, heterocyclyl, and —NR"R", wherein each occurrence of R' is independently H or $C_1$-$C_6$ alkyl or the two R" bound to the N combine to form 3-7 membered heterocyclyl;

$R^2$ is selected from the group consisting of $C_1$-$C_6$ alkyl, $C_3$-$C_8$ cycloalkyl, $C_1$-$C_6$ heteroalkyl, $C_3$-$C_8$ heterocycloalkyl, $C_2$-$C_6$ alkenyl, and $C_2$-$C_6$ alkynyl; wherein in $R^2$ each occurrence of alkyl, cycloalkyl, heteroalkyl, heterocycloalkyl, alkenyl, or alkynyl is optionally substituted with at least one substituent selected from the group consisting of $C_1$-$C_6$ alkyl, $C_3$-$C_8$ cycloalkyl, $C_1$-$C_6$ alkoxy, $C_3$-$C_8$ cycloalkoxy, halogen, —OH, thiol, $C_1$-$C_6$ thioalkoxy, phenyl, heteroaryl, heterocyclyl, and —NR'''R''', wherein each occurrence of R' is independently H or $C_1$-$C_6$ alkyl or the two R''' bound to the N combine to form 3-7 membered heterocyclyl;

$R^3$ is selected from the group consisting of H, halogen, $C_1$-$C_6$ alkyl, and $C_3$-$C_8$ cycloalkyl;

$R^4$ is selected from the group consisting of H, halogen, $C_1$-$C_6$ alkyl, $C_3$-$C_8$ cycloalkyl, —OH, —C(=O)OH, —C(=O)$C_1$-$C_6$ alkyl, and —C(=O)$C_3$-$C_8$ cycloalkyl;

$R^5$ is selected from the group consisting of H, —OH, —C(=O)OH, —C(=O)$C_1$-$C_6$ alkyl, and —C(=O)$C_3$-$C_8$ cycloalkyl;

$R^6$ is selected from the group consisting of H, halogen, $C_1$-$C_6$ alkyl, $C_3$-$C_8$ cycloalkyl, —OH, —C(=O)OH, —C(=O)$C_1$-$C_6$ alkyl, and —C(=O)$C_3$-$C_8$ cycloalkyl; and $R^7$ is selected from the group consisting of H, halogen, $C_1$-$C_6$ alkyl, and $C_3$-$C_8$ cycloalkyl.

Embodiment 4 provides the compound of Embodiment 3, which is:

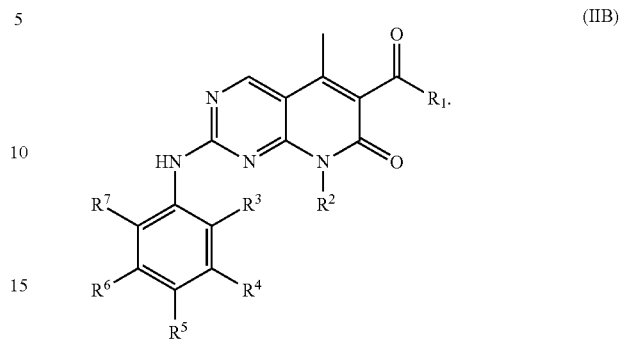

(IIB)

Embodiment 5 provides the compound of Embodiment 1 or 3, wherein R is heteroaryl selected from the group consisting of 1H-benzo[d][1,2,3]triazolyl, triazolyl, thiazolyl, oxazolyl, isooxazolyl, oxadiazolyl, thiodiazolyl, pyridinyl, pyrimidinyl, pyrazinyl, and thiophenyl.

Embodiment 6 provides the compound of any of Embodiments 1-5, wherein $R^1$ is selected from the group consisting of isopropyl, isobutyl, sec-butyl, tert-butyl, cyclopentylmethyl, cyclohexylmethyl, and

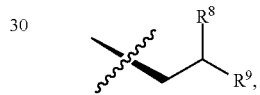

wherein: $R^8$ is selected from the group consisting of $C_1$-$C_6$ alkyl, $C_3$-$C_8$ cycloalkyl, halogen, thiol, $C_1$-$C_6$ thioalkoxy, —OH, $C_1$-$C_6$ alkoxy, and —NR"R"; $R^9$ is selected from the group consisting of H, $C_1$-$C_6$ alkyl, $C_3$-$C_8$ cycloalkyl, halogen, thiol, $C_1$-$C_6$ thioalkoxy, —OH, $C_1$-$C_6$ alkoxy, and —NR"R", wherein each occurrence of R" is independently H or $C_1$-$C_6$ alkyl; wherein if $R^9$ is H, $R^8$ is not methyl.

Embodiment 7 provides the compound of any of Embodiments 1-6, wherein $R^2$ is cyclopentyl.

Embodiment 8 provides the compound of any of Embodiments 1-7, wherein $R^4$ and $R^6$ are independently selected from the group consisting of F, Cl, Br, and I.

Embodiment 9 provides the compound of any of Embodiments 1-8, wherein $R^5$ is OH.

Embodiment 10 provides the compound of any of Embodiments 1-8, wherein at least one of $R^4$, $R^5$, and $R^6$ is selected from the group consisting of —OH, —C(=O)OH, —C(=O)$C_1$-$C_6$ alkyl, and —C(=O)$C_3$-$C_8$ cycloalkyl.

Embodiment 11 provides the compound of any of Embodiments 1-10, which is selected from the group consisting of: (R)-8-cyclopentyl-2-((3,5-difluoro-4-hydroxyphenyl)amino)-7-isopropyl-5-methyl-7,8-dihydropteridin-6 (5H)-one; (R)-8-cyclopentyl-2-((3,5-dichloro-4-hydroxyphenyl)amino)-7-isobutyl-5-methyl-7,8-dihydropteridin-6(5H)-one; (R)-8-cyclopentyl-7-(cyclopentylmethyl)-2-((3,5-dichloro-4-hydroxyphenyl)amino)-5-methyl-7,8-dihydropteridin-6(5H)-one; (R)-7-(cyclohexylmethyl)-8-cyclopentyl-2-((3,5-dichloro-4-hydroxyphenyl)amino)-5-methyl-7,8-dihydropteridin-6 (5H)-one; (R)-8-cyclopentyl-2-((3,5-dichloro-4-hydroxyphenyl)amino)-7-(pyridine-2-ylmethyl)-5-methyl-7,8-dihydropteridin-6(5H)-one; (R)-2-((1H-benzo[d][1,2,3]triazol-5-yl)amino)-8-cyclopentyl-7-(cyclopentylmethyl)-5-methyl-7,8-dihydropteridin-6(5H)-one; (R)-2-((8-cyclopentyl-7-(cyclopentylmethyl)-5-methyl-6-oxo-5,6,7,8- tetrahydropteridin-2-yl)amino)thiazole-5-carboxylic acid; (R)-4-((8-cyclopentyl-7-(cyclopentylmethyl)-5-methyl-6-oxo-5,6,7,8-tetrahydropteridin-2-yl)amino)thiophene-2-carboxylic acid; (R)-4-((8-cyclopentyl-7-(cyclopentylmethyl)-5-methyl-6-oxo-5,6,7,8-tetrahydropteridin-2-yl)amino)-2,6-difluorobenzoic acid; (R)-2-((8-cyclopentyl-5-methyl-6-oxo-7-(pyridin-2-ylmethyl)-5,6,7,8-tetrahydropteridin-2-yl)amino)thiazole-5-carboxylic acid; (R)-2-((1H-benzo[d][1,2,3]triazol-5-yl)amino)-8-cyclopentyl-5-methyl-7-(pyridin-2-ylmethyl)-7,8-dihydropteridin-6(5H)-one; (R)-8-cyclopentyl-2-((3,5-dichloro-4-hydroxyphenyl)amino)-5-methyl-7-(pyrrolidin-1-ylmethyl)-7,8-dihydropteridin-6(5H)-one.

Embodiment 12 provides a pharmaceutical composition comprising the compound of any of Embodiments 1-11.

Embodiment 13 provides a method of treating a p53-null cancer in a subject in need thereof, the method comprising administering to the subject a therapeutically effective amount of the compound of any of Embodiments 1-11.

Embodiment 14 provides the method of Embodiment 13, wherein the cancer is at least one selected from the group consisting of Esophageal/Stomach Cancer, Bladder/Urinary Tract Cancer, Small Cell Lung Cancer, CNS/Brain Cancer, Skin Cancer (Non-Melanoma), Head and Neck Cancer, Ampullary Carcinoma, Burkitt's lymphoma, Esophagogastric Cancer, Colorectal Cancer, Ovarian Cancer, Non-Small Cell Lung Cancer, Small Bowel Cancer, Cancer of Unknown Primary, High-grade glioma K27Mmut, Pancreatic Cancer, Uterine Sarcoma, Bladder Cancer, High-grade glioma K27Mwt, Appendiceal Cancer, Breast Cancer, Soft Tissue Sarcoma, B-cell acute lymphoblastic leukemia (hypodiploid), Endometrial Cancer, Penile Cancer, Glioma, Breast Sarcoma, Hepatobiliary Cancer, Vaginal Cancer, Gastrointestinal Neuroendocrine Tumor, Adrenocortical Carcinoma, Prostate Cancer, Sellar Tumor, Hodgkin Lymphoma, Upper Tract Urothelial Carcinoma, Non-Hodgkin Lymphoma, Melanoma, Bone Cancer, Cutaneous Melanoma, Mesothelioma, Adrenocortical carcinoma, Invasive Breast Carcinoma, Salivary Gland Cancer, B-cell acute lymphoblastic leukemia (non-hypodiploid), Anal Cancer, Embryonal tumor with multilayered rosettes, Ewing's sarcoma, Nerve Sheath Tumor, Wilms' tumors, Germ Cell Tumor, Multiple Myeloma, Cervical Cancer, Gastrointestinal Stromal Tumor, Renal Cell Carcinoma, Mature B-Cell Neoplasms, Myelodysplasia, Thymic Tumor, Sex Cord Stromal Tumor, Atypial teratoid/rhabdoid tumor, Miscellaneous Neuroepithelial Tumor, Medulloblastoma WNT, Medulloblastoma SHH, Rhabdomyosarcoma, Leukemia, Thyroid Cancer, Embryonal Tumor, Wilms Tumor, Osteosarcoma, CNS Cancer, Neuroblastoma, Medulloblastoma Group3, Pheochromocytoma. B-Lymphoblastic Leukemia/Lymphoma.

Embodiment 15 provides the method of Embodiments 13-14, wherein the compound is formulated as part of a pharmaceutical composition.

Embodiment 16 provides the method of any of Embodiments 13-15, wherein the compound is administered by a route selected from the group consisting of parenteral, intratumoral, and/or oral.

Embodiment 17 provides a method of treating at least one metabolic disorder in a subject in need thereof, the method comprising administering to the subject a therapeutically effective amount of the compound of any of Embodiments 1-11.

Embodiment 18 provides the method of Embodiment 17, wherein the at least one metabolic disorder is selected from the group consisting of type 2 diabetes, obesity, liver disease, and heart disease.

The disclosures of each and every patent, patent application, and publication cited herein are hereby incorporated herein by reference in their entirety. Whereas this invention has been disclosed with reference to specific embodiments, it is apparent that other embodiments and variations of this invention may be devised by others skilled in the art without departing from the true spirit and scope of the invention. The appended claims are intended to be construed to include all such embodiments and equivalent variations.

The invention claimed is:

1. A compound of Formula (IA) or a salt, solvate, enantiomer, diastereoisomer, or tautomer thereof:

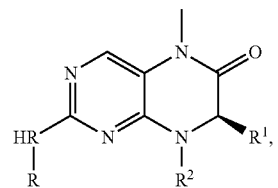

wherein:

R is

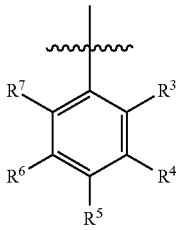

or heteroaryl,
wherein the heteroaryl is optionally substituted with at least one selected from the group consisting of $C_1$-$C_6$ alkyl, $C_3$-$C_8$ cycloalkyl, $C_1$-$C_6$ alkoxy, $C_3$-$C_8$ cycloalkoxy, halogen, —OH, —C(=O)OH, —C(=O)$C_1$-$C_6$ alkyl, —C(=O)$C_3$-$C_8$ cycloalkyl, thiol, $C_1$-$C_6$ thioalkoxy, and —NR'R',
wherein each occurrence of R' is independently H or $C_1$-$C_6$ alkyl or the two R' bound to the N combine to form 3-7 membered heterocyclyl;

$R^1$ is selected from the group consisting of isopropyl, sec-butyl, tert-butyl, $C_3$-$C_8$ cycloalkyl, $C_1$-$C_6$ heteroalkyl, $C_3$-$C_8$ heterocycloalkyl,

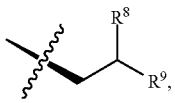

and $C_1$-$C_6$ alkyl substituted with at least one group selected from $C_3$-$C_8$ cycloalkyl, $C_1$-$C_6$ alkoxy, $C_3$-$C_8$ cycloalkoxy, halogen, —OH, thiol, $C_1$-$C_6$ thioalkoxy, phenyl, heteroaryl, heterocyclyl, and —NR"R",
wherein in $R^1$ each occurrence of cycloalkyl, heteroalkyl, or heterocycloalkyl is optionally substituted with at least one substituent selected from the group consisting of $C_1$-$C_6$ alkyl, $C_3$-$C_8$ cycloalkyl, $C_1$-$C_6$ alkoxy, $C_3$-$C_8$ cycloalkoxy, halogen, —OH, thiol, $C_1$-$C_6$ thioalkoxy, phenyl, heteroaryl, heterocyclyl, and —NR"R";
each occurrence of R" is independently H or $C_1$-$C_6$ alkyl or the two R" bound to the N combine to form 3-7 membered heterocyclyl;

$R^2$ is selected from the group consisting of $C_1$-$C_6$ alkyl, $C_3$-$C_8$ cycloalkyl, $C_1$-$C_6$ heteroalkyl, and $C_3$-$C_8$ heterocycloalkyl;
wherein in $R^2$ each occurrence of alkyl, cycloalkyl, heteroalkyl, or heterocycloalkyl is optionally substituted with at least one substituent selected from the group consisting of $C_1$-$C_6$ alkyl, $C_3$-$C_8$ cycloalkyl, $C_1$-$C_6$ alkoxy, $C_3$-$C_8$ cycloalkoxy, halogen, —OH, thiol, $C_1$-$C_6$ thioalkoxy, phenyl, heteroaryl, heterocyclyl, and —NR'''R''',
wherein each occurrence of R''' is independently H or $C_1$-$C_6$ alkyl or the two R''' bound to the N combine to form 3-7 membered heterocyclyl;

$R^3$ is selected from the group consisting of H, halogen, $C_1$-$C_6$ alkyl, and $C_3$-$C_8$ cycloalkyl;

$R^4$ is selected from the group consisting of H, halogen, $C_1$-$C_6$ alkyl, $C_3$-$C_8$ cycloalkyl, —OH, —C(=O)OH, —C(=O)$C_1$-$C_6$ alkyl, and —C(=O)$C_3$-$C_8$ cycloalkyl;

$R^5$ is selected from the group consisting of H, —OH, —C(=O)OH, —C(=O)$C_1$-$C_6$ alkyl, and —C(=O)$C_3$-$C_8$ cycloalkyl;

$R^6$ is selected from the group consisting of H, halogen, $C_1$-$C_6$ alkyl, $C_3$-$C_8$ cycloalkyl, —OH, —C(=O)OH, —C(=O)$C_1$-$C_6$ alkyl, and —C(=O)$C_3$-$C_8$ cycloalkyl;

$R^7$ is selected from the group consisting of H, halogen, $C_1$-$C_6$ alkyl, and $C_3$-$C_8$ cycloalkyl;

$R^8$ is selected from the group consisting of $C_1$-$C_6$ alkyl, $C_3$-$C_8$ cycloalkyl, halogen, thiol, $C_1$-$C_6$ thioalkoxy, —OH, $C_1$-$C_6$ alkoxy, and —NR"R"; and $R^9$ is selected from the group consisting of H, $C_1$-$C_6$ alkyl, $C_3$-$C_8$ cycloalkyl, halogen, thiol, $C_1$-$C_6$ thioalkoxy, —OH, $C_1$-$C_6$ alkoxy, and —NR"R",
wherein, if $R^9$ is H, $R^8$ is not methyl.

2. The compound of claim 1, which is:

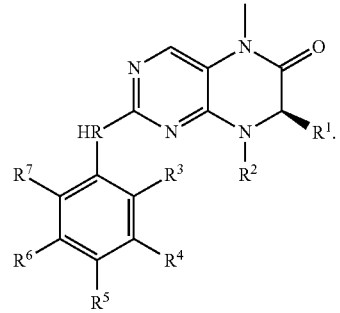

(IB)

3. The compound of claim 1, wherein R is heteroaryl selected from the group consisting of 1H-benzo[d][1,2,3]triazolyl, triazolyl, thiazolyl, oxazolyl, isooxazolyl, oxadiazolyl, thiodiazolyl, pyridinyl, pyrimidinyl, triazinyl, pyrazinyl, thiophenyl, benzotriazolyl, benzamidazolyl, indolyl, indazolyl, pyrrolyl, and pyrazolyl.

4. The compound of claim 1, wherein $R^1$ is selected from the group consisting of isopropyl, isobutyl, sec-butyl, tert-butyl, cyclopentylmethyl, and cyclohexylmethyl.

5. The compound of claim 1, wherein $R^2$ is cyclopentyl.

6. The compound of claim 1, wherein $R^4$ and $R^6$ are independently selected from the group consisting of F, Cl, Br, and I.

7. The compound of claim 1, wherein $R^5$ is OH.

8. The compound of claim 1, wherein at least one of $R^4$, $R^5$, and $R^6$ is selected from the group consisting of —OH, —C(=O)OH, —C(=O)$C_1$-$C_6$ alkyl, and —C(=O)$C_3$-$C_8$ cycloalkyl.

9. The compound of claim 1, which is selected from the group consisting of:

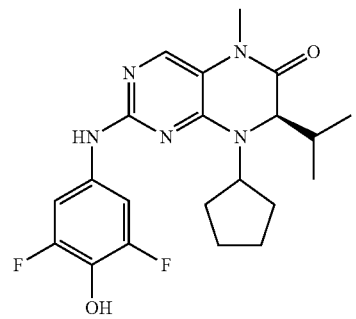 [SMILES: CC(C)[C@@H]1C(=O)N(C)c2cnc(Nc3cc(F)c(O)c(F)c3)nc2N1C1CCCC1]

(R)-8-cyclopentyl-2-((3,5-difluoro-4-hydroxyphenyl)
amino)-7-isopropyl-5-methyl-7,8-dihydropteridin-6
(5H)-one;

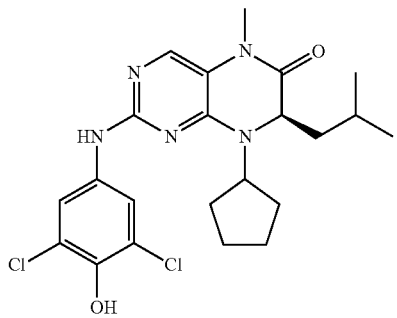 [SMILES: CC(C)C[C@@H]1C(=O)N(C)c2cnc(Nc3cc(Cl)c(O)c(Cl)c3)nc2N1C1CCCC1]

(R)-8-cyclopentyl-2-((3,5-dichloro-4-hydroxyphenyl)
amino)-7-isobutyl-5-methyl-7,8-dihydropteridin-6
(5H)-one;

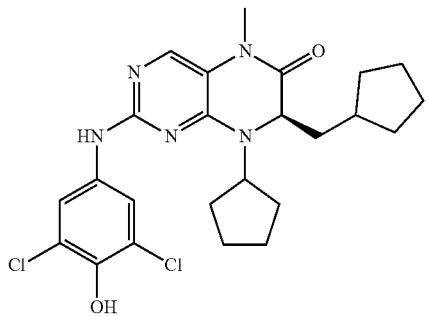 [SMILES: CN1C(=O)[C@@H](CC2CCCC2)N(C2CCCC2)c2nc(Nc3cc(Cl)c(O)c(Cl)c3)ncc21]

(R)-8-cyclopentyl-7-(cyclopentylmethyl)-2-((3,5-di-
chloro-4-hydroxyphenyl)amino)-5-methyl-7,8-dihy-
dropteridin-6(5H)-one;

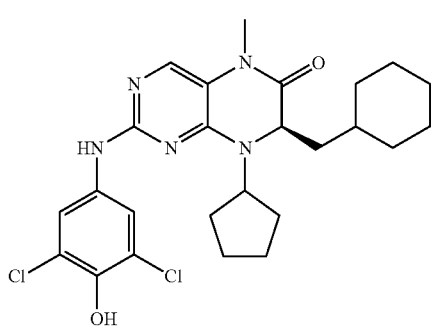 [SMILES: CN1C(=O)[C@@H](CC2CCCCC2)N(C2CCCC2)c2nc(Nc3cc(Cl)c(O)c(Cl)c3)ncc21]

(R)-7-(cyclohexylmethyl)-8-cyclopentyl-2-((3,5-di-
chloro-4-hydroxyphenyl)amino)-5-methyl-7,8-dihy-
dropteridin-6(5H)-one;

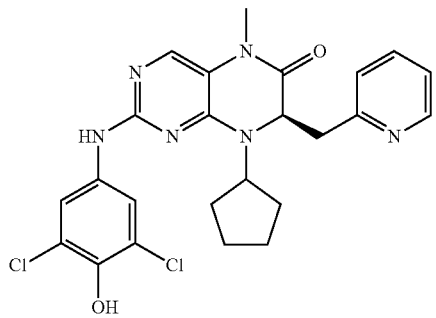 [SMILES: CN1C(=O)[C@@H](Cc2ccccn2)N(C2CCCC2)c2nc(Nc3cc(Cl)c(O)c(Cl)c3)ncc21]

(R)-8-cyclopentyl-2-((3,5-dichloro-4-hydroxyphenyl)
amino)-7-(pyridine-2-ylmethyl)-5-methyl-7,8-dihy-
dropteridin-6(5H)-one;

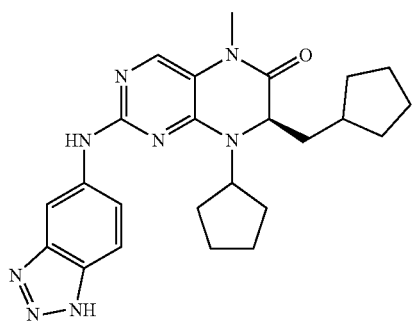 [SMILES: CN1C(=O)[C@@H](CC2CCCC2)N(C2CCCC2)c2nc(Nc3ccc4[nH]nnc4c3)ncc21]

(R)-2-((1H-benzo[d][1,2,3]triazol-5-yl)amino)-8-cyclo-
pentyl-7-(cyclopentylmethyl)-5-methyl-7,8-dihydrop-
teridin-6(5H)-one;

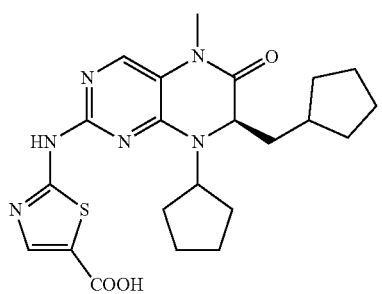 [SMILES: CN1C(=O)[C@@H](CC2CCCC2)N(C2CCCC2)c2nc(Nc3ncc(C(=O)O)s3)ncc21]

(R)-2-((8-cyclopentyl-7-(cyclopentylmethyl)-5-methyl-
6-oxo-5,6,7,8-tetrahydropteridin-2-yl)amino)thiazole-
5-carboxylic acid;

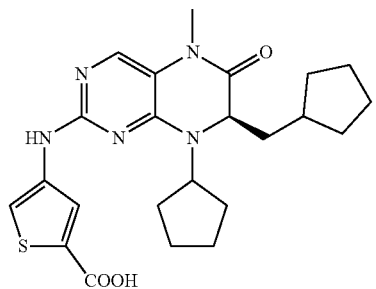 [SMILES: CN1C(=O)[C@@H](CC2CCCC2)N(C2CCCC2)c2nc(Nc3csc(C(=O)O)c3)ncc21]

(R)-4-((8-cyclopentyl-7-(cyclopentylmethyl)-5-methyl-6-oxo-5,6,7,8-tetrahydropteridin-2-yl)amino)thiophene-2-carboxylic acid;

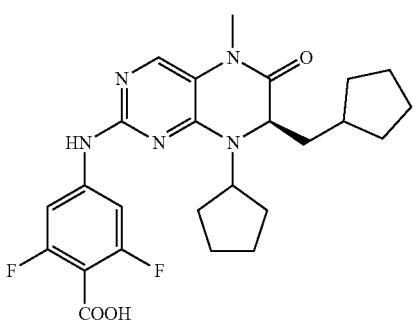 [SMILES: CN1C(=O)[C@@H](CC2CCCC2)N(C2CCCC2)c2nc(Nc3cc(F)c(C(=O)O)c(F)c3)ncc21]

(R)-4-((8-cyclopentyl-7-(cyclopentylmethyl)-5-methyl-6-oxo-5,6,7,8-tetrahydropteridin-2-yl)amino)-2,6-difluorobenzoic acid;

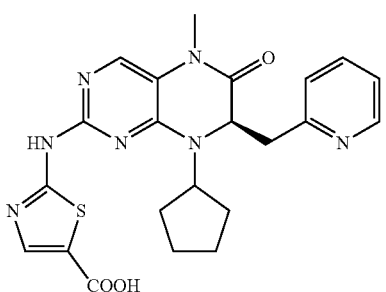 [SMILES: CN1C(=O)[C@@H](Cc2ccccn2)N(C2CCCC2)c2nc(Nc3ncc(C(=O)O)s3)ncc21]

(R)-2-((8-cyclopentyl-5-methyl-6-oxo-7-(pyridin-2-ylmethyl)-5,6,7,8-tetrahydropteridin-2-yl)amino)thiazole-5-carboxylic acid;

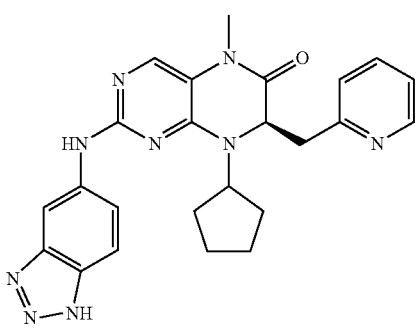 [SMILES: CN1C(=O)[C@@H](Cc2ccccn2)N(C2CCCC2)c2nc(Nc3ccc4[nH]nnc4c3)ncc21]

(R)-2-((1H-benzo[d][1,2,3]triazol-5-yl)amino)-8-cyclopentyl-5-methyl-7-(pyridin-2-ylmethyl)-7,8-dihydropteridin-6(5H)-one; and

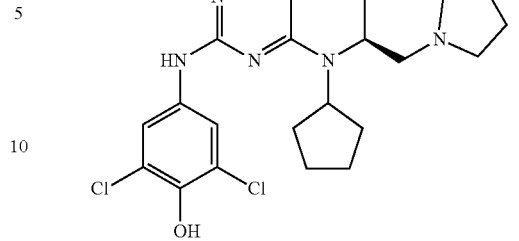

(R)-8-cyclopentyl-2-((3,5-dichloro-4-hydroxyphenyl)amino)-5-methyl-7-(pyrrolidin-1-ylmethyl)-7,8-dihydropteridin-6(5H)-one.

10. A pharmaceutical composition comprising the compound of claim 1.

11. A method of treating a p53-null breast cancer in a subject in need thereof, the method comprising administering to the subject a therapeutically effective amount of a compound of Formula (IA) or a salt, solvate, enantiomer, diastereoisomer, or tautomer thereof:

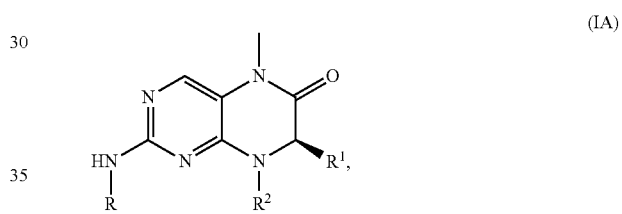
(IA)

wherein:

R is

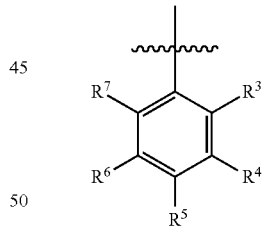

or heteroaryl,
wherein the heteroaryl is optionally substituted with at least one selected from the group consisting of $C_1$-$C_6$ alkyl, $C_3$-$C_8$ cycloalkyl, $C_1$-$C_6$ alkoxy, $C_3$-$C_8$ cycloalkoxy, halogen, —OH, —C(=O)OH, —C(=O)$C_1$-$C_6$ alkyl, —C(=O)$C_3$-$C_8$ cycloalkyl, thiol, $C_1$-$C_6$ thioalkoxy, and —NR'R',
wherein each occurrence of R' is independently H or $C_1$-$C_6$ alkyl or the two R' bound to the N combine to form 3-7 membered heterocyclyl;

$R^1$ is selected from the group consisting of isopropyl, sec-butyl, tert-butyl, $C_3$-$C_8$ cycloalkyl, $C_1$-$C_6$ heteroalkyl, $C_3$-$C_8$ heterocycloalkyl,

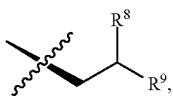

and $C_1$-$C_6$ alkyl substituted with at least one group selected from $C_3$-$C_8$ cycloalkyl, $C_1$-$C_6$ alkoxy, $C_3$-$C_8$ cycloalkoxy, halogen, —OH, thiol, $C_1$-$C_6$ thioalkoxy, phenyl, heteroaryl, heterocyclyl, and —NR"R", wherein in $R^1$ each occurrence of cycloalkyl, heteroalkyl, or heterocycloalkyl is optionally substituted with at least one substituent selected from the group consisting of $C_1$-$C_6$ alkyl, $C_3$-$C_8$ cycloalkyl, $C_1$-$C_6$ alkoxy, $C_3$-$C_8$ cycloalkoxy, halogen, —OH, thiol, $C_1$-$C_6$ thioalkoxy, phenyl, heteroaryl, heterocyclyl, and —NR"R", each occurrence of R" is independently H or $C_1$-$C_6$ alkyl or the two R" bound to the N combine to form 3-7 membered heterocyclyl;

$R^2$ is selected from the group consisting of $C_1$-$C_6$ alkyl, $C_3$-$C_8$ cycloalkyl, $C_1$-$C_6$ heteroalkyl, and $C_3$-$C_8$ heterocycloalkyl;

wherein in $R^2$ each occurrence of alkyl, cycloalkyl, heteroalkyl, or heterocycloalkyl is optionally substituted with at least one substituent selected from the group consisting of $C_1$-$C_6$ alkyl, $C_3$-$C_8$ cycloalkyl, $C_1$-$C_6$ alkoxy, $C_3$-$C_8$ cycloalkoxy, halogen, —OH, thiol, $C_1$-$C_6$ thioalkoxy, phenyl, heteroaryl, heterocyclyl, and —NR'"R"', wherein each occurrence of R'" is independently H or $C_1$-$C_6$ alkyl or the two R'" bound to the N combine to form 3-7 membered heterocyclyl;

$R^3$ is selected from the group consisting of H, halogen, $C_1$-$C_6$ alkyl, and $C_3$-$C_8$ cycloalkyl;

$R^4$ is selected from the group consisting of H, halogen, $C_1$-$C_6$ alkyl, $C_3$-$C_8$ cycloalkyl, —OH, —C(=O)OH, —C(=O)$C_1$-$C_6$ alkyl, and —C(=O)$C_3$-$C_5$ cycloalkyl;

$R^5$ is selected from the group consisting of H, —OH, —C(=O)OH, —C(=O)$C_1$-$C_6$ alkyl, and —C(=O)$C_3$-$C_5$ cycloalkyl;

$R^6$ is selected from the group consisting of H, halogen, $C_1$-$C_6$ alkyl, $C_3$-$C_8$ cycloalkyl, —OH, —C(=O)OH, —C(=O)$C_1$-$C_6$ alkyl, and —C(=O)$C_3$-$C_8$ cycloalkyl;

$R^7$ is selected from the group consisting of H, halogen, $C_1$-$C_6$ alkyl, and $C_3$-$C_8$ cycloalkyl;

$R^8$ is selected from the group consisting of $C_1$-$C_6$ alkyl, $C_3$-$C_8$ cycloalkyl, halogen, thiol, $C_1$-$C_6$ thioalkoxy, —OH, $C_1$-$C_6$ alkoxy, and —NR"R"; and $R^9$ is selected from the group consisting of H, $C_1$-$C_6$ alkyl, $C_3$-$C_8$ cycloalkyl, halogen, thiol, $C_1$-$C_6$ thioalkoxy, —OH, $C_1$-$C_6$ alkoxy, and —NR"R", wherein, if $R^9$ is H, $R^8$ is not methyl.

12. The method of claim 11, wherein the compound is formulated as part of a pharmaceutical composition.

13. The method of claim 11, wherein the compound is administered by a route selected from the group consisting of parenteral, intratumoral, or oral.

* * * * *